United States Patent
Poulet et al.

(10) Patent No.: US 7,910,112 B2
(45) Date of Patent: Mar. 22, 2011

(54) FELINE VACCINES AGAINST AVIAN INFLUENZA

(75) Inventors: Hervé Poulet, Sainte Foy-lès-Lyon (FR); Jean Christophe Audonnet, Lyons (FR); Michel Bublot, Chaponost (BE); Jiansheng Yao, North York (CA)

(73) Assignee: Merial Limited, Duluth, GA (US)

( * ) Notice: Subject to any disclaimer, the term of this patent is extended or adjusted under 35 U.S.C. 154(b) by 729 days.

(21) Appl. No.: 11/557,040

(22) Filed: Nov. 6, 2006

(65) Prior Publication Data

US 2008/0107681 A1    May 8, 2008

(51) Int. Cl.
*A61K 39/145*    (2006.01)
*C12N 15/44*    (2006.01)
*C12N 15/00*    (2006.01)

(52) U.S. Cl. .................. 424/209.1; 435/320.1; 514/44

(58) Field of Classification Search ................. None
See application file for complete search history.

(56) References Cited

U.S. PATENT DOCUMENTS 5,494,807 A * 2/1996 Paoletti et al. .............. 435/69.3
6,340,462 B1 * 1/2002 Paoletti ...................... 424/199.1

OTHER PUBLICATIONS

Taylor et al. Vaccine, 1988, vol. 6, No. 6, pp. 504-508.*
Swayne et al. Avian Diseases, 1997, vol. 41, No. 4, pp. 912-922.*
Taylor et al. Proceeding of the Third International Symposium on Avian Influenza, 1992, pp. 311-335.*
Karaca et al. Clinical and Diagnostic Laboratory Immunology, Nov. 2005, vol. 12, No. 11, pp. 1340-1342.*

* cited by examiner

*Primary Examiner* — Bao Li
(74) *Attorney, Agent, or Firm* — Judy Jarecki-Black; Chad Kitchen; Merial Limited

(57) ABSTRACT

The present invention encompasses influenza vaccines, in particular avian influenza vaccines. The vaccine may be a recombinant poxvirus vaccine or an inactivated vaccine. The invention also encompasses recombinant poxvirus vectors encoding and expressing avian influenza antigens, epitopes or immunogens which can be used to protect animals, in particular felids, against avian influenza.

13 Claims, 22 Drawing Sheets

Fragment of vFP2211

6243 bp (molecule 289059 bp)

| Lane: | Unique fragments hybridized with AIV probe (red) | |
|---|---|---|
| 1. Fowlpox/ BamHI | 29181bp | 22576bp |
| 2. vFP2211/BamHI | 23567bp | |
| 3. Fowlpox/HindIII | 14500bp | 2121bp |
| 4. vFP2211/HindIII | 17141bp | |
| 5. Fowlpox/PstI | 28838bp | |
| 6. vFP2211/PstI | 24376bp | |

Lane:
1. 1Kb+ DNA Marker
2. Fowlpox BamHI
3. vFP2211.4.1.1.1 BamHI
4. vFP2211.4.1.1.1 BamHI
5. 1Kb+ DNA Marker
6. Fowlpox HindIII
7. vFP2211.4.1.1.1 HindIII
8. vFP2211.4.1.1.1 HindIII
9. 1Kb+ DNA Marker
10. Fowlpox PstI
11. vFP2211.4.1.1.1 PstI
12. vFP2211.4.1.1.1 PstI
13. Gene Ruler Marker 1. Marker
2. Mock infection, cell pellet
3. Fowlpox infection, cell pellet
4. vFP2211.2.2.2.2 infection, cell pellet
5. vFP2211.4.1.1.1 infection, cell pellet
6. Empty
7. Mock infection, culture medium
8. Fowlpox infection, culture medium
9. vFP2211.2.2.2.2 infection, culture medium
10. vFP2211.4.1.1.1. infection, culture medium

FIGURE 7 (1/2)

```
                              1                                                                      70
H5 HA (CK-Indonesia-03)  (1)  ATGGAGAAAATAGTGCTTCTTCTTGCAATAGTCAGTCTTGTTAAAAGTGATCAGATTTGCATTGGTTACC
       Synthetic H5 HA  (1)  ATGGAGAAAATCGTGCTGCTGCTGGCCATCGTGAGCCTGGTGAAAAGCGATCAGATCTGCATCGGCTACC
                              71                                                                     140
H5 HA (CK-Indonesia-03) (71)  ATGCAAACAATTCAACAGAGCAGGTTGACACAATAATGGAAAAGAACGTTACTGTTACACATGCCCAAGA
       Synthetic H5 HA (71)  ACGCCAACAACAGCACAGAGCAAGTGGACACAATCATGGAAAAGAACGTGACCGTGACACACGCCCAGGA
                              141                                                                    210
H5 HA (CK-Indonesia-03)(141)  CATACTGGAAAAGACACACAACGGGAAGCTCTGCGATCTAGATGGAGTGAAGCCTCTAATTTTAAGAGAT
       Synthetic H5 HA(141)  CATCCTGGAAAAGACACACAACGGGAAGCTGTGCGATCTGGATGGAGTGAAGCCTCTGATCCTGAGAGAT
                              211                                                                    280
H5 HA (CK-Indonesia-03)(211)  TGTAGTGTAGCTGGATGGCTCCTCGGGAATCCAATGTGTGACGAATTCATCAATGTACCGGAATGGTCTT
       Synthetic H5 HA(211)  TGCAGCGTGGCCGGATGGCTGCTGGGGAACCCAATGTGCGACGAATTCATCAACGTGCCCGAATGGAGCT
                              281                                                                    350
H5 HA (CK-Indonesia-03)(281)  ACATAGTGGAGAAGGCCAATCCAGCCAATGACCTCTGTTACCCAGGGAATCTCAACGACTATGAAGAACT
       Synthetic H5 HA(281)  ACATCGTGGAGAAGGCCAACCCAGCCAACGACCTGTGCTACCCAGGGAACCTGAACGACTACGAAGAACT
                              351                                                                    420
H5 HA (CK-Indonesia-03)(351)  AAAAGCACCTATTGAGCAGAATAAACCATTTCTCAGAAAATTCAGATCATCGCCCAAAAGTTCTTGGTCCGAT
       Synthetic H5 HA(351)  GAAACACCTGCTGAGCAGAATCAACCACTTTGAGAAAATCCAGATCATCCCCAAAAGCAGCTGGTCCGAT
                              421                                                                    490
H5 HA (CK-Indonesia-03)(421)  CATGAAGCCTCATCAGGGGTGAGCTCAGCATGTCCATACCAGGGAAAGTCCTCCTTTTTTAGAAATGTGG
       Synthetic H5 HA(421)  CACGAAGCCAGCAGCGGAGTGAGCAGCGCCTGCCCATACCAGGGAAAGTCCAGCTTTTTTAGAAACGTGG
                              491                                                                    560
H5 HA (CK-Indonesia-03)(491)  TATGGCTTATCAAAAAGAACAGTGCATACCCAACAATAAAGAGAAGCTACAATAATACCAACCAAGAAGA
       Synthetic H5 HA(491)  TGTGGCTGATCAAAAAGAACAGCGCCTACCCAACAATCAAGAGAAGCTACAACAACACCAACCAGGAACA
                              561                                                                    630
H5 HA (CK-Indonesia-03)(561)  TCTTTTTGGTACTGTGGGGGATTCACCATCCTAATGATGCGGCAGAGCAGACAAGGCTATATCAAAACCCA
       Synthetic H5 HA(561)  TCTGCTGGTGCTGTGGGGGATCCACCACCCTAACGATGCCGCCGAGCAGACAAGGCTGTACCAGAACCCA
                              631                                                                    700
H5 HA (CK-Indonesia-03)(631)  ACCACCTATATTTCCGTTGGGACATCAACACTAAACCAGAGATTGGTACCAAAAATAGCTATTAGATCCA
       Synthetic H5 HA(631)  ACCACCTACATCTCCGTGGGGACAAGCACACTGAACCAGAGACTGGTGCCAAAAATCGCCATCAGATCCA
                              701                                                                    770
H5 HA (CK-Indonesia-03)(701)  AAGTAAACGGGCAAAGTGGAAGAATGGAGTTCTTCTCGGACAATTTTAAAACCGAATGATGCAATCAACTT
       Synthetic H5 HA(701)  AAGTGAACGGGCAGAGCGGAAGAATGGAGTTCTTCTCGGACAATCCTGAAACCCAACGATGCCATCAACTT
                              771                                                                    840
H5 HA (CK-Indonesia-03)(771)  CGAGAGTAATGGAAATTTCATTGCTCCAGAATATGCATACAAAATTGTCAAGAAAGGGGACTCTGCAATT
       Synthetic H5 HA(771)  CGAGAGCAACGGAAACTTCATCGCCCCAGAATACGCCTACAAAATCGTGAAGAAAGGGGACAGCGCCATC
                              841                                                                    910
H5 HA (CK-Indonesia-03)(841)  ATGAAAAGTGAATTGGAATATGGTAACTGCAACACCAAGTGTCAAACTCCAATGGGGGCGATAAACTCTA
       Synthetic H5 HA(841)  ATGAAAAGCGAACTGGAATACGGCAACTGCAACACCAAGTGCCAGACCCCAATGGGGGCCATCAACAGCA
                              911                                                                    980
H5 HA (CK-Indonesia-03)(911)  GTATGCCATTCCACAACATACACCCTCTCACCATCGGGGAATGCCCCAAATATGTGAAATCAAACAGATT
       Synthetic H5 HA(911)  GCATGCCATTCCACAACATCCACCCTCTGACCATCGCGGGAATGCCCCAAATACGTGAAAAGCAACAGACT
                              981                                                                    1050
H5 HA (CK-Indonesia-03)(981)  AGTCCTTGCGACTGGGCTCAGAAATAGCCCTCAAAGAGAGACAAGAGGACTATTTGGAGCTATAGCAGGT
       Synthetic H5 HA(981)  GGTGCTGGCCACCGGGCTGAGAAACAGCCCTCAGAGAGAGACCAGAGGACTGTTTGGAGCCATCGCCGGC
                              1051                                                                   1120
H5 HA (CK-Indonesia-03)(1051) TTTATAGAGGGAGGATGGCAGGGAATGGTAGATGGTTGGTATGGGTACCACCATAGCAATGAGCAGGGGA
       Synthetic H5 HA(1051) TTTATCGAGGGAGGATGGCAGGGAATGGTGGATGGCTGGTACGGATACCACCACAGCAACGAGCAGGGGA
                              1121                                                                   1190
H5 HA (CK-Indonesia-03)(1121) GTGGGTACGCTGCAGACAAAGAATCCACTCAAAAGGCAATACATGGGGTCACCAATAAGGTCAACTCGAT
       Synthetic H5 HA(1121) GCGGATACGCCGCCGACAAAGAATCCACCCAGAAGGCCATCGACGGCGTGACCAACAAAGTGAACAGCAT
```

FIGURE 7 (2/2)

```
                              1191                                                            1260
H5 HA (CK-Indonesia-03) (1191) CATTGACAAAATGAACACTCAGTTTGAGGCCGTTGGAAGGGAATTTAATAACTTAGAAAGGAGAATAGAG
       Synthetic H5 HA  (1191) CATCGACAAAATGAACACCCAGTTTGAGGCCGTGGGAAGGGAGTTTAACAACCTGGAAAGGAGAATCGAG
                              1261                                                            1330
H5 HA (CK-Indonesia-03) (1261) AATTTAAACAAGAAGATGGAAGACGGATTCCTAGATGTCTGGACTTATAATGCTGAACTTCTGGTTCTCA
       Synthetic H5 HA  (1261) AACCTGAACAAGAAGATGGAGGACGGATTCCTGGATGTGTGGACCTACAACGCCGAACTGCTGGTGCTGA
                              1331                                                            1400
H5 HA (CK-Indonesia-03) (1331) TGGAAAATGAGAGAACTCTAGACTTTCATGACTCAAATGTTAAGAACCTCTACGACAAGGTCCGACTACA
       Synthetic H5 HA  (1331) TGGAAAACGAGAGAACCCTGGACTTTCACGACAGCAACGTGAAGAACCTGTACGACAAAGTGAGGCTGCA
                              1401                                                            1470
H5 HA (CK-Indonesia-03) (1401) GCTTAGGGATAATGCAAAGGAGCTGGGTAACGGTTGTTTCGAGTTCTATCACAAATGTGATAATGAATGT
       Synthetic H5 HA  (1401) GCTGAGGGATAACGCCAAGGAGCTGGGCAACGGCTGCTTCGAGTTCTACCACAAATGCGATAACGAATGC
                              1471                                                            1540
H5 HA (CK-Indonesia-03) (1471) ATGGAAAGTATAAGAAACGGAACGTATAACTACCCGCAGTATTCAGAAGAAGCAAGATTAAAAAGAGAAG
       Synthetic H5 HA  (1471) ATGGAAAGCATCAGAAACGGAACCTACAACTACCCCCAGTACAGCGAAGAAGCCAGACTGAAAAGAGAAG
                              1541                                                            1610
H5 HA (CK-Indonesia-03) (1541) AAATAAGTGGAGTAAAATTGGAATCAATAGGAACTTACCAAATACTGTCAATTTATTCAACAGTGGCGAG
       Synthetic H5 HA  (1541) AAATCTCCGGAGTGAAACTGGAATCCATCGGAACCTACCAGATCCTGAGCATCTACAGCACAGTGGCCTC
                              1611                                                            1680
H5 HA (CK-Indonesia-03) (1611) TTCCCTAGCACTGGCAATCATGATGGCTGGTCTATCTTTATGGATGTGCTCCAATGGATCGTTACAATGC
       Synthetic H5 HA  (1611) CTCCCTGGCCCTGGCCATCATGATGGCCGGACTGAGCCTGTGGATGTGCTCCAACGGAAGCCTGCAGTGC
                              1681      1692
H5 HA (CK-Indonesia-03) (1681) AGAATTTGCATT
       Synthetic H5 HA  (1681) AGAATCTGCATC
```

FIGURE 8

|  |  | 1 | 50 |
|---|---|---|---|
| Syn H5 HA w/o cleavage site | (1) | MEKIVLLLAIVSLVKSDQICIGYHANNSTEQVDTIMEKNVTVTHAQDILE | |
| H5 HA (CK-Indonesia-03) | (1) | MEKIVLLLAIVSLVKSDQICIGYHANNSTEQVDTIMEKNVTVTHAQDILE | |
|  |  | 51 | 100 |
| Syn H5 HA w/o cleavage site | (51) | KTHNGKLCDLDGVKPLILRDCSVAGWLLGNPMCDEFINVPEWSYIVEKAN | |
| H5 HA (CK-Indonesia-03) | (51) | KTHNGKLCDLDGVKPLILRDCSVAGWLLGNPMCDEFINVPEWSYIVEKAN | |
|  |  | 101 | 150 |
| Syn H5 HA w/o cleavage site | (101) | PANDLCYPGNLNDYEELKHLLSRINHFEKIQIIPKSSWSDHEASSGVSSA | |
| H5 HA (CK-Indonesia-03) | (101) | PANDLCYPGNLNDYEELKHLLSRINHFEKIQIIPKSSWSDHEASSGVSSA | |
|  |  | 151 | 200 |
| Syn H5 HA w/o cleavage site | (151) | CPYQGKSSFFRNVVWLIKKNSAYPTIKRSYNNTNQEDLLVLWGIHHPNDA | |
| H5 HA (CK-Indonesia-03) | (151) | CPYQGKSSFFRNVVWLIKKNSAYPTIKRSYNNTNQEDLLVLWGIHHPNDA | |
|  |  | 201 | 250 |
| Syn H5 HA w/o cleavage site | (201) | AEQTRLYQNPTTYISVGTSTLNQRLVPKIAIRSKVNGCSGRMEFFWTILK | |
| H5 HA (CK-Indonesia-03) | (201) | AEQTRLYQNPTTYISVGTSTLNQRLVPKIAIRSKVNGCSGRMEFFWTILK | |
|  |  | 251 | 300 |
| Syn H5 HA w/o cleavage site | (251) | PNDAINFESNGNFIAPEYAYKIVKKGDSAIMKSELEYGNCNTKCQTPMGA | |
| H5 HA (CK-Indonesia-03) | (251) | PNDAINFESNGNFIAPEYAYKIVKKGDSATMKSELEYGNCNTKCQTPMGA | |
|  |  | 301 | 350 |
| Syn H5 HA w/o cleavage site | (301) | INSSMPFHNIHPLTIGECPKYVKSNRLVLATGLRNSPQRE----TRGLFG | |
| H5 HA (CK-Indonesia-03) | (301) | INSSMPFHNIHPLTICECPKYVKSNRLVLATGLRNSPQRERRRKKRGLFG | |
|  |  | 351 | 400 |
| Syn H5 HA w/o cleavage site | (347) | AIAGFIEGGWQGMVDGWYGYHHSNEQGSGYAADKESTQKAIDGVTNKVNS | |
| H5 HA (CK-Indonesia-03) | (351) | AIAGFIEGGWQGMVDGWYGYHHSNEQGSGYAADKESTQKAIDGVTNKVNS | |
|  |  | 401 | 450 |
| Syn H5 HA w/o cleavage site | (397) | IIDKMNTQFEAVGREFNNLERRIENLNKKMEDGFLDVWTYNAELLVLMEN | |
| H5 HA (CK-Indonesia-03) | (401) | IIDKMNTQFEAVGREFNNLERRIENLNKKMEDGFLDVWTYNAELLVLMEN | |
|  |  | 451 | 500 |
| Syn H5 HA w/o cleavage site | (447) | ERTLDFHDSNVKNLYDKVRLQLRDNAKELGNGCFEFYHKCDNECMESIRN | |
| H5 HA (CK-Indonesia-03) | (451) | ERTLDFHDSNVKNLYDKVRLQLRDNAKELGNGCFEFYHKCDNECMESIRN | |
|  |  | 501 | 550 |
| Syn H5 HA w/o cleavage site | (497) | GTYNYPQYSEEARLKREEISGVKLESIGTYQILSIYSTVASSLALAIMMA | |
| H5 HA (CK-Indonesia-03) | (501) | GTYNYPQYSEEARLKREEISGVKLESIGTYQILSIYSTVASSLALAIMMA | |
|  |  | 551 | 569 |
| Syn H5 HA w/o cleavage site | (547) | GLSLWMCSNGSLQCRICI- | |
| H5 HA (CK-Indonesia-03) | (551) | GLSLWMCSNGSLQCRICI- | |

FIGURE 9

FIGURE 10 pALVAC C5 H6p-AIV syn H5 HA w/o cleavage site (pLH1852.5)
6551 bp

- C5R
- AmpR
- H6p
- EcoRV (1984)
- AIV synthetic H5 without cleavage site
- C5L
- SpeI (3716)

FIGURE 11

Lane 1. ALVAC-1 digested with *BamH I*
Lane 2: vCP2241.4.1.1.1 digested with *BamH I*
Lane 3: ALVAC-1 digested with *Hind III*
Lane 4: vCP2241.4.1.1.1 digested with *Hind III*
Lane 5: ALVAC-1 digested with *Pst I*
Lane 6: vCP2241.4.1.1.1 digested with *Pst I*
M: *1 KB plus DNA ladder:* 12.0, 11.0, 10.0, 9.0, 8.0, 7.0, 6.0, 5.0, 4.0, 3.0, 2.0, 1.65, 1.0, 0.85 Kb

FIGURE 15

Lane 1: vCP2241.4.1.1.1 cell pellet
Lane 2: vFP2211.4.1.1.1 cell pellet
Lane 3: Fowlpox cell pellet
Lane 4: ALVAC cell pellet
Lane 5: vCP2241.4.1.1.1 supernatant
Lane 6: vFP2211.4.1.1.1 supernatant
Lane 7: Fowlpox supernatant
Lane 8: ALVAC supernatant ← AIV syn H5 HA Primary antibody: HA specific chicken polyclonal antiserum 1:2000

ALVAC vCP2241

Primary antibody: HA-specific chicken polyclonal antiserum 1:1000

SEQUENCE LISTING

<160> NUMBER OF SEQ ID NOS: 24

<210> SEQ ID NO 1
<211> LENGTH: 3659
<212> TYPE: DNA
<213> ORGANISM: Fowlpox virus -continued

```
gatatctgtg gtctatatat actacaccct accgatatta accaacgagt tctcacaag      60 aaaacttgtt tagtagatag agattctttg attgtgttta aaagaagtac cagtaaaaag    120
tgtggcatat gcatagaaga aataaacaaa aacatatttt ccgaacagta ttttggaatt    180
ctcccaagtt gtaaacatat ttttttgccta tcatgtataa gacgttgggc agatactacc   240
agaaatacag atactgaaaa tacgtgtcct gaatgtagaa tagttttcc tttcataata     300 cccagtaggt attggataga taataaatat gataaaaaaa tattatataa tagatataag    360
aaaatgattt ttacaaaaat acctataaga acaataaaaa tataattaca tttacggaaa   420
atagctggtt ttagtttacc aacttagagt aattatcata ttgaatctat attgtttttt   480
agttatataa aaacatgatt agcccccaat cggatgaaaa tataaaagat gttgagaatt   540
tcgaatacaa caaaagagg aatcgtacgt tgtccatatc caaacatata aataaaaatt    600
caaaagtagt attatactgg atgtttagag atcaacgtgt acaagataat tgggctttaa   660
tttacgcaca acgattagcg ttaaaactca aaatacctct aagaatatgc ttttgtgtcg   720
tgccaaaatt tcacactact acttctagac actttatgtt tttaatatcc ggtcttaaag   780
aagtcgcgga agaatgtaaa agactatgta tagggttttc attgatatat ggcgtaccaa   840
aagtaataat tccgtgtata gtaaaaaaat acagagtcgg agtaatcata acggatttct   900
ttccattacg tgttcccgaa agattaatga aacagactgt aatatctctt ccagataaca   960
taccttttat acaagtagac gctcataata tagtaccttg ttgggaagct tctgataaag  1020
aagaatacgg tgcacgaact ttaagaaaaa agatatttga taaattatat gaatatatga  1080
cagaatttcc tgttgttcgt aaacatccat acggtccatt ttctatatct attgcaaaac  1140
ccaaaaatat atcattagac aagacggtat tacccgtaaa atgggcaacg cctggaacaa  1200
aagctggaat aattgtttta aaagaattta taaaaaacag attaccgtca tacgacgcgg  1260
atcataacaa tcctacgtgt gacgctttga gtaacttatc tccgtggcta cattttggtc  1320
atgtatccgc acaacgtgtt gccttagaag tattaaaatg tatacgagaa agcaaaaaaa  1380
acgttgaaac gtttatagat gaaataattg taagaagaga actatcggat aattttttgtt  1440 actataacaa acattatgat agtatccagt ctactcattc atgggttaga aaaacattag  1500
aagatcacat taatgatcct agaaagtata tatattccat taaacaactc gaaaaagcgg  1560
aaactcatga tcctctatgg aacgcgtcac aaatgcagat ggtgagagaa ggaaaaatgc  1620
atagtttttt acgaatgtat tgggctaaga agatacttga atggactaga acacctgaag  1680
acgctttgag ttatagtatc tatttgaaca acaagtacga actagacggc acggatccta  1740
acggatacgt aggttgtatg tggtctattt gcggattaca cgatagagcg tggaaagcaa  1800
gaccgatatt tggaaagata agatatatga attatgagag ttctaagaag aaatttgatg  1860
ttgctgtatt tatacagaaa tacaattaag ataaataata tacagcattg taaccatcgt  1920
catccgttat acgggaata atattaccat acagtattat taaattttct tacgaagaat  1980
atagatcggt atttatcgtt agtttatttt acatttatta attaaacatg tctactatta  2040
cctgttatgg aaatgacaaa tttagttata taatttatga taaaattaag ataataataa  2100
tgaaatcaaa taattatgta aatgctacta gattatgtga attacgagga agaaagttta  2160
cgaactggaa aaaattaagt gaatctaaaa tattagtcga taatgtaaaa aaaataaatg  2220
ataaaactaa ccagttaaaa acggatatga ttatatacgt taaggatatt gatcataaag  2280
gaagagatac ttgcggttac tatgtacacc aagatctggt atcttctata tcaaattgga  2340
tatctccgtt attcgccgtt aaggtaaata aaattattaa ctattatata tgtaatgaat  2400
```

-continued

```
atgatatacg acttagcgaa atggaatctg atatgacaga agtaatagat gtagttgata    2460
aattagtagg aggatacaat gatgaaatag cagaaatat atatttgttt aataaattta    2520
tagaaaaata tattgctaac atatcgttat caactgaatt atctagtata ttaaataatt    2580
ttataaattt tataaatttt aataaaaaat acaataacga cataaagata tttaatcttt    2640
aattcttgat ctgaaaaaca catctataaa actagataaa aagttattcg ataaagataa    2700
taatgaatcg aacgatgaaa aattggaaac agaagttgat aagctaattt ttttcatcta    2760
aatagtatta ttttattgaa gtacgaagtt ttacgttaga taaataataa aggtcgattt    2820
ttactttgtt aaatatcaaa tatgtcatta tctgataaag atacaaaaac acacggtgat    2880
tatcaaccat ctaacgaaca gatattacaa aaaatacgtc ggactatgga aaacgaagct    2940
gatagcctca atagaagaag cattaaagaa attgttgtag atgttatgaa gaattgggat    3000
catcctcaac gaagaaatag ataaagttct aaactggaaa aatgatacat taaacgattt    3060
agatcatcta aatacagatg ataatattaa ggaaatcata caatgtctga ttagagaatt    3120
tgcgtttaaa aagatcaatt ctattatgta tagttatgct atggtaaaac tcaattcaga    3180
taacgaacat tgaaagataa aattaaggat tattttatag aaactattct aaagacaaa    3240 cgtggttata aacaaaagcc attacccgga ttggaaacta aaatactaga tagtattata    3300
agattttaaa aacataaaat taataggttt ttatagattg acttattata tacaatatgg    3360
ataaaagata tatcaact agaaagttga atgacggatt cttaattta tattatgatt    3420 caatagaaat tattgtcatg tcgtgtaatc attttataaa tatatcagcg ttactagcta    3480
agaaaaacaa ggactttaat gaatggctaa agatagaatc atttagagaa ataatagata    3540
ctttagataa aattaattac gatctaggac aacgatattg tgaagaactt acggcgcatc    3600
acattccagt gtaattattg aggtcaaagc tagtaactta atagatgaca ggacagctg    3659
```

```
<210> SEQ ID NO 2
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctagacactt tatgtttttt aatatccggt cttaaaagct tcccggggat ccttatacgg    60
ggaataat                                                             68

<210> SEQ ID NO 3
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
attattcccc gtataaggat cccccgggaa gcttttaaga ccggatatta aaaaacataa    60
agtgt                                                                65

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 4
tcattatcgc gatatccgtg ttaactagct agctaattt tattcccggg atccttatca    60

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtataaggat cccgggaata aaaattagct agctagttaa cacggatatc gcgataatga    60

<210> SEQ ID NO 6
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gaaaaattta aagtcgacct gttttgttga gttgtttgcg tggtaaccaa tgcaaatctg    60
gtcact                                                              66

<210> SEQ ID NO 7
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tctagcaaga ctgactattg caaaagaag cactatttcc tccattacga tacaaactta    60
acggat                                                              66

<210> SEQ ID NO 8
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atccgttaag tttgtatcgt aatggaggaa atagtgcttc ttttgcaat agtcagtctt    60 gctagaagtg accagatttg cattggt                                       87

<210> SEQ ID NO 9
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
taccacgcaa acaactcaac aaaacaggtc gactttaaat ttttctgca               49

<210> SEQ ID NO 10
<211> LENGTH: 21
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 10
acgaagccag cagcggagtg a                                            21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcagcaccag cagttcggcg t                                            21

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtagtgatca aaatacagaa ccat                                         24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gaatccgtca ttcaactttc tagt                                         24

<210> SEQ ID NO 14
<211> LENGTH: 4737
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 14
gaccctttac aagaataaaa gaagaaacaa ctgtgaaata gtttataaat gtaattcgta    60
tgcagaaaac gataatatat tttggtatga gaaatctaaa ggagacatag tttgtataga   120
catgcgctct tccgatgaga tattcgatgc ttttctaatg tatcatatag ctacaagata   180
tgcctatcat gatgatgata tatctacaa aatagtgtta tattattcta ataatcaaaa    240
tgttatatct tatattacga aaaataaata cgttaagtat ataagaaata aaactagaga   300
cgatattcat aaagtaaaaa tattagctct agaagacttt acaacggaag aaatatattg   360
ttggattagt aatatataac agcgtagctg cacggttttg atcattttcc aacaatataa   420
accaatgaag gaggacgact catcaaacat aaataacatt cacggaaaat attcagtatc   480
agatttatca caagatgatt atgttattga atgtatagac ggatctttg attcgatcaa    540 gtatagagat ataaaggtta taataatgaa gaataacggt tacgttaatt gtagtaaatt   600
atgtaaaatg cggaataaat acttttctag atggttgcgt ctttctactt ctaaagcatt   660

```
attagacatt tacaataata agtcagtaga taatgctatt gttaaagtct atggtaaagg    720
taagaaactt attataacag gattttatct caaacaaaat atgatacgtt atgttattga    780
gtggataggg gatgatttta caaacgatat atacaaaatg attaatttct ataatgcgtt    840
attcggtaac gatgaattaa aaatagtatc ctgtgaaaac actctatgcc cgtttataga    900
acttggtaga tgctattatg gtaaaaaatg taagtatata cacggagatc aatgtgatat    960
ctgtggtcta tatatactac accctaccga tattaaccaa cgagtttctc acaagaaaac   1020
ttgtttagta gatagagatt ctttgattgt gtttaaaaga agtaccagta aaaagtgtgg   1080
catatgcata gaagaaataa acaaaaaaca tatttccgaa cagtattttg gaattctccc   1140
aagttgtaaa catattttt gcctatcatg tataagacgt tgggcagata ctaccagaaa   1200
tacagatact gaaaatacgt gtcctgaatg tagaatagtt tttcctttca taatacccag   1260
taggtattgg atagataata aatatgataa aaaaatatta tataatagat ataagaaaat   1320
gatttttaca aaaataccta taagaacaat aaaaatataa ttacatttac ggaaaatagc   1380
tggttttagt ttaccaactt agagtaatta tcatattgaa tctatattgc taattagcta   1440
ataaaaaccc gggttaatta attagtcatc aggcagggcg agaacgagac tatctgctcg   1500
ttaattaatt agagcttctt tattctatac ttaaaaagtg aaaataaata caaaggttct   1560
tgagggttgt gttaaattga aagcgagaaa taatcataaa ttatttcatt atcgcgatat   1620
ccgttaagtt tgtatcgtaa tggagaaaat cgtgctgctg ctggccatcg tgagcctggt   1680
gaaaagcgat cagatctgca tcggctacca cgccaacaac agcacagagc aagtggacac   1740
aatcatggaa aagaacgtga ccgtgacaca cgcccaggac atcctggaaa agacacacaa   1800
cgggaagctg tgcgatctgg atggagtgaa gcctctgatc ctgagagatt gcagcgtggc   1860
cggatggctg ctggggaacc caatgtgcga cgaattcatc aacgtgcccg aatggagcta   1920
catcgtggag aaggccaacc cagccaacga cctgtgctac ccagggaacc tgaacgacta   1980
cgaagaactg aaacacctgc tgagcagaat caaccacttt gagaaaatcc agatcatccc   2040
caaaagcagc tggtccgatc acgaagccag cagcggagtg agcagcgcct gcccatacca   2100
gggaaagtcc agcttttta gaaacgtggt gtggctgatc aaaaagaaca gcgcctaccc   2160
aacaatcaag agaagctaca acaacaccaa ccaggaagat ctgctggtgc tgtgggggat   2220
ccaccaccct aacgatgccg ccgagcagac aaggctgtac cagaacccaa ccacctacat   2280
ctccgtgggg acaagcacac tgaaccgaga actggtgcca aaaatcgcca tcagatccaa   2340
agtgaacggg cagagcggaa gaatggagtt cttctggaca atcctgaaac ccaacgatgc   2400
catcaacttc gagagcaacg gaaacttcat cgccccagaa tacgcctaca aaatcgtgaa   2460
gaaaggggac agcgccatca tgaaaagcga actggaatac ggcaactgca acaccaagtg   2520 ccagaccca tgggggcca tcaacagcag catgccattc cacaacatcc accctctgac   2580
catcggggaa tgccccaaat acgtgaaaag caacagactg gtgctggcca ccgggctgag   2640
aaacagccct cagagagaga ccagaggact gtttggagcc atcgccggct ttatcgaggg   2700
aggatggcag ggaatggtgg atggctggta cggataccac cacagcaacg agcagggag   2760 cggatacgcc gccgcaaaag aatccaccca gaaggccatc gacggcgtga ccaacaaagt   2820
gaacagcatc atcgacaaaa tgaacaccca gtttgaggcc gtgggaaggg agtttaacaa   2880
cctggaaagg agaatcgaga acctgaacaa gaagatggag gacggattcc tggatgtgtg   2940
gacctacaac gccgaactgc tggtgctgat ggaaaacgag agaaccctgg actttcacga   3000
cagcaacgtg aagaacctgt acgacaaagt gaggctgcag ctgagggata cgccaagga   3060
```

```
gctgggcaac ggctgcttcg agttctacca caaatgcgat aacgaatgca tggaaagcat    3120
cagaaacgga acctacaact accccccagta cagcgaagaa gccagactga aaagagaaga    3180
aatctccgga gtgaaactgg aatccatcgg aacctaccag atcctgagca tctacagcac    3240
agtggcctcc tccctggccc tggccatcat gatggccgga ctgagcctgt ggatgtgctc    3300
caacggaagc ctgcagtgca gaatctgcat ctgactcgag ttttttattga ctagttaatc    3360 ataagataaa taatatacag cattgtaacc atcgtcatcc gttatacggg gaataatatt    3420
accatacagt attattaaat tttcttacga agaatataga tcggtatta tcgttagttt    3480 attttacatt tattaattaa acatgtctac tattacctgt tatggaaatg acaaatttag    3540
ttatataatt tatgataaaa ttaagataat aataatgaaa tcaaataatt atgtaaatgc    3600
tactagatta tgtgaattac gaggaagaaa gtttacgaac tggaaaaaat taagtgaatc    3660
taaaatatta gtcgataatg taaaaaaaat aaatgataaa actaaccagt taaaaacgga    3720
tatgattata tacgttaagg atattgatca taaaggaaga gatacttgcg gttactatgt    3780
acaccaagat ctggtatctt ctatatcaaa ttggatatct ccgttattcg ccgttaaggt    3840
aaataaaatt attaactatt atatatgtaa tgaatatgat atacgactta gcgaaatgga    3900
atctgatatg acagaagtaa tagatgtagt tgataaatta gtaggaggat acaatgatga    3960
aatagcagaa ataatatatt tgtttaataa atttatagaa aaatatattg ctaacatatc    4020
gttatcaact gaattatcta gtatattaaa taattttata aattttaata aaaaatacaa    4080
taacgacata aaagatatta aatctttaat tcttgatctg aaaaacacat ctataaaact    4140
agataaaaag ttattcgata aagataataa tgaatcgaac gatgaaaaat tggaaacaga    4200
agttgataag ctaattttttt tcatctaaat agtattattt tattgaagta cgaagttta    4260 cgttagataa ataataaagg tcgattttta ttttgttaaa tatcaaatat gtcattatct    4320
gataaagata caaaaacaca cggtgattat caaccatcta acgaacagat attacaaaaa    4380
atacgtcgga ctatggaaaa cgaagctgat agcctcaata gaagaagcat taagaaatt    4440 gttgtagatg ttatgaagaa ttgggatcat cctctcaacg aagaaataga taagttcta    4500 aactggaaaa atgatacatt aaacgattta gatcatctaa atacagatga taatatttaag    4560 gaaatcatac aatgtctgat tagagaattt gcgttaaaaa gatcaattc tattatgtat    4620 agttatgcta tggtaaaact caattcagat aacgaaacat tgaaagataa aattaaggat    4680
tattttatag aaactattct taagacaaa cgtggttata acaaaagcc attccc        4737
```

<210> SEQ ID NO 15
<211> LENGTH: 1692
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 15

```
atggagaaaa tcgtgctgct gctggccatc gtgagcctgg tgaaaagcga tcagatctgc     60
atcggctacc acgccaacaa cagcacagag caagtggaca caatcatgga aaagaacgtg    120
accgtgacac acgcccagga catcctggaa aagacacaca cgggaagct gtgcgatctg    180 gatggagtga agcctctgat cctgagagat tgcagcgtgg ccggatggct gctggggaac    240
ccaatgtgcg acgaattcat caacgtgccc gaatggagct acatcgtgga aaggccaac    300 ccagccaacg acctgtgcta cccagggaac ctgaacgact acgaagaact gaaacacctg    360
```

```
ctgagcagaa tcaaccactt tgagaaaatc cagatcatcc ccaaaagcag ctggtccgat    420
cacgaagcca gcagcggagt gagcagcgcc tgcccatacc agggaaagtc cagctttttt    480
agaaacgtgg tgtggctgat caaaaagaac agcgcctacc aacaatcaa gagaagctac     540 aacaaccaca accaggaaga tctgctggtg ctgtggggga tccaccaccc taacgatgcc    600
gccgagcaga caaggctgta ccagaaccca accacctaca tctccgtggg gacaagcaca    660
ctgaaccaga gactggtgcc aaaaatcgcc atcagatcca agtgaacgg gcagagcgga     720 agaatggagt tcttctggac aatcctgaaa cccaacgatg ccatcaactt cgagagcaac    780
ggaaacttca tcgccccaga atacgcctac aaaatcgtga agaaagggga cagcgccatc    840
atgaaaagcg aactggaata cggcaactgc aacaccaagt gccagacccc aatggggggcc   900 atcaacagca gcatgccatt ccacaacatc caccctctga ccatcgggga atgccccaaa    960
tacgtgaaaa gcaacagact ggtgctggcc accgggctga aaacagccc tcagagagag    1020 accagaggac tgtttggagc catcgccggc tttatcgagg aggatggca gggaatggtg    1080 gatggctggt acggatacca ccacagcaac gagcagggga gcggatacgc cgccgacaaa   1140
gaatccaccc agaaggccat cgacggcgtg accaacaaag tgaacagcat catcgacaaa   1200
atgaacaccc agtttgaggc cgtgggaagg gagtttaaca acctggaaag gagaatcgag   1260
aacctgaaca gaagatgga ggacggattc ctggatgtgt ggacctacaa cgccgaactg   1320
ctggtgctga tggaaaacga gagaacctg gactttcacg acagcaacgt gaagaacctg    1380
tacgacaaag tgaggctgca gctgagggat aacgccaagg agctgggcaa cggctgcttc   1440
gagttctacc acaaatgcga taacgaatgc atggaaagca tcagaaacgg aacctacaac   1500
tacccccagt acagcgaaga agccagactg aaaagagaag aaatctccgg agtgaaactg   1560
gaatccatcg gaacctacca gatcctgagc atctacagca cagtggcctc ctccctggcc   1620
ctggccatca tgatggccgg actgagcctg tggatgtgct ccaacggaag cctgcagtgc    1680
agaatctgca tc                                                       1692
```

<210> SEQ ID NO 16
<211> LENGTH: 564
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 16

```
Met Glu Lys Ile Val Leu Leu Leu Ala Ile Val Ser Leu Val Lys Ser
 1               5                  10                  15

Asp Gln Ile Cys Ile Gly Tyr His Ala Asn Asn Ser Thr Glu Gln Val
             20                  25                  30

Asp Thr Ile Met Glu Lys Asn Val Thr Val Thr His Ala Gln Asp Ile
         35                  40                  45

Leu Glu Lys Thr His Asn Gly Lys Leu Cys Asp Leu Asp Gly Val Lys
     50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Asn Pro Ala Asn Asp Leu Cys Tyr Pro Gly Asn Leu Asn
            100                 105                 110

Asp Tyr Glu Glu Leu Lys His Leu Leu Ser Arg Ile Asn His Phe Glu
        115                 120                 125
```

-continued

```
Lys Ile Gln Ile Ile Pro Lys Ser Ser Trp Ser Asp His Glu Ala Ser
    130                 135                 140
Ser Gly Val Ser Ser Ala Cys Pro Tyr Gln Gly Lys Ser Ser Phe Phe
145                 150                 155                 160
Arg Asn Val Val Trp Leu Ile Lys Lys Asn Ser Ala Tyr Pro Thr Ile
                165                 170                 175
Lys Arg Ser Tyr Asn Asn Thr Asn Gln Glu Asp Leu Leu Val Leu Trp
            180                 185                 190
Gly Ile His His Pro Asn Asp Ala Ala Glu Gln Thr Arg Leu Tyr Gln
        195                 200                 205
Asn Pro Thr Thr Tyr Ile Ser Val Gly Thr Ser Thr Leu Asn Gln Arg
    210                 215                 220
Leu Val Pro Lys Ile Ala Ile Arg Ser Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
            260                 265                 270
Val Lys Lys Gly Asp Ser Ala Ile Met Lys Ser Glu Leu Glu Tyr Gly
        275                 280                 285
Asn Cys Asn Thr Lys Cys Gln Thr Pro Met Gly Ala Ile Asn Ser Ser
    290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Arg Glu Thr Arg Gly Leu Phe Gly Ala Ile Ala Gly Phe Ile
            340                 345                 350
Glu Gly Gly Trp Gln Gly Met Val Asp Gly Trp Tyr Gly Tyr His His
        355                 360                 365
Ser Asn Glu Gln Gly Ser Gly Tyr Ala Ala Asp Lys Glu Ser Thr Gln
    370                 375                 380
Lys Ala Ile Asp Gly Val Thr Asn Lys Val Asn Ser Ile Ile Asp Lys
385                 390                 395                 400
Met Asn Thr Gln Phe Glu Ala Val Gly Arg Glu Phe Asn Asn Leu Glu
                405                 410                 415
Arg Arg Ile Glu Asn Leu Asn Lys Lys Met Glu Asp Gly Phe Leu Asp
            420                 425                 430
Val Trp Thr Tyr Asn Ala Glu Leu Leu Val Leu Met Glu Asn Glu Arg
        435                 440                 445
Thr Leu Asp Phe His Asp Ser Asn Val Lys Asn Leu Tyr Asp Lys Val
    450                 455                 460
Arg Leu Gln Leu Arg Asp Asn Ala Lys Glu Leu Gly Asn Gly Cys Phe
465                 470                 475                 480
Glu Phe Tyr His Lys Cys Asp Asn Glu Cys Met Glu Ser Ile Arg Asn
                485                 490                 495
Gly Thr Tyr Asn Tyr Pro Gln Tyr Ser Glu Glu Ala Arg Leu Lys Arg
            500                 505                 510
Glu Glu Ile Ser Gly Val Lys Leu Glu Ser Ile Gly Thr Tyr Gln Ile
        515                 520                 525
Leu Ser Ile Tyr Ser Thr Val Ala Ser Ser Leu Ala Leu Ala Ile Met
    530                 535                 540
Met Ala Gly Leu Ser Leu Trp Met Cys Ser Asn Gly Ser Leu Gln Cys
```

```
                         545                 550                 555                 560
Arg Ile Cys Ile

<210> SEQ ID NO 17
<211> LENGTH: 564
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 17

Met Glu Lys Ile Val Leu Leu Leu Ala Ile Val Ser Leu Val Lys Ser
 1               5                  10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Leu Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Lys Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Ile Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350
```

```
Glu Gly Gly Trp Gln Gly Met Val Asp Gly Trp Tyr Gly Tyr His His
        355                 360                 365
Ser Asn Glu Gln Gly Ser Gly Tyr Ala Ala Asp Lys Glu Ser Thr Gln
        370                 375                 380
Lys Ala Ile Asp Gly Val Thr Asn Lys Val Asn Ser Ile Ile Asp Lys
385                 390                 395                 400
Met Asn Thr Gln Phe Glu Ala Val Gly Arg Glu Phe Asn Asn Leu Glu
                405                 410                 415
Arg Arg Ile Glu Asn Leu Asn Lys Lys Met Glu Asp Gly Phe Leu Asp
                420                 425                 430
Val Trp Thr Tyr Asn Ala Glu Leu Leu Val Leu Met Glu Asn Glu Arg
                435                 440                 445
Thr Leu Asp Phe His Asp Ser Asn Val Lys Asn Leu Tyr Asp Lys Val
        450                 455                 460
Arg Leu Gln Leu Arg Asp Asn Ala Lys Glu Leu Gly Asn Gly Cys Phe
465                 470                 475                 480
Glu Phe Tyr His Lys Cys Asp Asn Glu Cys Met Glu Ser Ile Arg Asn
                485                 490                 495
Gly Thr Tyr Asn Tyr Pro Gln Tyr Ser Glu Glu Ala Arg Leu Lys Arg
                500                 505                 510
Glu Glu Ile Ser Gly Val Lys Leu Glu Ser Ile Gly Thr Tyr Gln Ile
        515                 520                 525
Leu Ser Ile Tyr Ser Thr Val Ala Ser Ser Leu Ala Leu Ala Ile Met
        530                 535                 540
Met Ala Gly Leu Ser Leu Trp Met Cys Ser Asn Gly Ser Leu Gln Cys
545                 550                 555                 560
Arg Ile Cys Ile

<210> SEQ ID NO 18
<211> LENGTH: 4016
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 18
ggaaacagct atgaccatga ttacgaattg cggccgcaat tctgaatgtt aaatgttata      60
ctttggatga agctataaat atgcattgga aaaataatcc atttaaagaa aggattcaaa    120
tactacaaaa cctaagcgat aatatgttaa ctaagcttat tcttaacgac gctttaaata    180
tacacaaata aacataattt ttgtataacc taacaaataa ctaaaacata aaaataataa    240
aaggaaatgt aatatcgtaa ttattttact caggaatggg gttaaatatt tatatcacgt    300
gtatatctat actgttatcg tatactcttt acaattacta ttcgaatat gcaagagata     360 ataagattac gtatttaaga gaatcttgtc atgataattg ggtacgacat agtgataaat    420
gctatttcgc atcgttacat aaagtcagtt ggaaagatgg atttgacaga tgtaacttaa    480
taggtgcaaa aatgttaaat aacagcattc tatcggaaga taggatacca gttatattat    540
acaaaaatca ctggttggat aaaacagatt ctgcaatatt cgtaaaagat gaagattact    600
gcgaatttgt aaactatgac aataaaaagc cattatctc aacgacatcg tgtaattctt      660
ccatgtttta tgtatgtgtt tcagatatta tgagattact ataaactttt tgtatactta    720
tattccgtaa actatattaa tcatgaagaa atgaaaaag tatagaagct gttcacgagc      780
ggttgttgaa acaacaaaa ttatacattc aagatggctt acatatacgt ctgtgaggct       840
```

```
atcatggata atgacaatgc atctctaaat aggttttttgg acaatggatt cgaccctaac      900
acggaatatg gtactctaca atctcctctt gaaatggctg taatgttcaa gaataccgag      960
gctataaaaa tcttgatgag gtatggagct aaacctgtag ttactgaatg cacaacttct     1020
tgtctgcatg atgcggtgtt gagagacgac tacaaaatag tgaaagatct gttgaagaat     1080
aactatgtaa acaatgttct ttacagcgga ggctttactc ctttgtgttt ggcagcttac     1140
cttaacaaag ttaatttggt taaacttcta ttggctcatt cggcggatgt agatatttca     1200
aacacggatc ggttaactcc tctacatata gccgtatcaa ataaaaattt aacaatggtt     1260
aaacttctat tgaacaaagg tgctgatact gacttgctgg ataacatggg acgtactcct     1320
ttaatgatcg ctgtacaatc tggaaatatt tattgtaccc tgcatgagga aattactagc     1380
gacatgttag acctttataa gaaatatgta gcacactact taaaaaaaat aaaatgtcca     1440
gaactgggaa aaattgatct tgccagctgt aattcatggt agaaaagaag tgctcaggct     1500
acttttcaac aaaggagcag atgtaaacta catctttgaa agaaatggaa aatcatatac     1560
tgttttggaa ttgattaaag aaagttactc tgagacacaa aagaggtagc tgaagtggta     1620
ctctcaaagg tacgtgacta attagctata aaaaggatcc gggttaatta attagtcatc     1680
aggcagggcg agaacgagac tatctgctcg ttaattaatt agagcttctt tattctatac     1740
ttaaaaagtg aaaataaata caaaggttct tgagggttgt gttaaattga aagcgagaaa     1800
taatcataaa ttatttcatt atcgcgatat ccgttaagtt tgtatcgtaa tggagaaaat     1860
cgtgctgctg ctggccatcg tgagcctggt gaaaagcgat cagatctgca tcggctacca     1920
cgccaacaac agcacagagc aagtggacac aatcatggaa agaacgtga ccgtgacaca      1980
cgcccaggac atcctggaaa agacacacaa cgggaagctg tgcgatctgg atggagtgaa     2040
gcctctgatc ctgagagatt gcagcgtggc cggatggctg ctggggaacc caatgtgcga     2100
cgaattcatc aacgtgcccg aatggagcta catcgtggag aaggccaacc cagccaacga     2160
cctgtgctac ccagggaacc tgaacgacta cgaagaactg aaacacctgc tgagcagaat     2220
caaccacttt gagaaaatcc agatcatccc caaaagcagc tggtccgatc acgaagccag     2280
cagcggagtg agcagcgcct gcccatacca gggaaagtcc agcttttta gaaacgtggt      2340
gtggctgatc aaaaagaaca cgcctaccc aacaatcaag agaagctaca caacaccaa       2400
ccaggaagat ctgctggtgc tgtggggat ccaccaccct aacgatgccg ccgagcagac       2460
aaggctgtac cagaacccaa ccacctacat ctccgtgggg acaagcacac tgaaccagag     2520
actggtgcca aaaatcgcca tcagatccaa agtgaacggg cagagcggaa gaatggagtt     2580
cttctggaca atcctgaaac ccaacgatgc catcaacttc gagagcaacg gaaacttcat     2640
cgccccagaa tacgcctaca aaatcgtgaa gaaagggac agcgccatca tgaaaagcga      2700
actggaatac ggcaactgca acaccaagtg ccagaccca atgggggcca tcaacagcag      2760
catgccattc cacaacatcc ccctctgac catcgggaa tgccccaaat acgtgaaaag       2820
caacagactg gtgctggcca ccgggctgag aaacagccct cagagagaga ccagaggact     2880
gtttggagcc atcgccggct ttatcgaggg aggatggcag gaatggtgg atggctggta      2940
cggataccac cacagcaacg agcagggag cggatacgcc gccgacaaag aatccaccca      3000
gaaggccatc gacggcgtga ccaacaaagt gaacagcatc atcgacaaaa tgaacaccca     3060
gtttgaggcc gtgggaaggg agtttaacaa cctggaaagg agaatcgaga acctgaacaa     3120
gaagatggag gacggattcc tggatgtgtg gacctacaac gccgaactgc tggtgctgat     3180
ggaaaacgag agaaccctgg actttcacga cagcaacgtg aagaacctgt acgacaaagt     3240
```

-continued

```
gaggctgcag ctgagggata acgccaagga gctgggcaac ggctgcttcg agttctacca    3300
caaatgcgat aacgaatgca tggaaagcat cagaaacgga acctacaact accccccagta   3360 cagcgaagaa gccagactga aaagagaaga aatctccgga gtgaaactgg aatccatcgg    3420
aacctaccag atcctgagca tctacagcac agtggcctcc tccctggccc tggccatcat    3480
gatggccgga ctgagcctgt ggatgtgctc caacggaagc ctgcagtgca gaatctgcat    3540
ctgactcgag ttttttattga ctagttaatc acggccgctt ataaagatct aaaatgcata   3600
atttctaaat aatgaaaaaa agtacatcat gagcaacgcg ttagtatatt ttacaatgga    3660
gattaacgct ctataccgtt ctatgtttat tgattcagat gatgttttag aaaagaaagt    3720
tattgaatat gaaaacttta atgaagatga agatgacgac gatgattatt gttgtaaatc    3780
tgttttagat gaagaagatg acgcgctaaa gtatactatg gttacaaagt ataagtctat    3840
actactaatg gcgacttgtg caagaaggta tagtatagtg aaaatgttgt tagattatga    3900
ttatgaaaaa ccaaataaat cagatccata tctaaaggta tctcctttgc acataatttc    3960
atctattcct agtttagaat acctgcagcc aagcttggca ctggccgtcg ttttac        4016
```

<210> SEQ ID NO 19
<211> LENGTH: 6551
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 19

```
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg aattgcggcc    240
gcaattctga atgttaaatg ttatactttg gatgaagcta aaatatgca ttggaaaaat    300 aatccattta agaaaggat tcaaatacta caaaacctaa gcgataatat gttaactaag    360
cttattctta acgacgcttt aaatatacac aaataaacat aattttttgta taacctaaca   420 aataactaaa acataaaaat aataaaagga atgtaatat cgtaattatt ttactcagga    480
atggggttaa atatttatat cacgtgtata tctatactgt tatcgtatac tctttacaat    540
tactattacg aatatgcaag agataataag attacgtatt taagagaatc ttgtcatgat    600
aattgggtac gacatagtga taaatgctat ttcgcatcgt tacataaagt cagttggaaa    660
gatggatttg acagatgtaa cttaataggt gcaaaaatgt taaataacag cattctatcg    720
gaagatagga taccagttat attatacaaa aatcactggt tggataaaac agattctgca    780
atattcgtaa aagatgaaga ttactgcgaa tttgtaaact atgacaataa aaagccatttt   840 atctcaacga catcgtgtaa ttcttccatg ttttatgtat gtgtttcaga tattatgaga    900
ttactataaa cttttttgtat acttatattc cgtaaactat attaatcatg aagaaaatga    960
aaaagtatag aagctgttca cgagcggttg ttgaaaacaa caaaattata cattcaagat    1020
ggcttacata tacgtctgtg aggctatcat ggataatgac aatgcatctc taaataggtt    1080
tttggacaat ggattcgacc ctaacacgga atatggtact ctacaatctc tccttgaaat    1140
ggctgtaatg ttcaagaata ccgaggctat aaaaatcttg atgaggtatg agctaaacc    1200 tgtagttact gaatgcacaa cttcttgtct gcatgatgcg gtgttgagag acgactacaa    1260
```

```
aatagtgaaa gatctgttga agaataacta tgtaaacaat gttctttaca gcggaggctt   1320
tactcctttg tgtttggcag cttaccttaa caaagttaat ttggttaaac ttctattggc   1380
tcattcggcg gatgtagata tttcaaacac ggatcggtta actcctctac atatagccgt   1440
atcaaataaa aatttaacaa tggttaaact tctattgaac aaaggtgctg atactgactt   1500
gctggataac atgggacgta ctcctttaat gatcgctgta caatctggaa atattgaaat   1560
atgtagcaca ctacttaaaa aaaataaaat gtccagaact gggaaaaatt gatcttgcca   1620
gctgtaattc atggtagaaa agaagtgctc aggctacttt tcaacaaagg agcagatgta   1680
aactacatct ttgaaagaaa tggaaaatca tatactgttt tggaattgat taaagaaagt   1740
tactctgaga cacaaaagag gtagctgaag tggtactctc aaaggtacgt gactaattag   1800
ctataaaaag gatccgggtt aattaattag tcatcaggca gggcgagaac gagactatct   1860
gctcgttaat taattagagc ttcttttattc tatacttaaa aagtgaaaat aaatacaaag   1920
gttcttgagg gttgtgttaa attgaaagcg agaaataatc ataaattatt tcattatcgc   1980
gatatccgtt aagtttgtat cgtaatggag aaaatcgtgc tgctgctggc catcgtgagc   2040
ctggtgaaaa gcgatcagat ctgcatcggc taccacgcca acaacagcac agagcaagtg   2100
gacacaatca tggaaaagaa cgtgaccgtg acacacgccc aggacatcct ggaaaagaca   2160
cacaacggga gctgtgcga tctggatgga gtgaagcctc tgatcctgag agattgcagc   2220
gtggccggat ggctgctggg gaacccaatg tgcgacgaat tcatcaacgt gcccgaatgg   2280
agctacatcg tggagaaggc caacccagcc aacgacctgt gctacccagg gaacctgaac   2340
gactacgaag aactgaaaca cctgctgagc agaatcaacc actttgagaa aatccagatc   2400
atccccaaaa gcagctggtc cgatcacgaa gccagcagcg gagtgagcag cgcctgccca   2460
taccagggaa agtccagctt ttttagaaac gtggtgtggc tgatcaaaaa gaacagcgcc   2520
tacccaacaa tcaagagaag ctacaacaac accaaccagg aagatctgct ggtgctgtgg   2580
gggatccacc accctaacga tgccgccgag cagacaaggc tgtaccagaa cccaaccacc   2640
tacatctccg tggggacaag cacactgaac cagagactgg tgccaaaaat cgccatcaga   2700
tccaaagtga cgggcagag cggaagaatg gagttcttct ggacaatcct gaaacccaac   2760
gatgccatca acttcgagag caacggaaac ttcatcgccc cagaatacgc ctacaaaatc   2820
gtgaagaaag gggacagcgc catcatgaaa agcgaactgg aatacggcaa ctgcaacacc   2880
aagtgccaga ccccaatggg ggccatcaac agcagcatgc cattccacaa catccaccct   2940
ctgaccatcg ggaatgccc caaatacgtg aaaagcaaca gactggtgct ggccaccggg   3000
ctgagaaaca gccctcagag agagaccaga ggactgtttg agccatcgc cggctttatc   3060
gagggaggat ggcagggaat ggtggatggc tggtacggat accaccacag caacgagcag   3120
gggagcggat acgccgccga caaagaatcc acccagaagg ccatcgacgg cgtgaccaac   3180
aaagtgaaca gcatcatcga caaaatgaac acccagtttg aggccgtggg aagggagttt   3240
aacaacctgg aaaggagaat cgagaacctg aacaagaaga tggaggacgg attcctggat   3300
gtgtggacct acaacgccga actgctggtg ctgatggaaa acgagagaac cctggacttt   3360
cacgacagca acgtgaagaa cctgtacgac aaagtgaggc tgcagctgag ggataacgcc   3420
aaggagctgg gcaacggctg cttcgagttc taccacaaat gcgataacga atgcatggaa   3480
agcatcagaa acggaaccta caactacccc cagtacagcg aagaagccag actgaaaaga   3540
gaagaaatct ccgagtgaa actggaatcc atcggaacct accagatcct gagcatctac   3600
agcacagtgg cctcctccct ggccctggcc atcatgatgg ccggactgag cctgtggatg   3660
```

-continued

```
tgctccaacg gaagcctgca gtgcagaatc tgcatctgac tcgagttttt attgactagt    3720
taatcacggc cgcttataaa gatctaaaat gcataatttc taaataatga aaaaagtac    3780
atcatgagca acgcgttagt atattttaca atggagatta acgctctata ccgttctatg    3840
tttattgatt cagatgatgt tttagaaaag aaagttattg aatatgaaaa ctttaatgaa    3900
gatgaagatg acgacgatga ttattgttgt aaatctgttt tagatgaaga agatgacgcg    3960
ctaaagtata ctatggttac aaagtataag tctatactac taatggcgac ttgtgcaaga    4020
aggtatagta tagtgaaaat gttgttagat tatgattatg aaaaaccaaa taaatcagat    4080
ccatatctaa aggtatctcc tttgcacata atttcatcta ttcctagttt agaataacctg    4140
cagccaagct tggcactggc cgtcgtttta acgtcgtg actgggaaaa ccctggcgtt    4200
acccaactta atcgccttgc agcacatccc cctttcgcca gctggcgtaa tagcgaagag    4260
gcccgcaccg atcgcccttc ccaacagttg cgcagcctga atggcgaatg gcgcctgatg    4320
cggtattttc tccttacgca tctgtgcggt atttcacacc gcatatggtg cactctcagt    4380
acaatctgct ctgatgccgc atagttaagc cagccccgac acccgccaac acccgctgac    4440
gcgccctgac gggcttgtct gctcccggca tccgcttaca dacaagctgt gaccgtctcc    4500
gggagctgca tgtgtcagag gttttcaccg tcatcaccga aacgcgcgag acgaaagggc    4560
ctcgtgatac gcctatttt ataggttaat gtcatgataa taatggtttc ttagacgtca    4620
ggtggcactt ttcggggaaa tgtgcgcgga acccctattt gtttattttt ctaaatacat    4680
tcaaatatgt atccgctcat gagacaataa ccctgataaa tgcttcaata atattgaaaa    4740
aggaagagta tgagtattca acatttccgt gtcgccctta ttcccttttt tgcggcattt    4800
tgccttcctg ttttgctca cccagaaacg ctggtgaaag taaaagatgc tgaagatcag    4860
ttgggtgcac gagtgggtta catcgaactg gatctcaaca gcggtaagat ccttgagagt    4920
tttcgccccg aagaacgttt tccaatgatg agcactttta aagttctgct atgtggcgcg    4980
gtattatccc gtattgacgc cgggcaagag caactcggtc gccgcataca ctattctcag    5040
aatgacttgg ttgagtactc accagtcaca gaaaagcatc ttacggatgg catgacagta    5100
agagaattat gcagtgctgc cataaccatg agtgataaca ctgcggccaa cttacttctg    5160
acaacgatcg aggaccgaa ggagctaacc gcttttttgc acaacatggg ggatcatgta    5220
actcgccttg atcgttggga accggagctg aatgaagcca taccaaacga cgagcgtgac    5280
accacgatgc ctgtagcaat ggcaacaacg ttgcgcaaac tattaactgg cgaactactt    5340
actctagctt cccggcaaca attaatagac tggatggagg cggataaagt tgcaggacca    5400
cttctgcgct cggcccttcc ggctggctgg tttattgctg ataaatctgg agccggtgag    5460
cgtgggtctc gcggtatcat tgcagcactg gggccagatg gtaagccctc ccgtatcgta    5520
gttatctaca cgacggggag tcaggcaact atggatgaac gaaatagaca gatcgctgag    5580
ataggtgcct cactgattaa gcattggtaa ctgtcagacc aagtttactc atatatactt    5640
tagattgatt taaaacttca ttttaatttt aaaaggatct aggtgaagat cctttttgat    5700
aatctcatga ccaaaatccc ttaacgtgag ttttcgttcc actgagcgtc agaccccgta    5760
gaaaagatca aggatcttc ttgagatcct ttttttctgc gcgtaatctg ctgcttgcaa    5820
acaaaaaaac caccgctacc agcggtggtt tgtttgccgg atcaagagct accaactctt    5880
tttccgaagg taactggctt cagcagagcg cagataccaa atactgtcct tctagtgtag    5940
ccgtagttag gccaccactt caagaactct gtagcaccgc ctacatacct cgctctgcta    6000
atcctgttac cagtggctgc tgccagtggc gataagtcgt gtcttaccgg gttggactca    6060
```

```
agacgatagt taccggataa ggcgcagcgg tcgggctgaa cgggggggttc gtgcacacag      6120 cccagcttgg agcgaacgac ctacaccgaa ctgagatacc tacagcgtga gctatgagaa      6180
agcgccacgc ttcccgaagg gagaaaggcg gacaggtatc cggtaagcgg cagggtcgga      6240
acaggagagc gcacgaggga gcttccaggg ggaaacgcct ggtatcttta tagtcctgtc      6300
gggtttcgcc acctctgact tgagcgtcga ttttttgtgat gctcgtcagg ggggcggagc      6360
ctatggaaaa acgccagcaa cgcggccttt ttacggttcc tggcctttttg ctggcctttt      6420 gctcacatgt tctttcctgc gttatcccct gattctgtgg ataaccgtat taccgccttt      6480
gagtgagctg ataccgctcg ccgcagccga acgaccgagc gcagcgagtc agtgagcgag      6540
gaagcggaag a                                                           6551

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gaatctgtta gttagttact tggat                                              25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgattatagc tattatcaca gactc                                              25

<210> SEQ ID NO 22
<211> LENGTH: 3890
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 22
tgaatgttaa atgttatact ttggatgaag ctataaatat gcattggaaa aataatccat        60
ttaaagaaag gattcaaata ctacaaaacc taagcgataa tatgttaact aagcttattc       120
ttaacgacgc tttaaatata cacaaataaa cataattttt gtataaccta acaaataact       180
aaaacataaa aataataaaa ggaaatgtaa tatcgtaatt atttactca ggaatggggt        240 taaatattta tatcacgtgt atatctatac tgttatcgta tactctttac aattactatt       300
acgaatatgc aagagataat aagattacgt atttaagaga atcttgtcat gataattggg       360
tacgacatag tgataaatgc tatttcgcat cgttacataa agtcagttgg aaagatggat       420
ttgacagatg taacttaata ggtgcaaaaa tgttaaataa cagcattcta tcggaagata       480
ggataccagt tatattatac aaaaatcact ggttggataa aacagattct gcaatattcg       540
taaaagatga agattactgc gaatttgtaa actatgacaa taaaaagcca tttatctcaa       600
```

```
cgacatcgtg taattcttcc atgttttatg tatgtgtttc agatattatg agattactat    660
aaactttttg tatacttata ttccgtaaac tatattaatc atgaagaaaa tgaaaaagta    720
tagaagctgt tcacgagcgg ttgttgaaaa caacaaaatt atacattcaa gatggcttac    780
atatacgtct gtgaggctat catggataat gacaatgcat ctctaaatag gttttggac     840 aatggattcg accctaacac ggaatatggt actctacaat ctcctcttga atggctgta     900 atgttcaaga ataccgaggc tataaaaatc ttgatgaggt atggagctaa acctgtagtt    960
actgaatgca caacttcttg tctgcatgat gcggtgttga gagacgacta caaaatagtg   1020
aaagatctgt gaagaataa ctatgtaaac aatgttcttt acagcggagg ctttactcct    1080
ttgtgtttgg cagcttacct taacaaagtt aatttggtta aacttctatt ggctcattcg   1140
gcggatgtag atatttcaaa cacgatcgg ttaactcctc tacatatagc cgtatcaaat    1200
aaaaatttaa caatggttaa acttctattg aacaaaggtg ctgatactga cttgctggat   1260
aacatgggac gtactccttt aatgatcgct gtacaatctg gaatattga aatatgtagc    1320 acactactta aaaaaaataa aatgtccaga actgggaaaa attgatcttg ccagctgtaa   1380
ttcatggtag aaaagaagtg ctcaggctac ttttcaacaa aggagcagat gtaaactaca   1440
tctttgaaag aaatggaaaa tcatatactg ttttggaatt gattaaagaa agttactctg   1500
agacacaaaa gaggtagctg aagtggtact ctcaaaggta cgtgactaat tagctataaa   1560
aaggatccgg gttaattaat tagtcatcag gcagggcgag aacgagacta tctgctcgtt   1620
aattaattag agcttcttta ttctatactt aaaaagtgaa aataaataca aaggttcttg   1680
agggttgtgt taaattgaaa gcgagaaata atcataaatt atttcattat cgcgatatcc   1740
gttaagtttg tatcgtaatg gagaaaatcg tgctgctgct ggccatcgtg agcctggtga   1800
aaagcgatca gatctgcatc ggctaccacg ccaacaacag cacagagcaa gtggacacaa   1860
tcatggaaaa gaacgtgacc gtgacacacg cccaggacat cctggaaaag acacacaacg   1920
ggaagctgtg cgatctggat ggagtgaagc ctctgatcct gagagattgc agcgtggccg   1980
gatggctgct ggggaaccca atgtgcgacg aattcatcaa cgtgcccgaa tggagctaca   2040
tcgtggagaa ggccaaccca gccaacgacc tgtgctaccc agggaacctg aacgactacg   2100
aagaactgaa acacctgctg agcagaatca accactttga gaaaatccag atcatcccca   2160
aaagcagctg gtccgatcac gaagccagca gcggagtgag cagcgcctgc ccataccagg   2220
gaaagtccag ctttttttaga aacgtggtgt ggctgatcaa aaagaacagc gcctacccaa   2280
caatcaagag aagctacaac aacaccaacc aggaagatct gctggtgctg tgggggatcc   2340
accaccctaa cgatgccgcc gagcagacaa ggctgtacca gaacccaacc acctacatct   2400
ccgtggggac aagcacactg aaccagagac tggtgccaaa aatcgccatc agatccaaag   2460
tgaacgggca gagcggaaga atggagttct tctggacaat cctgaaaccc aacgatgcca   2520
tcaacttcga gagcaacgga aacttcatcg ccccagaata cgcctacaaa atcgtgaaga   2580
aaggggacag cgccatcatg aaaagcgaac tggaatacgg caactgcaac accaagtgcc   2640 agacccaat gggggccatc aacagcagca tgccattcca caacatccac cctctgacca   2700
tcggggaatg ccccaaatac gtgaaaagca acagactggt gctggccacc gggctgagaa   2760
acagccctca gagagagacc agaggactgt ttggagccat cgccggcttt atcgagggag   2820
gatggcaggg aatggtggat ggctggtacg ataccacca cagcaacgag caggggagcg   2880
gatacgccgc cgacaaagaa tccacccaga aggccatcga cggcgtgacc aacaaagtga   2940
acagcatcat cgacaaaatg aacacccagt ttgaggccgt gggaagggag tttaacaacc   3000
```

-continued

```
tggaaaggag aatcgagaac ctgaacaaga agatggagga cggattcctg gatgtgtgga    3060
cctacaacgc cgaactgctg gtgctgatgg aaaacgagag aaccctggac tttcacgaca    3120
gcaacgtgaa gaacctgtac gacaaagtga ggctgcagct gagggataac gccaaggagc    3180
tgggcaacgg ctgcttcgag ttctaccaca atgcgataa cgaatgcatg gaaagcatca    3240
gaaacggaac ctacaactac ccccagtaca gcgaagaagc cagactgaaa agagaagaaa    3300
tctccggagt gaaactggaa tccatcggaa cctaccagat cctgagcatc tacagcacag    3360
tggcctcctc cctggccctg gccatcatga tggccggact gagcctgtgg atgtgctcca    3420
acggaagcct gcagtgcaga atctgcatct gactcgagtt tttattgact agttaatcac    3480
ggccgcttat aaagatctaa aatgcataat ttctaaataa tgaaaaaaag tacatcatga    3540
gcaacgcgtt agtatatttt acaatggaga ttaacgctct ataccgttct atgtttattg    3600
attcagatga tgttttagaa aagaaagtta ttgaatatga aactttaat gaagatgaag    3660 atgacgacga tgattattgt tgtaaatctg ttttagatga agaagatgac gcgctaaagt    3720
atactatggt tacaaagtat aagtctatac tactaatggc gacttgtgca agaaggtata    3780
gtatagtgaa aatgttgtta gattatgatt atgaaaaacc aaataaatca gatccatatc    3840
taaaggtatc tcctttgcac ataatttcat ctattcctag tttagaatac                3890
```

<210> SEQ ID NO 23
<211> LENGTH: 1692
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 23

```
atggagaaaa tagtgcttct tcttgcaata gtcagtcttg ttaaaagtga tcagatttgc      60
attggttacc atgcaaacaa ttcaacagag caggttgaca caataatgga aaagaacgtt     120
actgttacac atgcccaaga catactggaa aagacacaca cgggaagct ctgcgatcta      180 gatggagtga agcctctaat tttaagagat tgtagtgtag ctggatggct cctcgggaat     240
ccaatgtgtg acgaattcat caatgtaccg gaatggtctt acatagtgga aaggccaat     300 ccagccaatg acctctgtta cccagggaat ctcaacgact atgaagaact aaaacaccta     360
ttgagcagaa taaaccattt tgagaaaatt cagatcatcc ccaaaagttc ttggtccgat     420
catgaagcct catcagggt gagctcagca tgtccatacc agggaaagtc ctccttttt      480 agaaatgtgg tatggcttat caaaaagaac agtgcatacc aacaataaa gagaagctac     540 aataatacca accaagaaga ctttttggta ctgtggggga ttcaccatcc taatgatgcg     600
gcagagcaga caaggctata tcaaaaccca accacctata tttccgttgg acatcaaca     660 ctaaaccaga gattggtacc aaaaatagct attagatcca agtaaacgg gcaaagtgga     720 agaatggagt tcttctggac aatttttaaa ccgaatgatg caatcaactt cgagagtaat     780
ggaaatttca ttgctccaga atatgcatac aaaattgtca agaaggga ctctgcaatt     840 atgaaaagtg aattggaata tggtaactgc aacaccaagt gtcaaactcc aatggggcg     900 ataaactcta gtatgccatt ccacaacata caccctctca ccatcgggga atgccccaaa     960
tatgtgaaat caaacagatt agtccttgcg actgggctca gaaatagccc tcaaagagag    1020
acaagaggac tatttggagc tatagcaggt tttatagagg aggatggca gggaatggta    1080 gatggttggt atgggtacca ccatagcaat gagcagggga gtgggtacgc tgcagacaaa    1140
gaatccactc aaaaggcaat agatgggtc accaataagg tcaactcgat cattgacaaa    1200
```

```
atgaacactc agtttgaggc cgttggaagg gaatttaata acttagaaag gagaatagag    1260
aatttaaaca agaagatgga agacggattc ctagatgtct ggacttataa tgctgaactt    1320
ctggttctca tggaaaatga gagaactcta gactttcatg actcaaatgt taagaacctc    1380
tacgacaagg tccgactaca gcttagggat aatgcaaagg agctgggtaa cggttgtttc    1440
gagttctatc acaaatgtga taatgaatgt atggaaagta taagaaacgg aacgtataac    1500
tacccgcagt attcagaaga agcaagatta aaaagagaag aaataagtgg agtaaaattg    1560
gaatcaatag gaacttacca aatactgtca atttattcaa cagtggcgag ttccctagca    1620
ctggcaatca tgatggctgg tctatcttta tggatgtgct ccaatggatc gttacaatgc    1680
agaatttgca tt                                                      1692
```

<210> SEQ ID NO 24
<211> LENGTH: 568
<212> TYPE: PRT
<213> ORGANISM: Artificial Sequence
<220> FEATURE:
<223> OTHER INFORMATION: Description of Artificial Sequence: Synthetic protein

<400> SEQUENCE: 24

```
Met Glu Lys Ile Val Leu Leu Ala Ile Val Ser Leu Val Lys Ser
  1               5                  10                  15

Asp Gln Ile Cys Ile Gly Tyr His Ala Asn Asn Ser Thr Glu Gln Val
             20                  25                  30

Asp Thr Ile Met Glu Lys Asn Val Thr Val Thr His Ala Gln Asp Ile
         35                  40                  45

Leu Glu Lys Thr His Asn Gly Lys Leu Cys Asp Leu Asp Gly Val Lys
     50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Asn Pro Ala Asn Asp Leu Cys Tyr Pro Gly Asn Leu Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Lys Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Ile Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255
```

```
Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
            275                 280                 285

Asn Cys Asn Thr Lys Cys Gln Thr Pro Met Gly Ala Ile Asn Ser Ser
            290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
            325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
            370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
            405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
            450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
            485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
            530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
            565
```

FELINE VACCINES AGAINST AVIAN INFLUENZA

INCORPORATION BY REFERENCE

This application makes reference to U.S. patent application Ser. No. 11/211,983 filed Aug. 25, 2005.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention encompasses influenza vaccines, in particular avian influenza vaccines. The vaccine may be a recombinant poxvirus vaccine or an inactivated vaccine. The invention also encompasses recombinant poxvirus vectors encoding and expressing avian influenza antigens, epitopes or immunogens which can be used to protect animals, in particular cats, against avian influenza.

BACKGROUND OF THE INVENTION

Upper respiratory tract diseases (UPTD) are common in felines, especially domestic cats. These diseases exhibit influenza-like symptoms, including fever, nasal discharge, sneezing, coughing, sinusitis and bronchitis, and can potentially be fatal. The most common agents for UPTD include chlamydia, feline herpesvirus-1, feline calicivirus, and *Bordetella bronchiseptica*. More recently, felines have displayed susceptibility of infection to influenza viruses, especially the avian influenza virus (AIV).

AIV is an RNA virus belonging to the family of Orthomyxoviridae, and is classified as a type A influenza virus, which relates its nucleoprotein and membrane proteins. AIV has a lipid envelope that features two distinct glycoproteins: hemagglutinin (HA), which facilitates entry of the virus into the host cells, and neuraminidase (NA), which assists in the release of progeny virus from infected cells (de Jong et al., 2006). Thus far, 16 HA and 9 NA have been detected and can exist in varying combinations (Olsen et al., 2006), thereby forming subtypes of AIV that are based upon these antigenic differences. The H5N1 subtype (virus featuring HA 5 and NA 1) has specifically been associated with recent outbreaks in Asia, Russia, the Middle East, Europe and Africa, and is responsible for the growing concern of avian influenza infection of felids.

Reports regarding avian influenza infection of domestic cats and zoo felids emerged during the 2003 to 2004 avian influenza outbreak in Asia (Keawcharoen et al 2004). These reports described over 150 deaths of tigers and leopards as a result of feeding on raw chicken carcasses that were infected with the avian influenza. These felids developed lesions in the lungs, resulting in congestion and hemorrhaging, moderate meningoencephalitis, and mutifocal necrotizing hepatitis. Since then, scientists have confirmed that felines are susceptible to avian influenza infection via intratracheal injection, consumption of virus-infected chickens, and horizontal transmission through regular contact (Kuiken et al., 2004). The infected cats initially developed such symptoms as raised body temperature, conjunctivitis, and labored breathing, which eventually progressed to severe diffuse alveolar damage and death, although the virus can replicate in the respiratory tract without inducing any signs of the disease (Hinshaw et al. 1981). Further studies revealed that experimentally-infected cats displayed a presence of the virus in both respiratory and extra-respiratory organs, and excreted the virus through both the respiratory and digestive tracts (Rimmelzwaan et al., 2006). In addition, numerous new reports have described infection of domestic cats in Europe and Asia (Butler, 2006).

Considering the susceptibility of felines to AIV and their ability to excrete the virus into their surroundings, a method of preventing AIV infection and protecting felines is essential. The urgency is compounded given the possibility that feline infection may play a role in the epidemiology of AIV in poultry, humans, and other species (Influenza team, 2006; Kuiken et al., 2006). Accordingly, there is a need for an effective vaccine against influenza in felines.

Citation or identification of any document in this application is not an admission that such document is available as prior art to the present invention.

SUMMARY OF THE INVENTION

The present invention encompasses avian influenza immunological compositions, which may be a recombinant avian influenza immunological composition or an inactivated avian influenza immunological composition.

The present invention also encompasses avian influenza vaccines, which may be a recombinant avian influenza vaccine or an inactivated avian influenza vaccine.

Furthermore, the present invention encompasses influenza vaccines wherein the vaccine comprises one or more of an inactivated feline influenza isolate, an inactivated avian influenza isolate, or mixtures thereof.

In an embodiment wherein the avian influenza immunological composition or vaccine is a recombinant immunological composition or vaccine, advantageously, the composition or vaccine comprising a recombinant viral vector and a pharmaceutical or veterinary acceptable excipient, carrier or vehicle; the recombinant viral vector is an avipox expression vector which may comprise a polynucleotide encoding an influenza polypeptide, antigen, epitope or immunogen. The influenza polypeptide, antigen, epitope or immunogen, may be a hemagglutinin, matrix protein, neuraminidase, nonstructural protein, nucleoprotein, polymerase or any fragment thereof.

In an advantageous embodiment, the avian influenza polypeptide, antigen, epitope or immunogen may be derived from a feline infected with influenza. For example, but not by limitation, influenza virus may be isolated from the broncho alveolar lavage and/or lung tissues of an affected felid. Isolation and characterization of the nucleotide sequence of the influenza infecting the felid may be done by routine experimentation by a person of ordinary skill in the art.

The avian influenza polypeptide, antigen, epitope or immunogen may be isolated from an avian influenza.

The avipox expression vector may be an attenuated avipox expression vector. In one embodiment, the avipox expression vector may be a fowlpox vector, advantageously TROVAC. In another embodiment, the avipox expression vector may be a canarypox vector, advantageously ALVAC. The influenza antigen, epitope or immunogen may be a hemagglutinin, such as H5. The fowlpox vector may be vFP89 or vFP2211. The canarypox vector may be vCP2241.

The present invention also encompasses an inactivated influenza immunological composition or vaccine. The inactivated influenza immunological composition or vaccine may be an inactivated influenza. In another embodiment, the inactivated influenza immunological composition or vaccine may be an avian influenza. The immunological composition o vaccine may be inactivated with formalin or beta-propiolactone.

The invention also relates to method of eliciting an immune response against influenza in a Felidae, in particular a cat, which may comprise administering a formulation comprising any one of the above recombinant influenza immunological composition or vaccine, or inactivated immunological composition or vaccine, and a pharmaceutically or veterinarily acceptable carrier, excipient or vehicle in an effective amount for eliciting an immune response. In an advantageous embodiment, an adjuvant may be added. The adjuvant may be aluminum hydroxide, aluminum phosphate, a carbomer or an oil-in-water-emulsion and optionally may comprise CpG. Advantageously, the administration may be subcutaneous intramuscular or transdermal with a needle-free injector.

The invention further relates to method of inducing a immune response against influenza in a Felidae, in particular in a cat, which may comprise administering a formulation comprising any one of the above recombinant influenza immunological compositions or vaccines, or inactivated immunological compositions or vaccines, and a pharmaceutically or veterinarily acceptable carrier, excipient or vehicle in an effective amount for inducing a immune response. In an advantageous embodiment, an adjuvant may be added. The adjuvant may be aluminum hydroxide, aluminum phosphate, a carbomer or an oil-in-water-emulsion and optionally may comprise CpG. Advantageously, the administration may be subcutaneous or intramuscular.

The invention further comprises relates to the inducement or elicication of an immune response against influenza in a Felidae wherein the immune response induced or elicited is a protective immune response.

The invention further encompasses a kit for performing a method of eliciting or inducing an immune response which may comprise any one of the recombinant influenza immunological compositions or vaccines, or inactivated immunological compositions or vaccines, and instructions for performing the method.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawing, in which:

Figure 1:
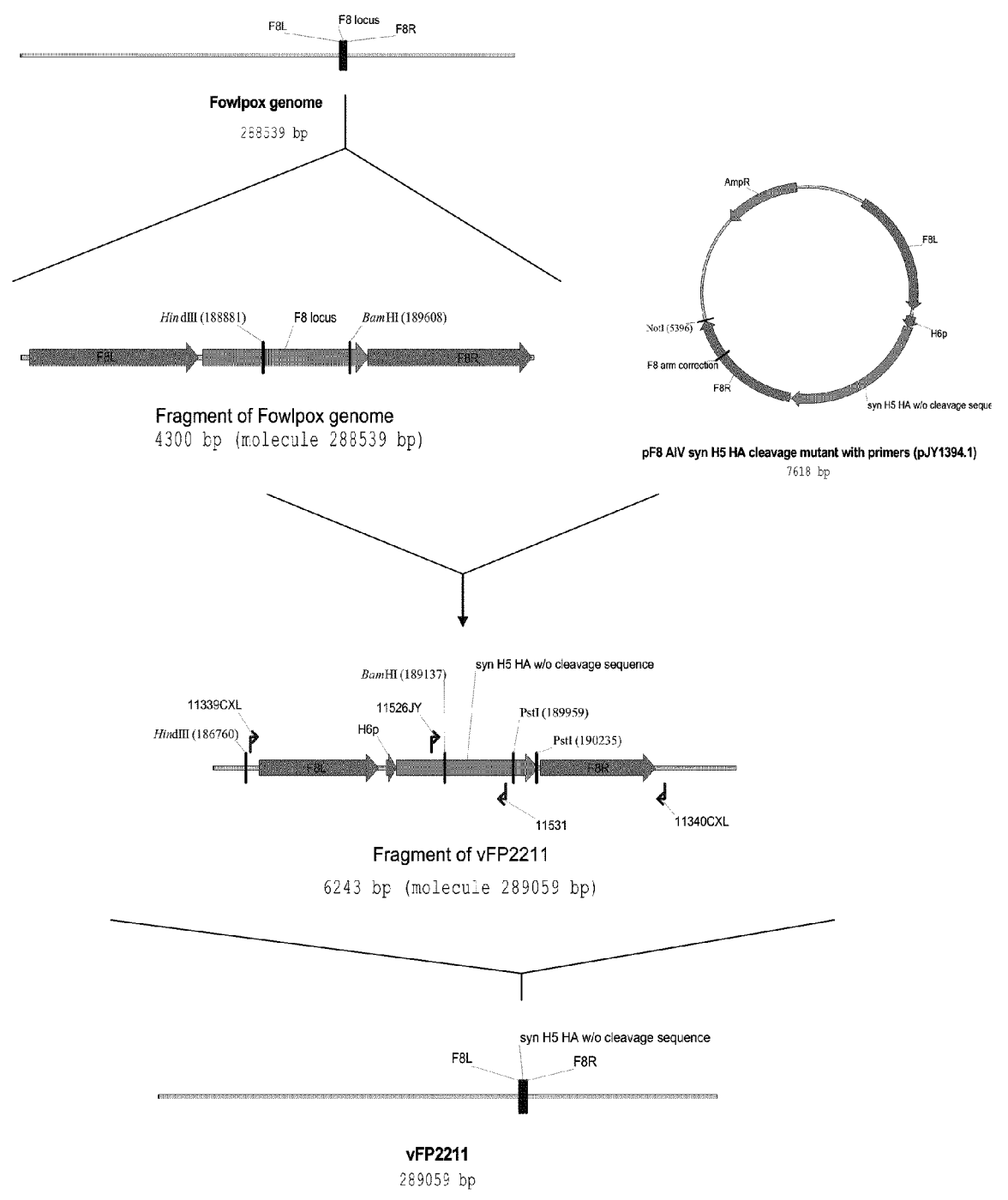

FIG. 1 illustrates the generation of vFP2211, in which plasmid pJY1394.1, containing the synthetic AIV H5 HA insert, and a fragment of the Fowlpox genome at the F8 locus generates vFP2211 through in vitro recombination.

FIG. 2 illustrates the fragment of vFP2211, indicating the positions of the primers for amplifying the AIV probe and for PCR amplification of the F8 arms and insert.

FIG. 7 illustrates a comparison of nucleotide sequences between the wild type H5 HA without cleavage site (CK/Indonesia/2003) and the synthetic AIV H5 HA without cleavage site from plasmid pCR-Script/HA-CK/Indonesia/03-(modified)-avipox (SEQ ID NOS 23 & 15).

FIG. 8 illustrates a comparison of amino acid sequences between the wild type H5 HA without cleavage site (CK/Indonesia/2003) and the synthetic AIV H5 HA without cleavage site from plasmid pCR-Script/HA-CK/Indonesia/03-(modified)-avipox (SEQ ID NOS 16 & 24).

Figure 9:
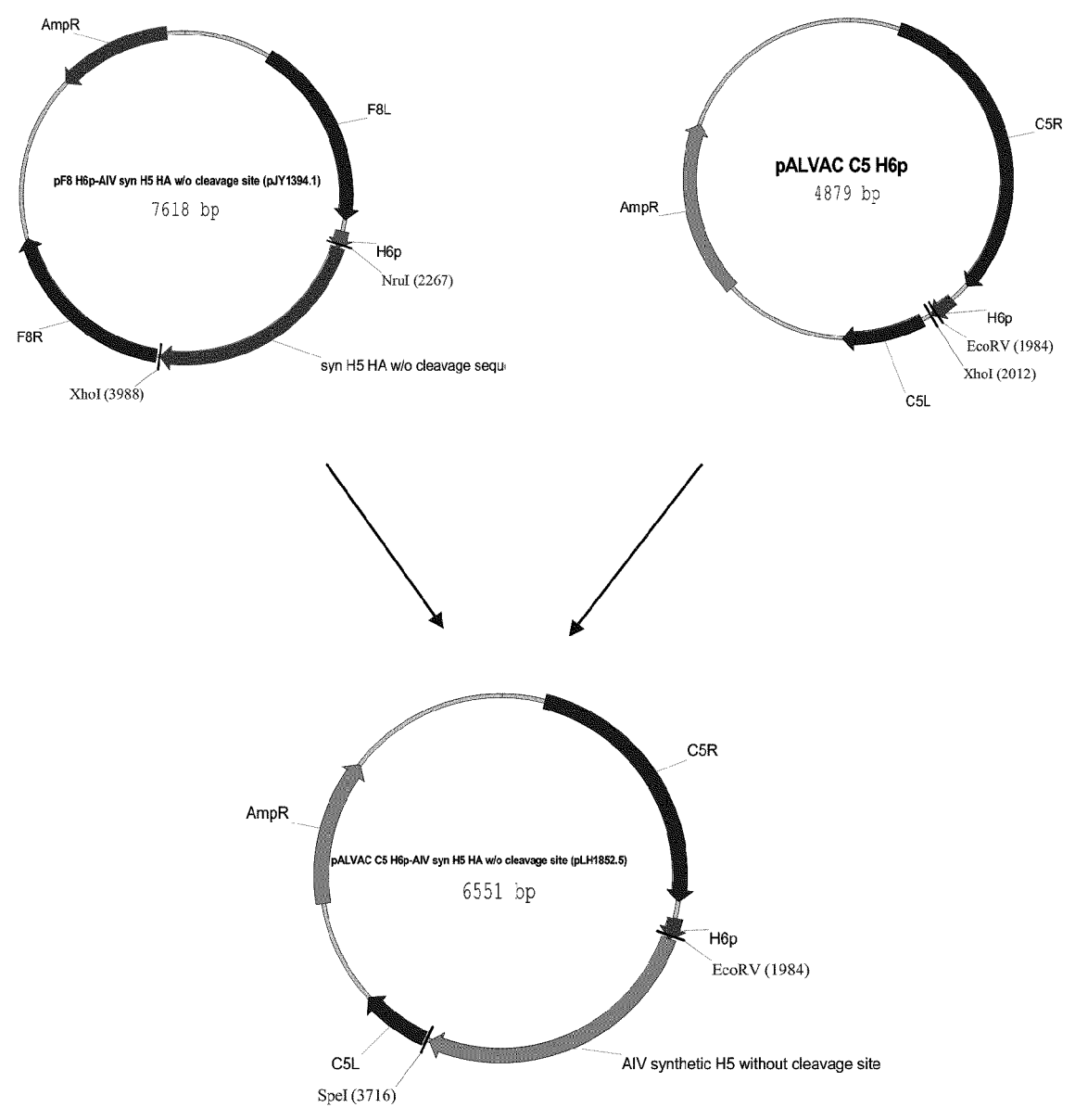

FIG. 9 illustrates the construction of the ALVAC plasmid pLH1852.5, in which the expression cassette of H6p-AIV synthetic H5 HA is isolated by digestion of the plasmid pJY1394.1 and ligated to Eco DNA digested pALVAC C5H6p donor (pCXL148.2).

FIG. 10 illustrates the ALVAC plasmid pLH1852.5.

Figure 11:
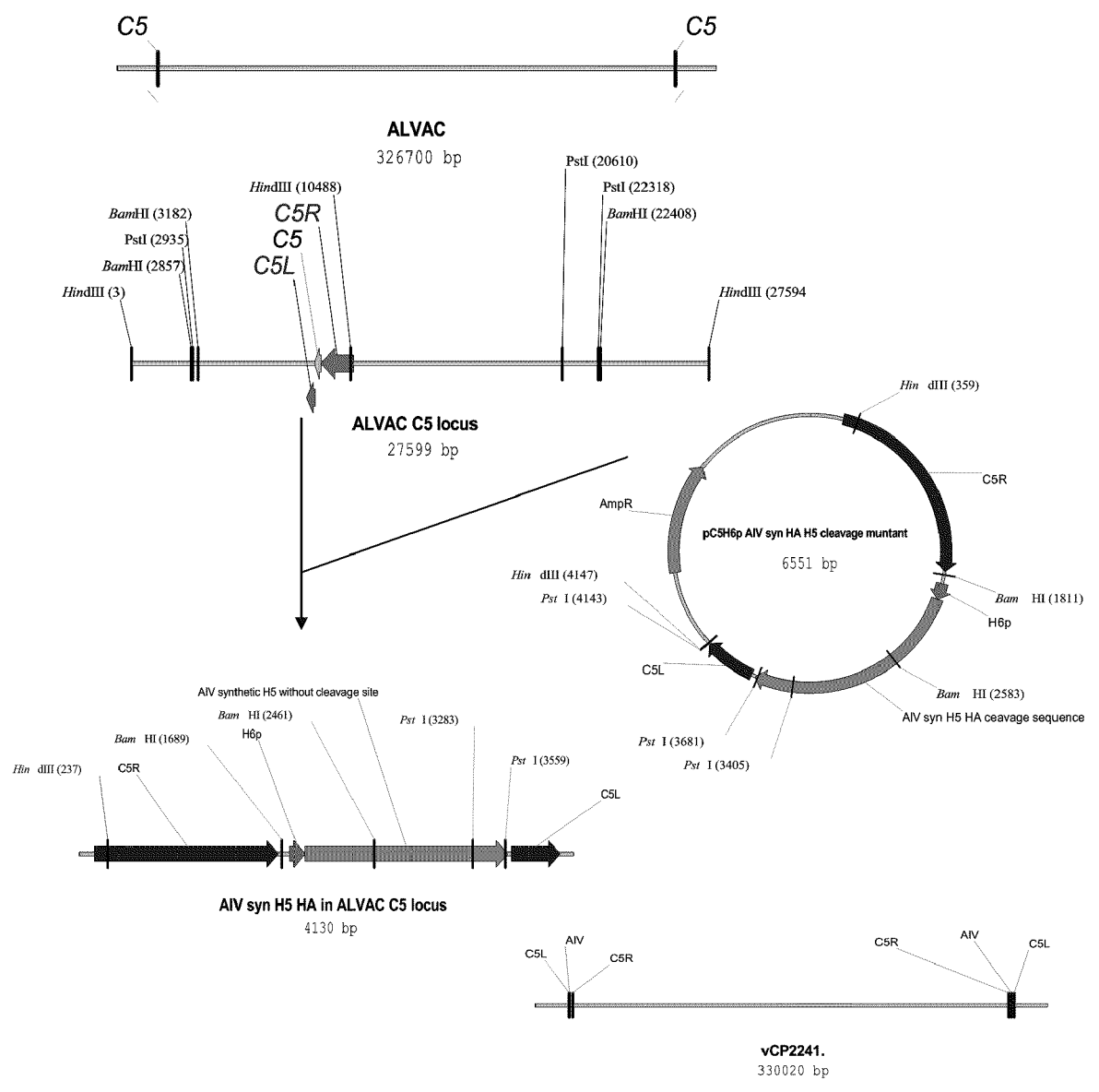

FIG. 11 illustrates the generation of vCP2241, in which ALVAC plasmid pLH1852.5, containing the AIV synthetic H5 HA insert, and a fragment of the ALVAC genome at the C5 locus generates vCP2241 through in vitro recombination.

FIG. 15 illustrates a gel from Western blot analysis indicating the correct insertion of AIV synthetic H5 HA into the C5 locus.

Figure 17:
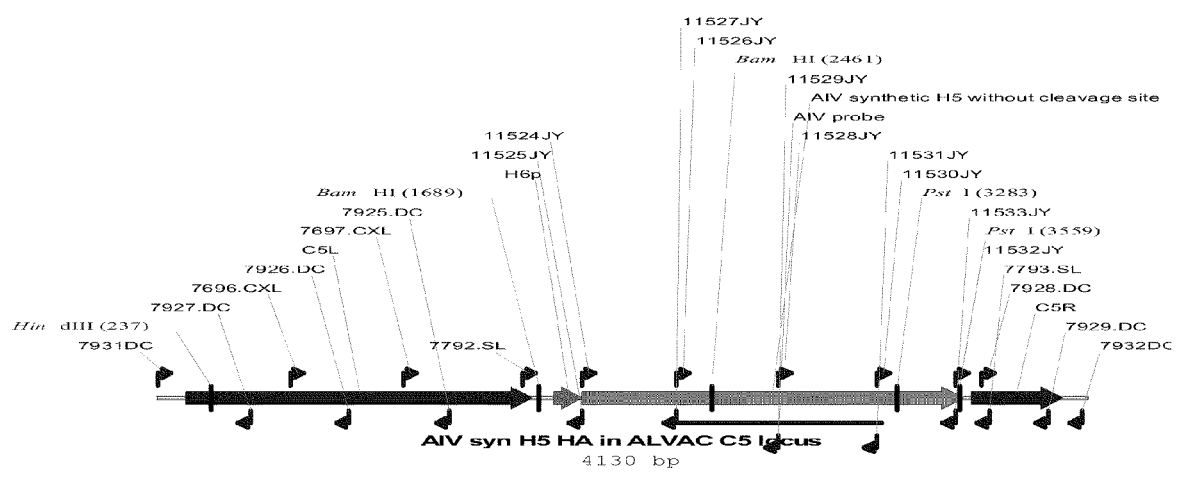

FIG. 17 illustrates the fragment of vCP2241, indicating the positions of the primers for amplifying the AIV probe and for PCR amplification of the C5 arms and insert.

FIG. 19 illustrates the HI antibody responses to, H5N8 AIV (A/Turkey/Ireland/1378/83) NIBRG14 strain) antigens in cats vaccinated with either TROVAC fowlpox virus expressing the H5 gene from A/Turkey/Ireland/1378/83 (vFP89), TROVAC fowlpox virus expressing the H5 gene from A/Chicken/Indonesia/03 (vFP2211), or ALVAC canarypox virus expressing the H5 gene from A/Chicken/Indonesia/03 (vCP2241).

DETAILED DESCRIPTION

Figure 3:
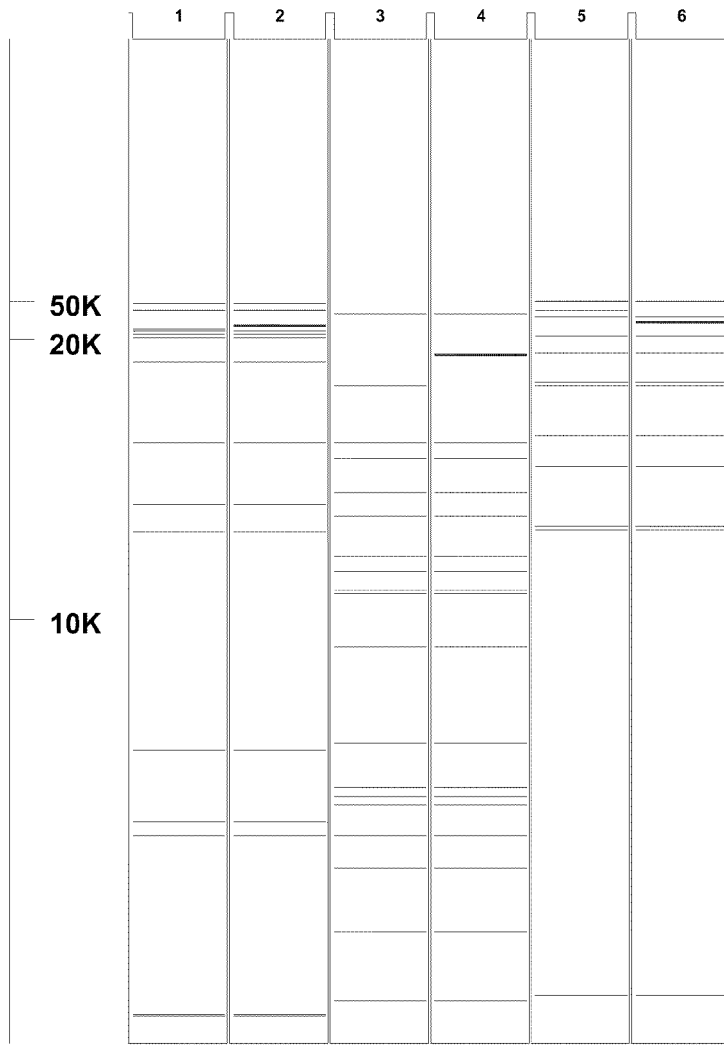
FIG. 3 illustrates a theoretical restriction enzyme gel for the genomic DNA of vFP2211.

The present invention is based, in part, on Applicants' studies demonstrating a recombinant fowlpox and canarypox expressing avian influenza HA is immunogenic in cats.

The present invention encompasses any influenza polypeptide, antigen, epitope or immunogen that elicits an immunogenic response in an animal, advantageously a vertebrate, more advantageously a Felidae, even more advantageously a cat. The influenza polypeptide, antigen, epitope or immunogen may be any influenza polypeptide, antigen, epitope or immunogen, such as, but not limited to, a protein, peptide or fragment thereof, that elicits, induces or stimulates a response in an animal, advantageously a vertebrate, a Felidae more advantageously a cat.

In an advantageous embodiment, the influenza polypeptide, antigen, epitope or immunogen is derived from a feline infected with influenza. For example, but not by limitation, influenza virus may be isolated from the broncho alveolar lavage and/or lung tissues of an affected felid. Isolation and characterization of the nucleotide sequence of the influenza infecting the felid may be done by routine experimentation by a person of ordinary skill in the art.

In another advantageous embodiment, the influenza polypeptide, antigen, epitope or immunogen may be derived from an avian infected with influenza or an avian influenza strain. Advantageously, the avian influenza antigen, epitope or immunogen is a hemagglutinin (HA) (e.g., HA precursor, H1, H2, protein, matrix protein (e.g., matrix protein M1 or M2), neuraminidase, nonstructural (NS) protein (e.g., NS1 or NS2), nucleoprotein (NP) and polymerase (e.g., PA polymerase, PB1 polymerase 1 or PB2 polymerase 2).

Examples of avian influenza strains that may be used in methods of the present invention include, but are not limited to, turkey influenza virus strain A/Turkey/Ireland/1378/83 (H5N8) (see, e.g., Taylor et al., 1988b), turkey influenza virus strain A/Turkey/England/63 (H7N3) (see, e.g., Alexander et al., 1979; Rott et al., 1979; Horimoto et al., 2001), turkey influenza virus strain A/Turkey/England/66 (H6N2) (see, e.g., Alexander et al., 1979), A/Turkey/England/69 (H7N2) (see, e.g., Alexander et al., 1979; Horimoto et al., 2001), A/Turkey/Scotland/70 (H6N2) (see, e.g., Banks et al., 2000; Alexander et al., 1979), turkey influenza virus strain A/Turkey/England/N28/73 (H5N2) (see, e.g., Alexander et al., 1979), turkey influenza virus strain A/Turkey/England/110/77 (H6N2) (see, e.g., Alexander et al., 1979), turkey influenza virus strain A/Turkey/England/647/77 (H1N1) (see, e.g., Alexander et al., 1979; Karasin et al., 2002)), turkey influenza virus strain A/turkey/Ontario/7732/66 (H5N9) (see, e.g., Slemons et al., 1972; Philpott et al., 1989), turkey influenza virus strain A/Turkey/England/199/79 (H7N7) (see, e.g., Horimoto et al., 2001), turkey influenza virus strain A/Turkey/Ontario/7732/66 (H5N9) (see, e.g., Horimoto et al., 2001; Panigrahy et al., 1996), turkey influenza virus strain A/Turkey/Ireland/1378/85 (H5N8) (see, e.g., Horimoto et al., 2001; Walker et al., 1993), turkey influenza virus strain A/Turkey/England/50-92/91 (H5N1) (see, e.g., Horimoto et al., 2001; Howard et al., 2006), turkey influenza virus strain A/Turkey/Wisconsin/68 (H5N9), turkey influenza virus strain A/Turkey/Masschusetts/65 (H6N2), turkey influenza virus strain A/Turkey/Oregon/71 (H7N3), (see, e.g., Orlich et al., 1990), turkey influenza virus strain A/Turkey/Ontario/6228/67 (H8N4), turkey influenza virus strain A/Turkey/Wisconsin/66 (H9N2), (see, e.g., Zakstel'skaia et al., 1977), turkey influenza virus strain A/Turkey/England/647/77 (H1N1) (see, e.g., Karasin et al., 2002; Alexander et al., 1979), turkey influenza virus strain A/Turkey/Ontario/6118/68 (H8N4) (see, e.g., Blok et al., 1982), turkey influenza virus strain A/Tur/Ger 3/91 (see, e.g., Zakay-Rones et al., 1995), turkey influenza virus strain A/Turkey/Minnesota/833/80 (H4N2) (see, e.g., Gubareva et al., 1997) chicken influenza virus strain A/Chicken/Indonesia/03 (H5N1), chicken influenza virus strain A/Chicken/FPV/Rostock/1934 (see, e.g., Ohuchi et al., 1994), chicken influenza virus strain A/Chicken/Texas/298313/04 (see, e.g., Lee et al., 2005), chicken influenza virus strain A/Chicken/Texas/167280-4-/02 (see, e.g., Lee et al., 2005), chicken influenza virus strain A/Chicken/Hong Kong/220/97 (see, e.g., Perkins et al., 2001), chicken influenza virus strain A/Chicken/Italy/8/98 (see, e.g., Capua et al., 1999), chicken influenza virus strain A/Chicken/Victoria/76 (H7N7) (see, e.g., Zambon, 2001; Nestorowicz et al., 1987), chicken influenza virus strain A/Chicken/Germany/79 (H7N7) (see, e.g., Rohm et al., 1996), chicken influenza virus strain A/Chicken/Scotland/59 (H5N1) (see, e.g., Horimoto et al., 2001; De et al., 1988; Wood et al., 1993), chicken influenza virus strain A/Chicken/Pennsylvania/1370/83 (H5N2) (see, e.g., Bean et al., 1985; van der Goot et al., 2002), chicken influenza virus strain A/Chicken/Queretaro-19/95 (H5N2) (see, e.g., Horimoto et al., 2001; Garcia et al., 1998), chicken influenza virus strain A/Chicken/Queretaro-20/95 (H5N2) (see, e.g., Horimoto et al., 2001), chicken influenza virus strain A/Chicken/Hong Kong/258/97 (H5N1) (see, e.g., Horimoto et al., 2001; Webster, 1998), chicken influenza virus strain A/Chicken/Italy/1487/97 (H5N2) (see, e.g., Horimoto et al., 2001), chicken influenza virus strain A/Chicken/Leipzig/79 (H7N7) (see, e.g., Horimoto et al., 2001; Rohm et al., 1996), chicken influenza virus strain A/Chicken/Victoria/85 (H7N7) (see, e.g., Horimoto et al., 2001), chicken influenza virus strain A/Chicken/Victoria/92 (H7N3) (see, e.g., Horimoto et al., 2001), chicken influenza virus strain A/Chicken/Queensland/95 (H7N3) (see, e.g., Horimoto et al., 2001), chicken influenza virus strain A/Chicken/Pakistan/1369/95 (H7N2) (see, e.g., Horimoto et al., 2001), chicken influenza virus strain A/Chicken/Pakistan/447-4/95 (H7N3) (see, e.g., Horimoto et al., 2001), chicken influenza virus strain A/Chicken/HK/G9/97 (H9N2) (see, e.g., Leneva et al., 2001), chicken influenza virus strain A/Chicken/Nakom-Patom/Thailand/CU-K2/2004(H5N1) (see, e.g., Anwar et al., 2006; Viseshakul et al., 2004), chicken influenza virus strain A/Chicken/Hong Kong/31.2/2002

(H5N1), (see, e.g., Anwar et al., 2006;), chicken influenza virus strain A/Chicken/Vietnam/C58/04 (H5N1), (see, e.g., Anwar et al., 2006;), chicken influenza virus strain A/Chicken/Vietnam/38/2004(H5N1). (see, e.g., Anwar et al., 2006), chicken influenza virus strain A/Chicken/Alabama/7395/75 (H4N8), (see, e.g., Swayne et al., 1994), chicken influenza virus strain A/Chicken/Germany/N/49 (H10N7), (see, e.g., Yamane et al., 1981), chicken influenza virus strain A/Chicken/Beijing/1/94 (H9N2) (see, e.g., Karasin et al., 2002), chicken influenza virus strain A/Chicken/Hong Kong/G23/97 (H9N2) (see, e.g., Karasin et al., 2002), chicken influenza virus strain A/Chicken/Pennsylvania/8125/83 (H5N2) (see, e.g., Karasin et al., 2002; Shortridge et al., 1998), chicken influenza virus strain A/Chicken/Hong Kong/97 (H5N1) (see, e.g., Chen et al., 2003), duck influenza virus strain A/Duck/Anyang/AVL-1/01 (see, e.g., Tumpey et al., 2002), duck influenza virus strain A/Duck/New York/17542-4/86 (H9N1) (see, e.g., Banks et al., 2000), duck influenza virus strain A/Duck/Alberta/28/76 (H4N6) (see, e.g., Blok et al., 1982), duck influenza virus strain A/Duck/Nanchang/4-165/2000 (H4N6) (see, e.g., Liu et al., 2003), duck influenza virus strain A/Duck/Germany/49 (H10N7) (see, e.g., Blok et al., 1982), duck influenza virus strain A/Black Duck/Australia/702/78 (H3N8) (see, e.g., Blok et al., 1982), duck influenza virus strain A/Duck/Vietnam/11/2004 (H5N1), (see, e.g., Anwar et al., 2006), duck influenza virus strain A/Duck/Alberta/60/76 (H12N5), (see, e.g., Baez et al., 1981), duck influenza virus strain A/Duck/Hong Kong/196/77 (H1) (see, e.g., Karasin et al., 2002; Kanegae et al., 1994), duck influenza virus strain A/Duck/Wisconsin/1938/80 (H1N1) (see, e.g., Karasin et al., 2002), duck influenza virus strain A/Duck/Bavaria/2/77 (H1N1) (see, e.g., Karasin et al., 2002; Ottis et al., 1980), duck influenza virus strain A/Duck/Bavaria/1/77 (H1N1) (see, e.g., Ottis et al., 1980), duck influenza virus strain A/Duck/Australia/749/80 (H1N1) (see, e.g., Karasin et al., 2002), duck influenza virus strain A/Duck/Hong Kong/Y280/97 (H9N2) (see, e.g., Karasin et al., 2002; Guan et al., 2000), duck influenza virus strain A/Duck/Alberta/35/76 H1N1) (see, e.g., Austin et al., 1990), avian influenza virus strain A/Mallard duck/Gurjev/263/82 (H14N5), (see, e.g., Kawaoka et al., 1990), avian influenza virus strain A/Mallard duck/PA/10218/84 (H5N2) (see, e.g., Smirnov et al., 2000), avian influenza virus strain A/Mallard duck/Astrakhan/244/82 (H14N6) (see, e.g., Karasin et al., 2002), goose influenza virus strain A/Goose/Guangdong/1/96 (see, e.g., Xu et al., 1999), goose influenza virus strain A/Goose/Leipzig/137-8/79 (H7N7) (see, e.g., Horimoto et al., 2001), goose influenza virus strain A/Goose/Hong Kong/W222/97 (H6N7) (see, e.g., Chin et al., 2002), goose influenza virus strain A/Goose/Leipzig/187-7/79 (H7N7) (see, e.g., Horimoto et al., 2001), goose influenza virus strain A/Goose/Leipzig/192-7/79 (H7N7) (see, e.g., Horimoto et al., 2001), avian influenza virus strain A/Env/HK/437-4/99 (see, e.g., Cauthen et al., 2000), avian influenza virus strain A/Env/HK/437-6/99 (see, e.g., Cauthen et al., 2000), avian influenza virus strain A/Env/HK/437-8/99 (see, e.g., Cauthen et al., 2000), avian influenza virus strain A/Env/HK/437-10/99, (see, e.g., Cauthen et al., 2000), avian influenza virus strain A/Fowl plague virus strain/Dutch/27 (H7N7) (see, e.g., Horimoto et al., 2001; Carter et al., 1982), avian influenza virus strain A/Fowl plague virus strain/Dobson/27 (H7N7) (see, e.g., Horimoto et al., 2001), avian influenza virus strain A/Fowl plague virus strain/Rostock/34 (H7N1) (see, e.g., Horimoto et al., 2001; Takeuchi et al., 1994), avian influenza virus strain A/Fowl plague virus strain/Egypt/45 (H7N1) (see, e.g., Horimoto et al., 2001), avian influenza virus strain A/Fowl plague virus strain/Weybridge (H7N7) (see, e.g., Tonew et al., 1982), avian influenza virus strain A/Tern/South Africa/61 (H5N3) (see, e.g., Horimoto et al., 2001; Perkins et al., 2002; Walker et al., 1992), avian influenza virus strain A/Tern/Australia/G70C/75 (H11N9) (see, e.g., Pruett et al., 1998), avian influenza virus strain A/Quail/Vietnam/36/04(H5N1). (see, e.g., Anwar et al., 2006), avian influenza virus strain A/Gull/Maryland/704/77 (H13N6), (see, e.g., Iamnikova et al., 1989), avian influenza virus strain A/Black-headed gull/Sweden/5/99 (H16N3) (see, e.g., Fouchier et al., 2005), avian influenza virus strain A/Herring gull/DE/677/88 (H2N8) (see, e.g., Saito et al., 1993), avian influenza virus strain A/Swan/Italy/179/06 (H5N1) (see, e.g., Terregino et al., 2006), avian influenza virus strain A/Hong Kong/156/97 (A/HK/156/97) (see, e.g., Leneva et al., 2001; Claas et al., 1998; Cauthen et al., 2000), avian influenza virus strain A/Quail/HK/G1/97 (H9N2) (see, e.g., Leneva et al., 2001), avian influenza virus strain A/Quail/Hong Kong/AF157/93 (H9N2) (see, e.g., Karasin et al., 2002), avian influenza virus strain A/Teal/HK/W312/97 (H6N1) (see, e.g., Leneva et al., 2001), avian influenza virus strain A/Shearwater/West Australia/2576/79 (H15N9) (see, e.g., Rohm et al., 1996), avian influenza virus strain A/Shearwater/Australia/72 (H6N5) (see, e.g., Harley et al., 1990), avian influenza virus strain A/Hong Kong/212/03 (see, e.g., Shinya et al., 2005), avian influenza virus strain A/England/321/77 (H3N2) (see, e.g., Hauptmann et al., 1983), avian pandemic influenza A viruses of avian origin (see, e.g., Audsley et al., 2004) avian H5N1 influenza virus, avian H7N1 influenza strain (see, e.g., Foni et al., 2005), avian H9N2 influenza virus (see, e.g., Leneva et al., 2001), and avian influenza virus, cold-adapted (ca) and temperature sensitive (ts) master donor strain, A/Leningrad/134/17/57 (H2N2) (see, e.g., Youil et al., 2004), the disclosures of which are incorporated by reference.

Other influenza strains that may be used in methods of the present invention include, but are not limited to, equine influenza virus (A/Equi 2 (H3N8), Newmarket 1/93) (see, e.g., Mohler et al., 2005; Nayak et al., 2005), equine-2 influenza virus (EIV; subtype H3N8) (see, e.g., Lin et al., 2001), equine-2 influenza virus, A/Equine/Kentucky/1/91 (H3N8) (see, e.g., Youngner et al., 2001), equine influenza virus strain A/Equine/Berlin/2/91 (H3N8) (see, e.g., Ilobi et al., 1998), equine influenza virus strain A/Equine/Cambridge/1/63 (H7N7) (see, e.g., Gibson et al., 1992), equine influenza virus strain A/Equine/Prague/1/56 (H7N7) (see, e.g., Karasin et al., 2002; Appleton et al., 1989), equine influenza virus strain A/Eq/Kentucky/98 (see, e.g., Crouch et al., 2004), equine influenza virus strain A/Equi 2 (Kentucky 81) (see, e.g., Short et al., 1986; Horner et al., 1988), equine influenza virus strain A/Equine/Kentucky/1/81 (Eq/Ky) (see, e.g., Breathnach et al., 2004), equine influenza virus strain A/Equine/Kentucky/1/81 (H3N8) (see, e.g., Olsen et al., 1997; Morley et al., 1995; Ozaki et al., 2001; Sugiura et al., 2001; Goto et al., 1993), equine influenza virus strain A/Equine/Kentucky/1/91 (H3N8) (see, e.g., Youngner et al., 2001), equine influenza virus strain A/Equine/Kentucky/1277/90 (Eq/Kentucky) (see, e.g., Webster et al., 1993), equine influenza virus strain A/Equine/Kentucky/2/91 (H3N8) (see, e.g., Donofrio et al., 1994), equine influenza virus strain A/Equine/Kentucky/79 (H3N8) (see, e.g., Donofrio et al., 1994), equine influenza virus strain A/Equine/Kentucky/81 (see, e.g., Sugiura et al., 2001), equine influenza virus strain A/Equine/Kentucky/91 (H3N8) (see, e.g., Gross et al., 1998), equine influenza virus strain A/Equine-2/Kentucky/95 (H3N8) (see, e.g., Heldens et al., 2004) and equine influenza virus strain A/Equine-2/Kentucky/98 (see, e.g., Chambers et al., 2001), equine influenza virus strain A/Eq/Newmarket/1/77 (see, e.g., Lindstrom et al., 1998), equine influenza virus strain A/Eq/Newmarket/5/03

(see, e.g., Edlund Toulemonde et al., 2005), equine influenza virus strain A/Equi 2 (H3N8), Newmarket 1/93 (see, e.g., Mohler et al., 2005; Nayak et al., 2005), equine influenza virus strain A/Equi-2/Newmarket-1/93 (see, e.g., Heldens et al., 2002), equine influenza virus strain A/Equine/Newmarket/2/93 (see, e.g., Wattrang et al., 2003), equine influenza virus strain A/Equine/Newmarket/79 (H3N8) (see, e.g., Duhaut et al., 2000; Noble et al., 1994; Duhaut et al., 1998; Hannant et al., 1989; Hannant et al., 1989; Hannant et al., 1988; Richards et al., 1992; Heldens et al., 2004), equine influenza virus strain A/Equine/Newmarket/1/77 (H7N7) (see, e.g., Goto et al., 1993; Sugiura et al., 2001) and equine influenza virus strain A/Equine-2/Newmarket-2/93 (see, e.g., Heldens et al., 2004), equine influenza virus strain A/Eq/Miami/63 (H3N8) (see, e.g., van Maanen et al., 2003), A/Equi 1 (Prague strain) (see, e.g., Horner et al., 1988; Short et al., 1986), equine influenza virus strain A/Equi 2 (Miami) (see, e.g., Short et al., 1986), equine influenza virus strain A/Equi-1/Prague/56 (Pr/56) (see, e.g., Heldens et al., 2002), equine influenza virus strain A/Equi-2/Suffolk/89 (Suf/89) (see, e.g., Heldens et al., 2002), equine influenza virus strain A/Equine 2/Sussex/89 (H3N8) (see, e.g., Mumford et al., 1994), equine influenza virus strain A/Equine/Sussex/89 (see, e.g., Wattrang et al., 2003), equine influenza virus strain A/Equine-2/Saskatoon/90 (see, e.g., Chambers et al., 2001), equine influenza virus strain A/Equine/Prague/1/56 (H7N7) (see, e.g., Donofrio et al., 1994; Morley et al., 1995), equine influenza virus strain A/Equine/Miami/1/63 (H3N8) (see, e.g., Morley et al., 1995; Ozaki et al., 2001; Thomson et al., 1977; Mumford et al., 1988; Donofrio et al., 1994; Mumford et al., 1983), A/Aichi/2/68 (H3N2) (see, e.g., Ozaki et al., 2001), equine influenza virus strain A/Equine/Tokyo/2/71 (H3N8) (see, e.g., Goto et al., 1993), equine influenza virus strain A/Eq/LaPlata/1/88 (see, e.g., Lindstrom et al., 1998), equine influenza virus strain A/Equine/Jilin/1/89 (Eq/Jilin) (see, e.g., Webster et al., 1993), equine influenza virus strain A/Equine/Alaska/1/91 (H3N8) (see, e.g., Webster et al., 1993), equine influenza virus strain A/Equine/Saskatoon/1/91 (H3N8) (see, e.g., Morley et al., 1995), equine influenza virus strain A/Equine/Rome/5/91 (H3N8) (see, e.g., Sugiura et al., 2001), equine influenza virus strain A/Equine/La Plata/1/93 (H3N8) (see, e.g., Ozaki et al., 2001), equine influenza virus strain A/Equine/La Plata/1/93 (LP/93) (see, e.g., Sugiura et al., 2001), equine influenza virus strain A/Eq/Holland/1/95 (H3N8) (see, e.g., van Maanen et al., 2003) and equine influenza virus strain A/Eq/Holland/2/95 (H3N8) (see, e.g., van Maanen et al., 2003), human influenza virus A(H3N2) isolates (see, e.g., Abed et al., 2002), human influenza virus A/Memphis/1/71 (H3N2) (see, e.g., Suzuki et al., 1996), human influenza virus A/Nanchang/933/95 (H3N2) virus (see, e.g., Scholtissek et al., 2002), human influenza virus A/PR/8/34 (H1N1) virus (see, e.g., Scholtissek et al., 2002), human influenza virus A/Singapore/57 (H2N2) virus (see, e.g., Scholtissek et al., 2002), influenza virus A (see, e.g., Chare et al., 2003), influenza virus A/HK/213/03 (see, e.g., Guan et al., 2004; Anwar et al., 2006), influenza virus strain A/HK/483/97 (see, e.g., Cheung et al., 2002), influenza virus strain A/HK/486/97 (see, e.g., Cheung et al., 2002), influenza virus strain A/Thailand/5(KK-494)/2004 (H5N1). (see, e.g., Anwar et al., 2006), influenza virus strain A PR/8/34 (PR8) virus strain (H1N1 subtype) (see, e.g., Mantani et al., 2001), influenza virus strain A/Aichi/2/68(H3N2) (see, e.g., Miyamoto et al., 1998), influenza virus strain A/Ann Arbor/6/60 cold-adapted virus strain (see, e.g., Treanor et al., 1994), influenza virus strain A/Beijing 32/92 (H3N2) (see, e.g., Zakay-Rones et al., 1995), influenza virus strain A/Charlottesville/31/95 (H1N1) (see, e.g., Gubareva et al., 2002), influenza virus strain A/Kawasaki/86 (H1N1) virus strain (see, e.g., Staschke et al., 1998), influenza virus strain A/Korea/82 (H3N2) (see, e.g., Treanor et al., 1994), influenza virus strain A/Leningrad/134/57 (see, e.g., Egorov et al., 1998), influenza virus strain A/NWS/33 (H1N1) (see, e.g., Sidwell et al., 1998), influenza virus strain A/PR/8/34(H1N1) (see, e.g., Miyamoto et al., 1998), influenza virus strain A/PR8/34 (see, e.g., Nunes-Correia et al., 1999; Tree et al., 2001), influenza virus strain A/Puerto Rico (PR)/8/34 (see, e.g., Egorov et al., 1998), influenza virus strain A/Puerto Rico/8-Mount Sinai (see, e.g., Mazanec et al., 1995), influenza virus strain A/Shangdong 9/93 (H3N2) (see, e.g., Zakay-Rones et al., 1995; Sidwell et al., 1998), influenza virus strain A/Shingapol/1/57(H2N2) (see, e.g., Miyamoto et al., 1998), influenza virus strain A/Singapore 6/86 (H1N1) (see, e.g., Zakay-Rones et al., 1995), influenza virus strain A/Singapore/1/57 (H2N2) (see, e.g., Bantia et al., 1998), influenza virus strain A/Texas 36/91 (H1N1) (see, e.g., Zakay-Rones et al., 1995), influenza virus strain A/Texas/36/91 (H1N1) virus strain (see, e.g., Gubareva et al., 2001; Halperin et al., 1998), influenza virus strain A/Texas/36/91(H1N1) (see, e.g., Hayden et al., 1994), influenza virus strain A/Udorn/72 virus infection (see, e.g., Shimizu et al., 1999), influenza virus A/Victoria/3/75 (H3N2) (see, e.g., Sidwell et al., 1998), influenza virus A/Virginia/88(H3N2) (see, e.g., Hayden et al., 1994), influenza virus A/WSN/33 (H1N1) (see, e.g., Lu et al., 2002), influenza virus A/WSN/33 (see, e.g., Gujuluva et al., 1994), influenza virus B (see, e.g., Chare et al., 2003), influenza virus B/Ann Arbor 1/86 (see, e.g., Zakay-Rones et al., 1995), influenza virus B/Harbin/7/94 (see, e.g., Halperin et al., 1998), influenza virus B/Hong Kong/5/72 (see, e.g., Sidwell et al., 1998), influenza virus B/Lee/40 (see, e.g., Miyamoto et al., 1998), influenza virus B/Victoria group (see, e.g., Nakagawa et al., 1999), influenza virus B/Yamagata 16/88 (see, e.g., Zakay-Rones et al., 1995), influenza virus B/Yamagata group (see, e.g., Nakagawa et al., 1999), influenza virus B/Yamanashi/166/98 (see, e.g., Hoffmann et al., 2002), influenza virus C (see, e.g., Chare et al., 2003), influenza virus strain A/Equi/2/Kildare/89 (see, e.g., Quinlivan et al., 2004), influenza virus type B/Panama 45/90 (see, e.g., Zakay-Rones et al., 1995), live, cold-adapted, temperature-sensitive (ca/ts) Russian influenza A vaccines (see, e.g., Palker et al., 2004), swine H1 and H3 influenza viruses (see, e.g., Gambaryan et al., 2005), swine influenza A viruses (see, e.g., Landolt et al., 2005), swine influenza virus (SIV) (see, e.g., Clavijo et al., 2002), swine influenza virus A/Sw/Ger 2/81 (see, e.g., Zakay-Rones et al., 1995), swine influenza virus A/Sw/Ger 8533/91 (see, e.g., Zakay-Rones et al., 1995), swine influenza virus strain A/Swine/Wisconsin/125/97 (H1N1) (see, e.g., Karasin et al., 2002; Karasin et al., 2006), swine influenza virus strain A/Swine/Wisconsin/136/97 (H1N1) (see, e.g., Karasin et al., 2002), swine influenza virus strain A/Swine/Wisconsin/163/97 (H1N1) (see, e.g., Karasin et al., 2002), swine influenza virus strain A/Swine/Wisconsin/164/97 (H1N1) (see, e.g., Karasin et al., 2002), swine influenza virus strain A/Swine/Wisconsin/166/97 (H1N1) (see, e.g., Karasin et al., 2002), swine influenza virus strain A/Swine/Wisconsin/168/97 (H1N1) (see, e.g., Karasin et al., 2002), swine influenza virus strain A/Swine/Wisconsin/235/97 (H1N1) (see, e.g., Karasin et al., 2002; Olsen et al., 2000), swine influenza virus strain A/Swine/Wisconsin/238/97 (H1N1) (see, e.g., Karasin et al., 2002; Ayora-Talayera et al., 2005), swine influenza virus strain A/Swine/Wisconsin/457/98 (H1N1) (see, e.g., Karasin et al., 2002), swine influenza virus strain A/Swine/Wisconsin/458/98 (H1N1) (see, e.g., Karasin et al., 2002; Karasin et al., 2006), swine influenza virus strain A/Swine/Wisconsin/464/98 (H1N1) (see, e.g., Karasin et al., 2002; Karasin et al., 2006), swine influenza virus strain A/Swine/Indiana/1726/88 (H1N1) (see, e.g., Karasin et al., 2002; Macklin et al., 1998), swine influenza virus strain A/Swine/Indiana/9K035/99 (H1N2) (see, e.g., Karasin et al., 2002; Karasin et al., 2000), swine influenza virus strain A/Swine/Nebraska/1/92 (H1N1) (see, e.g., Karasin et al., 2002), swine influenza virus strain A/Swine/Quebec/91 (H1N1) (see, e.g., Karasin et al., 2002), swine influenza virus strain A/Swine/Quebec/81 (H1N1) (see, e.g., Karasin et al., 2002), swine influenza virus strain A/Swine/New Jersey/11/76 (H1N1) (see, e.g., Karasin et al., 2002), swine influenza virus strain A/Swine/Ehime/1/80 (H1N2) (see, e.g., Karasin et al., 2002; Nerome et al., 1985), swine influenza virus strain A/Swine/England/283902/93 (H1N1) (see, e.g., Karasin et al., 2002), swine influenza virus strain A/Swine/England/195852/92 (H1N1) (see, e.g., Karasin et al., 2002; Brown et al., 1993), swine influenza virus strain A/Swine/Germany/8533/91 (H1N1) (see, e.g., Karasin et al., 2002), swine influenza virus strain A/Swine/Germany/2/81 (H1N1) (see, e.g., Karasin et al., 2002), swine influenza virus strain A/Swine/Nebraska/209/98 (H3N2) (see, e.g., Karasin et al., 2002), A/Swine/Iowa/533/99 (H3N2) (see, e.g., Karasin et al., 2002), swine influenza virus strain A/Swine/Iowa/569/99 (H3N2) (see, e.g., Karasin et al., 2002), swine influenza virus strain A/Swine/Minnesota/593/99 (H3N2) (see, e.g., Karasin et al., 2002; Ayora-Talayera et al., 2005), swine influenza virus strain A/Swine/Iowa/8548-1/98 (H3N2) (see, e.g., Karasin et al., 2002), swine influenza virus strain A/Swine/Minnesota/9088-2/98 (H3N2) (see, e.g., Karasin et al., 2002), swine influenza virus strain A/Swine/Texas/4199-2/98 (H3N2) (see, e.g., Karasin et al., 2002), swine influenza virus strain A/Swine/Ontario/41848/97 (H3N2) (see, e.g., Karasin et al., 2002), swine influenza virus strain A/Swine/North Carolina/35922/98 (H3N2) (see, e.g., Karasin et al., 2002), /Swine/Colorado/1/77 (H3N2) (see, e.g., Karasin et al., 2002), swine influenza virus strain A/Swine/Hong Kong/3/76 (H3N2) (see, e.g., Karasin et al., 2002), swine influenza virus strain A/Swine/Hong Kong/13/77 (H3N2) (see, e.g., Karasin et al., 2002), swine influenza virus strain A/Swine/Nagasaki/1/90 (H1N2) (see, e.g., Karasin et al., 2002), swine influenza virus strain A/Swine/Nagasaki/1/89 (H1N2) (see, e.g., Karasin et al., 2002), swine influenza virus strain A/Swine/Wisconsin/1915/88 (H1N1) (see, e.g., Karasin et al., 2002), swine influenza virus strain A/Swine/Iowa/17672/88 (H1N1) (see, e.g., Karasin et al., 2002), swine influenza virus strain A/Swine/Tennessee/24/77 (H1N1) (see, e.g., Karasin et al., 2002), swine influenza virus strain A/Swine/Ontario/2/81 (H1N1) (see, e.g., Karasin et al., 2002), swine influenza virus strain A/Swine/Wisconsin/1/67 (H1N1) (see, e.g., Karasin et al., 2002), swine influenza virus strain A/Swine/Italy/1521/98 (H1N2) (see, e.g., Marozin et al., 2002), swine influenza virus strain A/Swine/Italy/839/89 (H1N1) (see, e.g., Karasin et al., 2002), swine influenza virus strain A/Swine/Hong Kong/126/82 (H3N2) (see, e.g., Karasin et al., 2002), influenza virus strain A/Idaho/4/95 (H3N2) (see, e.g., Karasin et al., 2002), influenza virus strain A/Johannesburg/33/94 (H3N2) (see, e.g., Karasin et al., 2002; Johansson et al., 1998), influenza virus strain A/Bangkok/1/79 (H3N2) (see, e.g., Karasin et al., 2002; Nelson et al., 2001), influenza virus strain A/Jdorn/72 (H3N2) (see, e.g., Karasin et al., 2002; Markoff et al., 1982), influenza virus strain A/Hokkaido/2/92 (H1N1) (see, e.g., Karasin et al., 2002), influenza virus strain A/Thailand/KAN-1/04 (see, e.g., Puthavathana et al., 2005; Amonsin et al., 2006), influenza virus strain A/England/1/53 (see, e.g., Govorkova E A, et al., 1995), influenza virus strain A/Vietnam/3046/2004 (H5N1), (see, e.g., Anwar et al., 2006), influenza virus strain A/Vietnam/1203/2004 (H5N1), (see, e.g., Anwar et al., 2006; Gao et al., 2006), influenza virus strain A/tiger/Thailand/SPB-1 (H5N1), (see, e.g., Anwar et al., 2006), influenza virus strain A/Japan/305/57 (H2N2) (see, e.g., Naeve et al., 1990; Brown et al., 1982), influenza virus strain A/Adachi/2/57 (H2N2) (see, e.g., Gething et al., 1980), influenza virus strain A/Camel/Mongolia/82 (H1N1) (see, e.g., Yamnikova et al., 1993), influenza virus strain A/R1/5/57 (H2N2) (see, e.g., Elleman et al., 1982), influenza virus strain A/Whale/Maine/1/84 (H13N9) (see, e.g., Air et al., 1987), influenza virus strain A/Taiwan/1/86 (H1N1) (see, e.g., Karasin et al., 2002; Brown, 1988), influenza virus strain A/Bayern/7/95 (H1N1) (see, e.g., Karasin et al., 2002), influenza virus strain A/USSR/90/77 (H1N1) (see, e.g., Karasin et al., 2002; Iftimovici et al., 1980), influenza virus strain A/Wuhan/359/95 (H3N2) (see, e.g., Karasin et al., 2002; Hardy et al., 2001), influenza virus strain A/Hong Kong/5/83 (H3N2) (see, e.g., Karasin et al., 2002), influenza virus strain A/Memphis/8/88 (H3N2) (see, e.g., Karasin et al., 2002; Hatta et al., 2002), influenza virus strain A/Beijing/337/89 (H3N2) (see, e.g., Karasin et al., 2002), influenza virus strain A/Shanghai/6/90 (H3N2) (see, e.g., Karasin et al., 2002), influenza virus strain A/Akita/1/94 (H3N2) (see, e.g., Karasin et al., 2002), influenza virus strain A/Akita/1/95 (H3N2) (see, e.g., Karasin et al., 2002), influenza virus strain A/Memphis/6/90 (H3N2) (see, e.g., Karasin et al., 2002), influenza virus strain AAUdom/307/72 (H3N2) (see, e.g., Karasin et al., 2002; Tuferov et al., 1984), influenza virus strain A/Singapore/1/57 (H2N2) (see, e.g., Karasin et al., 2002; Zhukova et al., 1975), influenza virus strain A/Ohio/4/83 (H1N1) (see, e.g., Karasin et al., 2002), influenza virus strain Madin Darby Canine Kidney (MDCK) -derived cell line (see, e.g., Halperin et al., 2002), mouse-adapted influenza virus strain A/Guizhou/54/89 (H3N2 subtype) (see, e.g., Nagai et al., 1995), mouse-adapted influenza virus A/PR/8/34 (A/PR8) (see, e.g., Nagai et al., 1995), mouse-adapted influenza virus B/Ibaraki/2/85 (see, e.g., Nagai et al., 1995), Russian live attenuated influenza vaccine donor strains A/Leningrad/134/17/57, A/Leningrad/134/47/57 and B/USSR/60/69 (see, e.g., Audsley et al. 2005), the disclosures of which are incorporated by reference.

In another advantageous embodiment, the avian influenza polypeptide, antigen, epitope or immunogen may be derived from an avian infected with influenza or an avian influenza strain derived from a recent isolate.

In one advantageous embodiment, the influenza vaccine comprises one or more influenza polypeptide, antigen, epitope or immunogen, wherein the influenza isolate is selected from one or more strain of influenza. In one embodiment, the influenza vaccine comprises one or more influenza isolates chosen from the group consisting of a feline influenza isolate, an avian influenza isolate, or mixtures thereof. In yet another embodiment, the influenza vaccine comprises one or more influenza isolates chosen from the group consisting of an inactivated feline influenza isolate, an inactivated avian influenza isolate, or mixtures thereof.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin.

The term "immunogenic protein or peptide" as used herein also refers includes peptides and polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. The term epitope relates to a protein site able to induce an immune reaction of the humoral type (B cells) and/or cellular type (T cells).

The term "immunogenic protein or peptide" further contemplates deletions, additions and substitutions to the sequence, so long as the polypeptide functions to produce an immunological response as defined herein. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "immunogenic" protein or polypeptide as used herein also refers to an amino acid sequence which elicits an immunological response as described above. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of T. parva are fully described in the PCT Application Serial No. PCT/US2004/022605 incorporated herein by reference in its entirety.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, preferably at least about 5 amino acids, more preferably at least about 10-15 amino acids, and most preferably about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides to encode an epitope or antigenic determinant of an influenza protein or polyprotein. A polynucleotide encoding a fragment of the total protein or polyprotein, more advantageously, comprises or consists essentially of or consists of a minimum of 15 nucleotides, at least 15-30, advantageously about 30-45 nucleotides, and preferably about 45-75, at least 57, 87 or 150 consecutive or contiguous nucleotides of the sequence encoding the total protein or polyprotein. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin.®. Peptide Synthesis Kits de Chiron) and algorithms (De Groot et al., 1999), and in PCT Application Serial No. PCT/US2004/022605 all of which are incorporated herein by reference in their entireties, can be used in the practice of the invention, without undue experimentation. Other documents cited and incorporated herein may also be consulted for methods for determining epitopes of an immunogen or antigen and thus nucleic acid molecules that encode such epitopes.

A "polynucleotide" is a polymeric form of nucleotides of any length, which contain deoxyribonucleotides, ribonucleotides, and analogs in any combination. Polynucleotides may have three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The invention further comprises a complementary strand to a polynucleotide encoding an influenza antigen, epitope or immunogen. The complementary strand can be polymeric and of any length, and can contain deoxyribonucleotides, ribonucleotides, and analogs in any combination.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

An "isolated" polynucleotide or polypeptide is one that is substantially free of the materials with which it is associated in its native environment. By substantially free, is meant at least 50%, advantageously at least 70%, more advantageously at least 80%, and even more advantageously at least 90% or at least 95% free of these materials.

Hybridization reactions can be performed under conditions of different "stringency." Conditions that increase stringency of a hybridization reaction are well known. See for example, "Molecular Cloning: A Laboratory Manual", second edition (Sambrook et al., 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of the influenza polypeptides and functionally equivalent fragments thereof which may enhance, decrease or not significantly affect properties of the polypeptides encoded thereby. These functionally equivalent variants, derivatives, and fragments display the ability to retain influenza activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the influenza polynucleotide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin et al., 1990 modified as in Karlin et al., 1993.

Another example of a mathematical algorithm used for comparison of sequences is the algorithm of Myers et al., 1988. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson et al., 1988.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul et al., 1996; Altschul et al., 1990; Gish et al., 1993; Karlin et al., 1993; all of which are incorporated by reference herein).

In general, comparison of amino acid sequences is accomplished by aligning an amino acid sequence of a polypeptide of a known structure with the amino acid sequence of a the polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})*100/N_{ref}$ wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur et al., 1983, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

And, without undue experimentation, the skilled artisan can consult with many other programs or references for determining percent homology.

The invention further encompasses the influenza polynucleotides contained in a vector molecule or an expression vector and operably linked to a promoter element and optionally to an enhancer.

The vector is advantageously a poxvirus, particularly a vaccinia virus or an avipox virus, such as fowlpox virus or canarypox virus. Advantageously, the virus is a fowlpox virus. An advantageous fowlpox strain may be an attenuated strain. The vector can express at least one epitope from avian strains. Advantageous fowlpox constructs include, but are not limited to, vFP89 and vFP2211. Alternatively, the virus is advantageously a canarypox virus. Advantageous canarypox strains may be an attenuated strain. The vector can express at least one epitope of an avian strain. An advantageous canarypox construct includes, but is not limited to, vCP2241. Recombinant avipox viruses (see, e.g., U.S. Pat. Nos. 5,505, 941 and 5,756,103), such as an attenuated recombinant fowlpox virus, for instance TROVAC (available under ATCC accession number VR-2553), or an attenuated canarypox virus, for instance ALVAC (available under ATCC accession number VR-2547), are especially advantageous. In one advantageous embodiment, the recombinant TROVAC vaccine described by Karaca et al., 2005, the disclosure of which is incorporated by reference, may be used as a feline influenza immunological composition or vaccine. Other viruses that may be used in methods of the invention include, but are not limited to, vaccinia viruses, such as an attenuated vaccinia virus, for instance NYVAC (available under ATCC accession number VR-2259), adenoviruses, such as canine adenoviruses (CAV), and herpesviruses, such as canine herpesvirus (CHV) or a feline herpesvirus (FHV).

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors also included are viral vectors.

The term "recombinant" means a polynucleotide semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of an influenza polypeptide, antigen, epitope or immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. an influenza peptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745, 051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450, 6,312,683, and 6,596,279; U.S. patent application Ser. No. 920,197, filed Oct. 16, 1986; WO 90/01543; WO91/11525; WO 94/16716; WO 96/39491; WO 98/33510; EP 265785; EP 0 370 573; Andreansky et al., 1996; Ballay et al., 1993; Felgner et al., 1994; Frolov et al., 1996; Graham, 1990; Grunhaus et al., 1992; Ju et al., 1998; Kitson et al., 1991; McClements et al., 1996; Moss, 1996; Paoletti, 1996; Pennock et al., 1984; Richardson (Ed), 1995; Smith et al., 1983; Robertson et al., 1996; Robinson et al., 1997; and Roizman, 1996. Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., human adenovirus, canine adenovirus), herpesvirus (e.g. canine herpesvirus), baculovirus, retrovirus, etc. (as in documents incorporated herein by reference); or the vector can be a plasmid. The herein cited and incorporated herein by reference documents, in addition to providing examples of vectors useful in the practice of the invention, can also provide sources for non-influenza peptides or fragments thereof to be expressed by vector or vectors in, or included in, the compositions of the invention.

The present invention also relates to preparations comprising vectors, such as expression vectors, e.g., therapeutic compositions. The preparations can comprise, consist essentially of, or consist of one or more vectors, e.g., expression vectors, such as in vivo expression vectors, comprising, consisting essentially or consisting of (and advantageously expressing) one or more of influenza polypeptides, antigens, epitopes or immunogens. Advantageously, the vector contains and expresses a polynucleotide that includes, consists essentially of, or consists of a polynucleotide coding for (and advantageously expressing) an influenza antigen, epitope or immunogen, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of an influenza polypeptide, antigen, epitope or immunogen (e.g., hemagglutinin, neuraminidase, nucleoprotein) or a fragment thereof.

According to another embodiment, the vector or vectors in the preparation comprise, or consist essentially of, or consist of polynucleotide(s) encoding one or more proteins or fragment(s) thereof of an influenza polypeptide, antigen, epitope or immunogen, the vector or vectors expressing the polynucleotide(s). The inventive preparation advantageously comprises, consists essentially of, or consists of, at least two vectors comprising, consisting essentially of, or consisting of, and advantageously also expressing, advantageously in vivo under appropriate conditions or suitable conditions or in a suitable host cell, polynucleotides from different feline influenza isolates encoding the same proteins and/or for different proteins, but advantageously the same proteins. Preparations containing one or more vectors containing, consisting essentially of or consisting of polynucleotides encoding, and advantageously expressing, advantageously in vivo, an influenza polypeptide, antigen, fusion protein or an epitope thereof. The invention is also directed at mixtures of vectors that contain, consist essentially of, or consist of coding for, and express, different influenza polypeptides, antigens, epitopes or immunogens, e.g., an influenza polypeptide, antigen, epitope or immunogen from different species such as, but not limited to, humans, horses, pigs, in addition to avian species including chicken, ducks and geese.

According to one embodiment of the invention, the expression vector is a viral vector, in particular an in vivo expression vector. In an advantageous embodiment, the expression vector is an adenovirus vector. Advantageously, the adenovirus is a human Ad5 vector, an E1-deleted and/or an E3-deleted adenovirus.

In one particular embodiment the viral vector is a poxvirus, e.g. a vaccinia virus or an attenuated vaccinia virus, (for instance, MVA, a modified Ankara strain obtained after more than 570 passages of the Ankara vaccine strain on chicken embryo fibroblasts; see Stickl et al., 1971; Sutter et al., 1992; available as ATCC VR-1508; or NYVAC, available under VR-2259, see U.S. Pat. No. 5,494,807, for instance, Examples 1 to 6 and et seq of U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO96/40241), an avipox virus or an attenuated avipox virus (e.g., canarypox, fowlpox, dovepox, pigeonpox, quailpox, ALVAC, available under VR-2547, or TROVAC; available under VR-2553, see, e.g., U.S. Pat. Nos. 5,505,941, 5,494,807), swinepox, raccoonpox, camelpox, or myxomatosis virus.

According to another embodiment of the invention, the poxvirus vector is a fowlpox virus or a canarypox virus vector, advantageously an attenuated fowlpox virus or canarypox virus. In this regard, attenuated fowlpox viruses are available, such asDIFTOSEC CT strain marketed by MERIAL and the NOBILIS VARIOLE vaccine marketed by INTERVET. Attenuated fowlpox viruses are described in U.S. Pat. No. 5,766,599 which pertains to the attenuated fowlpox strain TROVAC. Canarypox viruses are also available from the ATCC under access number VR-111, and are described in U.S. Pat. No. 5,756,103 (ALVAC) and WO01/05934.

For information on the method to generate recombinants thereof and how to administer recombinants thereof, the skilled artisan can refer documents cited herein and to WO90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and U.S. Pat. No. 5,766,599 inter alia; as to canarypox mentionis made of U.S. Pat. No. 5,756,103 inter alia; as to swinepox mention is made of U.S. Pat. No. 5,382,425 inter alia; and, as to raccoonpox, mention is made of WO00/03030 inter alia.

When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of fowlpox, advantageously the insertion site or sites are ORFs F7 and/or F8; see also documents cited herein, especially those pertaining to fowlpox virus. In the case of canarypox, advantageously the insertion site or sites are ORF(s) C3, C5 and/or C6; see also documents cited herein, especially those pertaining to canarypox virus. The insertion site or sites for MVA virus area advantageously as in various publications, including Carroll et al., 1997; Stittelaar et al., 2000; Sutter et al., 1994; and, in this regard it is also noted that the complete MVA genome is described in Antoine, 1998, which enables the skilled artisan to use other insertion sites or other promoters.

Advantageously, the polynucleotide to be expressed is inserted under the control of a specific poxvirus promoter, e.g., the vaccinia promoter 7.5 kDa (Cochran et al., 1985), the vaccinia promoter 13L (Riviere et al., 1992), the vaccinia promoter HA (Shida, 1986), the cowpox promoter ATI (Funahashi et al., 1988), the vaccinia promoter H6 (Taylor et al., 1988b; Guo et al., 1989; Perkus et al., 1989), inter alia.

In a particular embodiment the viral vector is an adenovirus, such as a human adenovirus (HAV) or a canine adenovirus (CAV).

In one embodiment the viral vector is a human adenovirus, in particular a serotype 5 adenovirus, rendered incompetent for replication by a deletion in the E1 region of the viral genome, in particular from about nucleotide 459 to about nucleotide 3510 by reference to the sequence of the hAd5 disclosed in Genbank under the accession number M73260 and in the referenced publication Chroboczek et al, 1992. The deleted adenovirus is propagated in E1-expressing 293 (Graham et al., 1977) or PER cells, in particular PER.C6 (Falloux et al., 1998). The human adenovirus can be deleted in the E3 region, in particular from about nucleotide 28592 to about nucleotide 30470. The deletion in the E1 region can be done in combination with a deletion in the E3 region (see, e.g. Shriver et al., 2002; Graham et al., 1991; Ilan et al., 1997; U.S. Pat. Nos. 6,133,028 and 6,692,956; Tripathy et al., 1994; Tapnell, 1993; Danthinne et al., 2000; Berkner, 1988; Berkner et al., 1983; Chavier et al., 1996). The insertion sites can be the E1 and/or E3 loci (region) eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, preferably a cytomegalovirus immediate-early gene promoter (CMV-IE promoter), in particular the enhancer/promoter region from about nucleotide −734 to about nucleotide +7 in Boshart et al., 1985 or the enhancer/promoter region from the pCI vector from Promega Corp. The CMV-IE promoter is advantageously of murine or human origin. The promoter of the elongation factor 1 a can also be used. A muscle specific promoter can also be used (Li et al., 1999). Strong promoters are also discussed herein in relation to plasmid vectors. In one embodiment, a splicing sequence can be located downstream of the enhancer/promoter region. For example, the intron 1 isolated from the CMV-IE gene (Stenberg et al., 1984), the intron isolated from the rabbit or human β-globin gene, in particular the intron 2 from the b-globin gene, the intron isolated from the immunoglobulin gene, a splicing sequence from the SV40 early gene or the chimeric intron sequence isolated from the pCI vector from Promege Corp. comprising the human β-globin gene donor sequence fused to the mouse immunoglobulin acceptor sequence (from about nucleotide 890 to about nucleotide 1022 in Genbank under the accession number CVU47120). A poly(A) sequence and terminator sequence can be inserted downstream the polynucleotide to be expressed, e.g. a bovine growth hormone gene, in particular from about nucleotide 2339 to about nucleotide 2550 in Genbank under the accession number BOVGHRH, a rabbit β-globin gene or a SV40 late gene polyadenylation signal.

In another embodiment the viral vector is a canine adenovirus, in particular a CAV-2 (see, e.g. Fischer et al., 2002; U.S. Pat. Nos. 5,529,780 and 5,688,920; PCT Application No. WO95/14102). For CAV, the insertion sites can be in the E3 region and/or in the region located between the E4 region and the right ITR region (see U.S. Pat. Nos. 6,090,393 and 6,156,567). In one embodiment the insert is under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another particular embodiment the viral vector is a herpesvirus such as a canine herpesvirus (CHV) or a feline herpesvirus (FHV). For CHV, the insertion sites may be in particular in the thymidine kinase gene, in the ORF3, or in the UL43 ORF (see U.S. Pat. No. 6,159,477). In one embodiment the polynucleotide to be expressed is inserted under the control of a promoter functional in eukaryotic cells, advantageously a CMV-IE promoter (murine or human). A poly(A) sequence and terminator sequence can be inserted downstream the polynucleotide to be expressed, e.g. bovine growth hormone or a rabbit β-globin gene polyadenylation signal.

According to a yet further embodiment of the invention, the expression vector is a plasmid vector or a DNA plasmid vector, in particular an in vivo expression vector. In a specific, non-limiting example, the pVR1020 or 1012 plasmid (VICAL Inc.; Luke et al., 1997; Hartikka et al., 1996, see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070. Additional information on DNA plasmids which may be consulted or employed in the practice are found, for example, in U.S. Pat. Nos. 6,852,705; 6,818, 628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding an influenza antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart et al., 1985) or murine CMV-IE.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Preferably, the plasmids comprise or consist essentially of other expression control elements. It is particularly advantageous to incorporate stabilizing sequence(s), e.g., intron sequence(s), preferably the first intron of the hCMV-IE (PCT Application No. WO89/01036), the intron II of the rabbit β-globin gene (van Ooyen et al., 1979).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof. Advantageous host cells include, but are not limited to, baby hamster kidney (BHK) cells, colon carcinoma (Caco-2) cells, COS7 cells, MCF-7 cells, MCF-10A cells, Madin-Darby canine kidney (MDCK) lines, mink lung (Mv1Lu) cells, MRC-5 cells, U937 cells, CHO cells, and VERO cells. Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

In an advantageous embodiment, the invention provides for the administration of a therapeutically effective amount of a formulation for the delivery and expression of an influenza antigen, epitope or immunogen in a target cell. Determination of the therapeutically effective amount is routine experimentation for one of ordinary skill in the art. In one embodiment, the formulation comprises an expression vector comprising a polynucleotide that expresses an influenza antigen, epitope or immunogen and a pharmaceutically or veterinarily acceptable carrier, vehicle or excipient. In an advantageous embodiment, the pharmaceutically or veterinarily acceptable carrier, vehicle or excipient facilitates transfection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

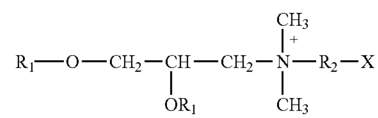

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N -dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95: about 5 to about 5: about 95, more advantageously about 1: about 1, e.g., 1:1.

The DMRIE or DMRIE-DOPE adjuvant:plasmid weight ratio can be between about 50: about 1 and about 1: about 10, such as about 10: about 1 and about 1 about 5, and advantageously about 1: about 1 and about 1: about 2, e.g., 1:1 and 1:2.

The invention also provides for inactivated feline influenza immunological compositions or vaccines. As used herein, the term "inactivated immunological composition" or "inactivated vaccine" means a immunological composition or vaccine containing an infectious organism or pathogen that is no longer capable of replication or growth. Inactivation may be accomplished by a variety of methods sufficient to prevent replication or growth of the organism while maintaining its immunogenicity.

The inactivated immunological composition or vaccine may be an inactivated form of an isolate of an influenza virus from an affected cat. The virus may be isolated from the alveoli or lung of an affected cat. In another embodiment, the inactivated immunological composition or vaccine may be an inactivated avian influenza. The inactivated immunological composition or vaccine may be an inactivated version of any one of the influenza strains described above.

An inactivated immunological composition or vaccine may be prepared as well from the harvested culture fluid. The virus may be produced either by inoculation of 10-11-day embryonated eggs (U.S. Pat. No. 6,048,537) or by inoculation of BHK-21 cell culture (Ross et al., 1970; Tolstova et al., 1966; Merten et al., 1996), of MDCK cell culture (Tree et al., 2001; Ghendon et al., 2005; Brands et al., 1999; Youil et al., 2004), of Vero cell culture (Kistner et al., 1998; Govorkova et al., 1996). The allantoic fluid or the cell culture supernatant can be clarified by low centrifugation and/or filtration. The virus can be concentrated by ultrafiltration and can be purified by zonal centrifugation on sucrose gradient (U.S. Pat. No. 6,048,537; O. Kistner et al. idem), by gel filtration (Nayak et al., 2005; Tomita et al., 1971).

Inactivation may be achieved by treating the viruses by any of the methods commonly employed to make inactivated immunological compositions or vaccines. These methods include but are not limited to formaldehyde treatment (O. Kistner et al. idem; Garcia et al., 1998), betapropriolactone treatment (Budowsky et al., 1991; Budowsky et al., 1993; Keverin et al., 2000), ethylene-imine treatment (Swayne et al., 2001), treatment with organic solvents, treatment with detergents, treatment with Tween-ether or treatment with Triton X-100 (J. Vilay et al. idem) for allantoic fluid. For the inactivation the concentration can be about 0.01-0.2% w/v for the formaldehyde; about 0.03-0.2% w/v for the betapropiolactone; about 0.5-20 mM for ethyleneimine. The methods recited herein serve as art-known examples for inactivating virus. Inactivated virus immunological compositions or vaccines are usually administered mixed with an adjuvant. The inactivated immunological composition or vaccine can be administered to the animal by any of a plurality of methods which include but are not limited to inoculation intramuscularly or subcutaneously, spraying, ocularly, nasally, orally, or in ovo.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one ore more nonmethylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., 1960.

With regard to structure, the acrylic or methacrylic acid polymers and EMA are preferably formed by basic units having the following formula:

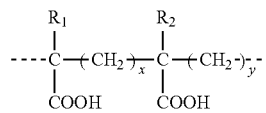

in which:
R1 and R2, which can be the same or different, represent H or CH3
x=0 or 1, preferably x=1
y=1 or 2, with x+y=2.
For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between 0.01 and 1.5% w/v, advantageously 0.05 to 1% w/v and preferably 0.1 to 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector therefor.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α(IFNα), interferon β(IFNβ), interferon γ, (IFNγ), interleukin-1α(IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α(TNFα), tumor necrosis factor β(TNFβ), and transforming growth factor β(TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a feline cytokine for preparations to be administered to felids).

Advantageously, the immunological composition and/or vaccine according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

In the case of immunological composition and/or vaccine based on a plasmid vector, a dose can comprise, consist essentially of or consist of, in general terms, about in 1 μg to about 2000 μg. advantageously about 50 μg to about 1000 μg and more advantageously from about 100 μg to about 800 μg of plasmid expressing the influenza antigen, epitope or immunogen. When immunological composition and/or vaccine based on a plasmid vector is administered with electroporation the dose of plasmid is generally between about 0.1 μg and 1 mg, advantageously between about 1 μg and 100 μg, advantageously between about 2 μg and 50 μg. The dose volumes can be between about 0.1 and about 2 ml, advantageously between about 0.2 and about 1 ml. These doses and dose volumes are suitable for the treatment of felines.

The immunological composition and/or vaccine contains per dose from about $10^4$ to about $10^{11}$, advantageously from about $10^5$ to about $10^{10}$ and more advantageously from about $10^6$ to about $10^9$ viral particles of recombinant adenovirus expressing an influenza antigen, epitope or immunogen. In the case of immunological composition and/or vaccine based on a poxvirus, a dose can be between about $10^2$ pfu and about $10^9$ pfu. The immunological composition and/or vaccine contains per dose from about $10^5$ to $10^9$, advantageously from about $10^6$ to $10^8$ pfu of poxvirus or herpesvirus recombinant expressing the influenza antigen, epitope or immunogen.

The dose volume of compositions for target species that are mammals, e.g., the dose volume of feline compositions, based on viral vectors, e.g., non-poxvirus-viral-vector-based compositions, is generally between about 0.1 to about 2.0 ml, preferably between about 0.1 to about 1.0 ml, and more preferably between about 0.5 ml to about 1.0 ml.

In one embodiment of the invention, a prime-boost regimen can be employed, which is comprised of at least one primary administration and at least one booster administration using at least one common polypeptide, antigen, epitope or immunogen. The immunological composition or vaccine used in primary administration is different in nature from those used as a booster. This administration protocol is called "prime-boost". The prime-boost protocol according to the invention comprises a primary administration with an immunological composition or vaccine comprising, in a pharmaceutically acceptable vehicle or excipient, a plasmid containing a polynucleotide sequence for expressing, in vivo, an avian influenza polypeptide, antigen, epitope or immunogen, followed by a booster with an immunogical composition or vaccine, or a recombined immunological composition or vaccine comprising, in a pharmaceutically acceptable vehicle or excipient, a viral vector containing a polynucleotide sequence for expressing, in vivo, an avian influenza polypeptide antigen, epitope or immunogen, with the condition according to which at least one of the polypeptides, antigens, epitopes or immunogens is encoded by both the plasmids and the viral vectors. Alternatively, the booster can be comprised of an inactivated immunological composition or vaccine. In another alternative embodiment, the avian influenza polypeptide antigen, epitope or immunogen of the primary administration may derive from a different avian influenza strain than the avian influenza polypeptide antigen, epitope or immunogen of the booster administration The primary administration may comprise one or more administrations of the same plasmid-based immunological compositions of vaccines. Similarly, the booster administration may comprise one or more administrations of the same viral vector-based immunological composition of vaccine. According to a particular embodiment of the invention, the protocol comprises two successive administrations of the same plasmid-based immunological compositions of vaccines, and then one administration of a viral vector-based immunological composition of vaccine, as a booster. Alternatively, the primary administration may be a plasmid-based or viral vector-based immunological composition or vaccine, and the booster administration may be an inactivated immunological composition or vaccine.

The various administrations are preferably carried out 3 to 6 weeks apart, and more particularly about 4 weeks apart. According to a preferred mode, an annual booster, preferably using the viral vector-based immunological composition of vaccine, is also envisaged. The animals are preferably at least 6 to 8 weeks old at the time of the first administration.

With inactivated compositions of the virus or organism or pathogen produced on the new cell culture, the animal may be administered approximately $10^4$-$10^9$ equivalent CCID50 (titer before inactivation), advantageously approximately $10^5$-$10^8$ equivalent CCID50 in a single dosage unit. The volume of one single dosage unit can be between 0.2 ml and 5.0 ml and advantageously between 0.5 ml and 2.0 ml and more advantageously about 2.0 ml. One or more administrations can be done; e.g. with two injections at 2-4 weeks interval, and advantageously with a boost about 3 weeks after the first injection.

In an advantageous embodiment, an animal, advantageously a felid, is vaccinated with two doses of inactivated vaccine at about 3 to 4 week intervals via the subcuntaneous route, although an intramuscular route is also contemplated. Blood samples may be collected on the day of the first and/or second vaccination and about 2 to 10 weeks after the second vaccination to determine the levels of anti-influenza virus-specific antibodies by methods known to one of skill in the art, for example, virus neutralization, hemagglutination inhibition, ELISA, or single radial heamolysis (SRH) tests.

The efficacy of the inactivated vaccines may be tested about 2 to 4 weeks after the second immunization by challenging animals, advantageously felids, with a virulent strain of influenza, advantageously the influenza H5N1, H5N8 or H5N9 strains. The animal may be challenged by spray, intra-nassaly, intra-tracheally, orally, and/or by contact. The challenge viral may be about $10^{5-8}$ EID50 in a volume depending upon the route of administration. For example, if the administration is by spray, a virus suspension is aerosolized to generate about 1 to 100 μm droplets, if the administration is intra-nasal, intra-tracheal or oral, the volume of the challenge virus is about 0.5 ml, 1-2 ml, and 5-10 ml, respectively. Animals may be observed daily for 14 days following challenge for clinical signs, for example, fever, cough, nasal, ocular discharge, respiratory distress, anorexia, and lethargy. In addition, the groups of animals may be euthanized and evaluated for pathological findings of pulmonary and pleural hemorrhage, tracheitis, bronchitis, broncolilitis, and bronchopneumonia. Tracheal swabs may be collected from all animals post challenge days 1-14 for virus isolation. The presence or absence of viral antigens in respiratory tissues may be evaluated by immunohistochemistry, for example, on days 3, 7, and 10 post-challenge. Blood samples may be collected post-challenge (e.g., on days 7 and 14 post-challenge) and may be analyzed for the presence of anti-influenza H5N1 virus-specific antibody.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Dermojet, Biojector, Vetjet or Vitajet apparatus (Bioject, Oregon, USA)). Another approach to administer plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment. In an advantageous embodiment, the animal is a felid.

One embodiment of the invention is a method of eliciting an immune response against avian influenza virus in an animal, comprising administering a formulation for delivery and expression of a recombinant poxvirus influenza immunological composition or vaccine or inactivated influenza immunological composition or vaccine in an effective amount for eliciting an immune response. Still another embodiment of the invention is a method of inducing an immunological or a protective immune response against avian influenza virus in an animal, comprising administering to the animal an effective amount of a formulation for delivery and expression of an influenza antigen, epitope or immunogen wherein the formulation comprises recombinant poxvirus influenza immunological composition or vaccine or inactivated influenza immunological composition or vaccine and a pharmaceutically or veterinarily acceptable carrier, vehicle or excipient.

The invention relates to a method to elicit, induce or stimulate the immune response of an animal, advantageously a felid.

In one embodiment of the invention, the immune response elicited to induced is a protective immune response. As is accepted by those of skill in the art, a protective immune response is one that successfully protects a subject from challenge.

Another embodiment of the invention is a kit for performing a method of inducing an immunological or protective response against influenza in an animal comprising a recombinant influenza poxvirus immunological composition or vaccine or an inactivated influenza immunological composition or vaccine and instructions for performing the method of delivery in an effective amount for eliciting an immune response in the animal.

The invention will now be further described by way of the following non-limiting examples which further illustrate the invention, and are not intended, nor should they be interpreted to, limit the scope of the invention.

EXAMPLES

Example 1

Construction and Development of TROVAC AIV H5 (vFP89)

The construction of vFP89 disclosed herein Example 1 can be found in the following U.S. Pat. Nos. 5,494,807, 5,529,780, 5,688,920, 5,756,102, 5,756,103, 5,762,938, 5,766,599, 5,833,975, 5,863,542, 5,942,235, 6,017,542, 6,265,189, 6,309,647, 6,537,594, 6,596,279, and 6,780,407, the disclosures of which are incorporated by reference.

Development of Attenuated Fowlpox Virus

Plasmids containing cDNA clones of the H5 hemagglutinin gene was obtained from Dr. Robert Webster, St. Jude Children's Research Hospital, Memphis, Tenn. The strain of FPV designated FP-1 has been described previously (Taylor et al., 1988a, b). It is a vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chick embryo fibroblast (CEF) cells. This virus was obtained in September 1980 by Rhone Merieux, Lyon, France, and a master viral seed established. The virus was received by Virogenetics in September 1989, where it was subjected to four successive plaque purifications. One plaque isolate was further amplified in primary CEF cells and a stock virus, designated as TROVAC, was established. The stock virus used in the in vitro recombination test to produce TROVAC-AIV H5 (vFP89) and TROVAC -AIV H4 (vFP92) had been further amplified though 8 passages in primary CEF cells. The stock virus used to produce TROVAC-AIV H7 (vFP100) had been further amplified through 12 passages in primary CEF cells.

Construction of TROVAC Insertion Plasmid at F8 Locus.

Plasmid pRW731.15 contains a 10 kbp PvuII-PvuII fragment cloned from TROVAC genomic DNA. The nucleotide sequence was determined on both strands for a 3659 bp PvuII -EcoRV fragment. This sequence is shown in SEQ ID NO: 1. The limits of an open reading frame designated in this laboratory as F8 were determined within this sequence. The open reading frame is initiated at position 495 and terminates at position 1887. A deletion was made from position 779 to position 1926, as described below. With respect to plasmid pRW731.15, reference is made to U.S. Pat. Nos. 5,494,807, 5,529,780, 5,756,102, 5,756,103, 5,766,599, 5,833,975, and 6,596,279, the disclosures of which are incorporated by reference.

Plasmid pRW761 is a sub-clone of pRW731.15 containing a 2430 bp EcoRV-EcORV fragment. Plasmid pRW761 was completely digested with XbaI and partially digested with SspI. A 3700 bp XbaI-SspI band was isolated and ligated with the annealed double-stranded oligonucleotides JCA017 (SEQ ID NO: 2) and JCA018 (SEQ ID NO: 3). With respect to plasmid pRW761, reference is made to U.S. Pat. Nos. 5,494,807, 5,529,780, 5,756,102, 5,756,103, 5,766,599, 5,833,975, and 6,596,279, the disclosures of which are incorporated by reference.

```
                             JCA017 (SEQ ID NO: 2)
5' CTAGACACTTTATGTTTTTAATATCCGGTCTTAAA-
AGCTTCCCGGGGATCCTTATACGGGGAATAAT 3'

JCA018 (SEQ ID NO: 3)
5' ATTATTCCCCGTATAAGGATCCCCCGGGAAGCTTTT-
AAGACCGGATATTAAAAAACATAAAGTGT 3'
```

The plasmid resulting from this ligation was designated pJCA002. Plasmid pJCA004 contains a non-pertinent gene linked to the vaccinia virus H6 promoter in plasmid pJCA002. The sequence of the vaccinia virus H6 promoter has been previously described (Taylor et al., 1988a, b; Guo et al., 1989; Perkus et al., 1989). Plasmid pJCA004 was digested with EcoRV and BamHI which deletes the non-pertinent gene and a portion of the 3' end of the H6 promoter. Annealed oligonucleotides RW178 (SEQ ID NO: 4) and RW179 (SEQ ID NO: 5) were cut with EcoRV and BamHI and inserted between the EcoRV and BamHI sites of JCA004 to form pRW846. With respect to plasmids pJCA002, pJCA004, and pRW846, references are made to U.S. Pat. Nos. 5,494,807, 5,529,780, 5,756,102, 5,756,103, 5,766,599, 5,833,975, and 6,596,279, the disclosures of which are incorporated by reference.

```
RW178 (SEQ ID NO: 4):
5' TCATTATCGCGATATCCGTGTTAACTAGCTAGCTAA
TTTTTATTCCCGGGATCCTTATCA 3'

RW179 (SEQ ID NO: 5):
5' GTATAAGGATCCCGGGAATAAAAATTAGCTAGCTA
GTTAACACGGATATCGCGATAATGA 3'
```

Plasmid pRW846 therefore contains the H6 promoter 5' of EcoRV in the de-ORFed F8 locus. The HincII site 3' of the H6 promoter in pRW846 is followed by translation stop codons, a transcriptional stop sequence recognized by vaccinia virus early promoters (Yuen et al., 1987) and a SmaI site.

Construction of Insertion Plasmid for H5 Hemagglutinin at the F8 Locus in TROVAC A cDNA clone of avian influenza H5 derived from A/Turkey/Ireland/1378/83 was received in plasmid pTH29 from Dr. R. Webster. Synthetic oligonucleotides RW10 (SEQ ID NO: 6) through RW13 (SEQ ID NO: 9) were designed to overlap the translation initiation codon of the previously described vaccinia virus H6 promoter with the ATG of the H5 gene. The sequence continues through the 5' SalI site of the H5 gene and begins again at the 3' H5 DraI site containing the H5 stop codon.

```
RW10 (SEQ ID NO: 6)
5' GAAAAATTTAAAGTCGACCTGTTTTGTTGAGTTGTTT
GCGTGGTAACCAATGCAAATCTGGTCACT 3'

RW11 (SEQ ID NO: 7)
5' TCTAGCAAGACTGACTATTGCAAAAGAAGCACTAT
TTCCTCCATTACGATACAAACTTAACGGAT 3'

RW12 (SEQ ID NO: 8)
5' ATCCGTTAAGTTTGTATCGTAATGGAGGAAATAGTGC
TTCTTTTTGCAATAGTCAGTCTTGCTAGAAGTGACCAGATTTGCATTGGT
3'

RW13 (SEQ ID NO: 9)
5' TACCACGCAAACAACTCAACAAAACAGGTCGACTTTA
AATTTTTCTGCA 3'
```

The oligonucleotides were annealed at 95° C. for three minutes followed by slow cooling at room temperature. This results in the following double strand structure.

Cloning of oligonucleotides between the EcoRV and PstI sites of pRW742B resulted in pRW744. Plasmid pRW742B contains the vaccinia virus H6 promoter linked to a non-pertinent gene inserted at the HincI site of pRW731.15 described previously. Digestion with PstI and EcoRV eliminates the non-pertinent gene and the 3'-end of the H6 promoter. Plasmid pRW744 now contains the 3' portion of the H6 promoter overlapping the ATG of avian influenza H5. The plasmid also contains the H5 sequence through the 5' SalI site and the 3' sequence from the H5 stop codon (containing a DraI site). Use of the DraI site removes the H5 3' non-coding end. The oligonucleotides add a transcription termination signal recognized by early vaccinia virus RNA polymerase (Yuen et al., 1987). To complete the H6 promoted H5 construct, the H5 coding region was isolated as a 1.6 kpb SalI-DraI fragment from pTH29. Plasmid pRW744 was partially digested with DraI, the linear fragment isolated, recut with SalI and the plasmid now with eight bases deleted between SalI and DraI was used as a vector for the 1.6 kpb pTH29 SalI and DraI fragment. The resulting plasmid pRW759 was cut with EcoRV and DraI. The 1.7 kbp PRW759 EcoRV-DraI fragment containing the 3' H6 promoter and the H5 gene was inserted between the EcoRV and HincII sites of pRW846 (previously described). The resulting plasmid pRW849 contains the H6 promoted avian influenza virus H5 gene in the de-ORFed F8 locus. With respect to plasmids pRW742B, pRW744, pRW759, and pRW849, references are made to U.S. Pat. Nos. 5,494,807, 5,529,780, 5,756,102, 5,756,103, 5,766,599, 5,833,975, and 6,596,279, the disclosures of which are incorporated by reference.

Development of TROVAC-Avian Influenza Virus Recombinants.

Insertion plasmids containing the avian influenza virus HA coding sequences were individually transfected into TROVAC infected primary CEF cells by using the calcium phosphate precipitation method previously described (Panicali et al., 1982; Piccini et al., 1987). Positive plaques were selected on the basis of hybridization to HA specific radiolabelled probes and subjected to sequential rounds of plaque purification until a pure population was achieved. One representative plaque was then amplified to produce a stock virus. Plasmid pRW849 was used in an in vitro recombination test to produce recombinant TROVAC-AIV H5 (vFP89) expressing the H5 hemagglutinin.

Determination of H5 Expression Using Immunofluorescence.

In influenza virus infected cells, the HA molecule is synthesized and glycosylated as a precursor molecule at the rough endoplasmic reticulum. During passage to the plasma membrane it undergoes extensive post-translational modification culminating in proteolytic cleavage into the disulphide linked HA.sub.1 and HA.sub.2 subunits and insertion into the host cell membrane where it is subsequently incorporated into mature viral envelopes. To determine whether the HA molecules produced in cells infected with the TROVAC-AIV recombinant viruses were expressed on the cell surface, immunofluorescence studies were performed. Indirect immunofluorescence was performed as described (Taylor et al., 1990). Surface expression of the H5 hemagglutinin in TROVAC-AIV H5 was confirmed by indirect immunofluorescence. Expression of the H5 hemagglutinin was detected using a pool of monoclonal antibodies specific for the H5 HA. Characterization of H5 Using Immunoprecipitation.

It has been determined that the sequence at and around the cleavage site of the hemagglutinin molecule plays an important role in determining viral virulence since cleavage of the hemagglutinin polypeptide is necessary for virus particles to be infectious. The hemagglutinin protein of the virulent H5 possesses more than one basic amino acid at the carboxy terminus of HA1. It is thought that this allows cellular proteases which recognize a series of basic amino acids to cleave the hemagglutinin and allow the infectious virus to spread both in vitro and in vivo.

In order to determine that the hemagglutinin molecules expressed by the TROVAC recombinant was authentically processed, immunoprecipitation experiments were performed as described (Taylor et al., 1990) using the specific reagents described above.

Immunoprecipitation analysis of the H5 hemagglutinin showed that the glycoprotein is evident as the two cleavage products HA.sub.1 and HA.sub.2 with approximate molecular weights of 44 and 23 kDa, respectively. No such proteins were precipitated from uninfected cells or cells infected with parental TROVAC. Generation of recombinant virus by recombination, in situ hybridization of nitrocellulose filters and screening for B-galactosidase activity are as previously described (Panicali et al., 1982; Perkus et al., 1989).

Example 2

Construction and Development of TROVAC AIV H5 (vFP2211)

AIV H5 HA Gene

The nucleotide sequence used in the construction of vFP2211 was derived from AIV A/Chicken/Indonesia/03H5 HA gene supplied by GeneArt GmbH (Regensburg, Germany). The sequence is synthetic with codon optimization for expression in avian cells and with a modification of HA cleavage site (SEQ ID NO: 15, SEQ ID NO: 16).

Plasmid Construction of pJY1394.1

To construct the donor plasmid pF8 AIV synthetic H5 HA without cleavage site (pJY1394.1), plasmid pRW744 (see Example 1) was partially digested with DraI. The linear fragment was isolated, recut with SalI, and the plasmid now with 8 bases deleted between SalI and DraI was used as a vector for the insertion of the double stranded SalI and DraI fragment comprising the synthetic AIV H5 HA without cleavage site. The resulting plasmid was cut with EcoRV and DraI, providing a 1.8 kbp EcoRV-DraI fragment containing the 3' H6 promoter and the H5 HA gene. This fragment was inserted between the EcoRV and HincII sites of a donor plasmid based on pRW846 (see Example 1). The resulting plasmid pJY1394.1 contains the vaccinia H6 promoter followed by the synthetic codon-optimized/cleavage site deleted avian influenza virus A/chicken/Indonesia/03H5 HA gene in the de-ORFed F8 locus. With respect to plasmids pRW744 and pRW846, references are made to U.S. Pat. Nos. 5,494,807, 5,529,780, 5,756,102, 5,756,103, 5,766,599, 5,833,975, and 6,596,279, the disclosures of which are incorporated by reference.

Generation of TROVAC AIV H5 Recombinants vFP2211

To generate vFP2211, plasmid pJY1394.1, which contained the synthetic A/chicken/Indonesia/03H5 HA gene, was linearized with NotI restriction enzyme. The linearized fragments were individually transfected into TROVAC-infected primary CEF cells by using the calcium phosphate precipitation method described previously (Panicali et al. 1982; Piccini et al. 1987). After 42 h, the transfected-infected cells were harvested, sonicated and used for recombinant virus screening.

Recombinant plaques were screened based on the plaque lift hybridization method using an AIV-specific probe which was labeled with horse radish peroxidase according to the manufacturer's protocol (Amersham Cat# RPN-3000). After four sequential rounds of plaque purification, the recombinants, designated as vFP2211 and vFP2211, were generated. vFP2211 was confirmed by hybridization as 100% positive for the AIV insert and 100% negative for the F8 ORF.

The vFP2211 recombinants were expanded and concentrated to produce virus stock

Analysis of Recombinant vFP2211

To re-determine genetic purity, the stock of vFP2211 was re-confirmed by hybridization as 100% positive for the AIV probe and 100% negative for the F8 ORF. The stock of vFP2211 was re-confirmed by hybridization but found to be contaminated with the parental virus.

A theoretical restriction enzyme gel for the genomic DNA was created in Vector NTI and is shown in FIG. 3.

Figure 4:
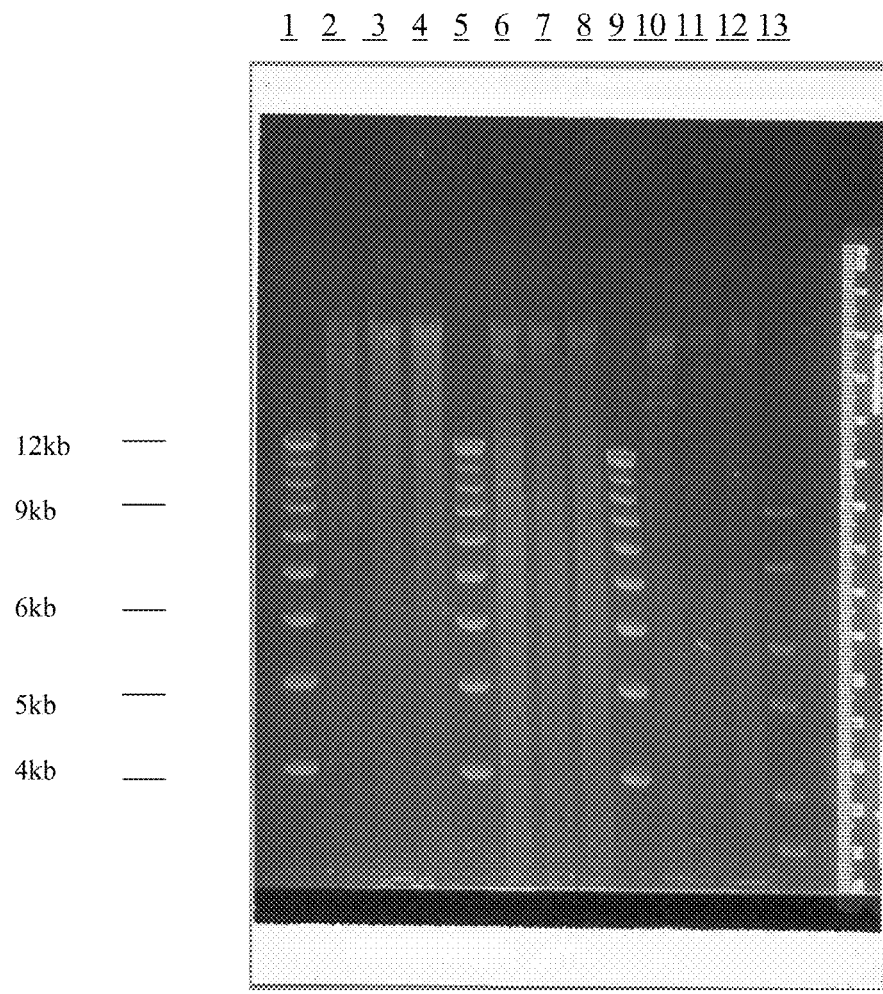
FIG. 4 illustrates a gel from electrophoresis of genomic DNA extracted from vFP2211 and digested with BamHI, Hind III, and Pst I.

Genomic DNA was extracted and digested with BamHI, HindIII and PstI. The genomic DNA was transferred to nylon membrane and analyses were performed by probing with an AIV probe (see FIG. 4). Bands were observed at the expected sizes, indicating the correct insertion of AIV into the F8 locus (see table 1)

TABLE 1

Size of the bands generated by digestion of genomic DNA with restriction enzymes.

| Restriction Enzymes | # of bp |
|---|---|
| BamHI | 23567 |
| HindIII | 17141 |
| PstI | 24376 |

Figure 5:
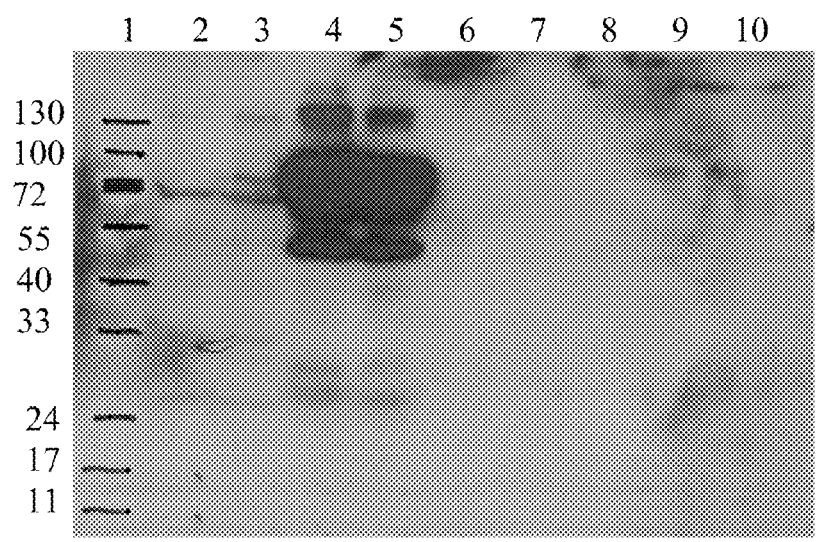
FIG. 5 illustrates a gel from Western blot analysis indicating the correct insertion of synthetic AIV H5 HA into the C5 locus.

Expression of the recombinant was examined through Western Blot Analysis. Primary CEF cells were infected with vFP2211 at MOI of 10 and incubated for 24 hours. The supernatant was harvested and clarified, and the cells were harvested and suspended in water to lyse. Lysate and supernatant were separated by 10% SDS-PAGE. The protein was transferred to nylon membrane and then incubated with HA-specific chicken polyserum TK/W1/68. The AIV-specific proteins were visualized using the Amersham ECL chemiluminescence detection system. The results indicated that the vFP2211 recombinants express the AIV HA genes in the cell lysates (see FIG. 5). There is no HA protein secretion into the supernatant.

Figure 6:
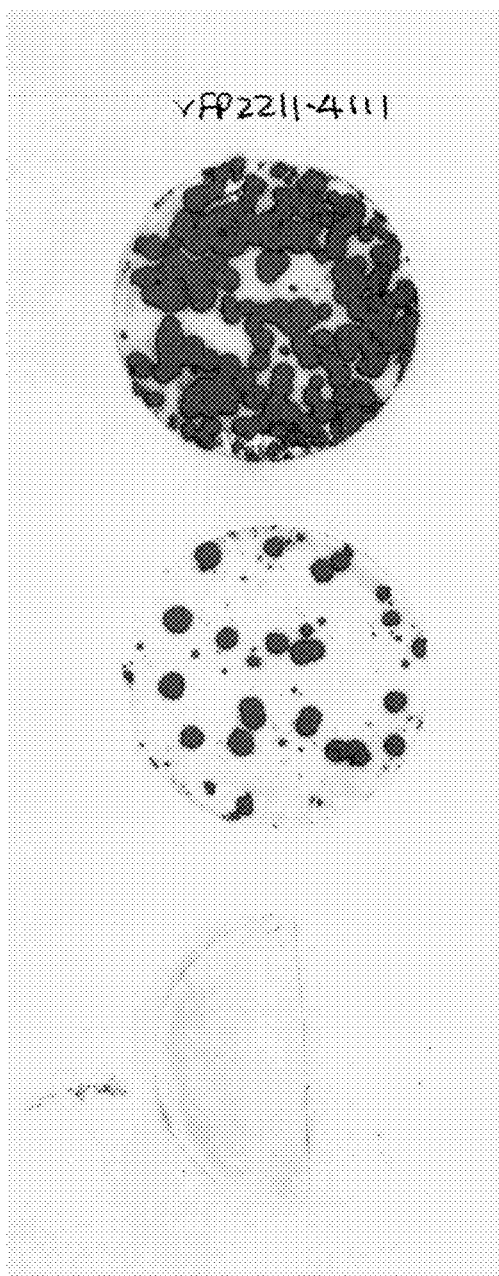
FIG. 6 illustrates the results of an immunoplaque assay of vFP2211, indicating that the homogeneity of the population was 100%.
Figure 12:
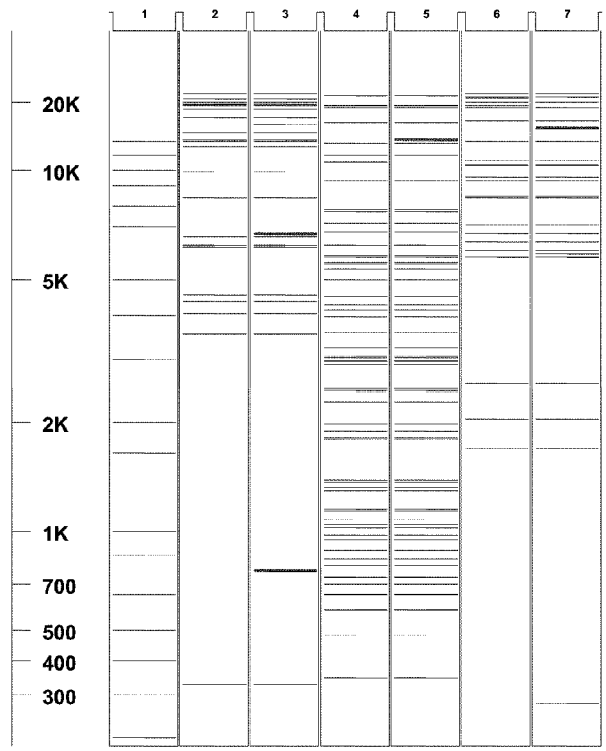
FIG. 12 illustrates a theoretical restriction enzyme gel for the genomic DNA of vCP2241.4.1.1.1.
Figure 13:
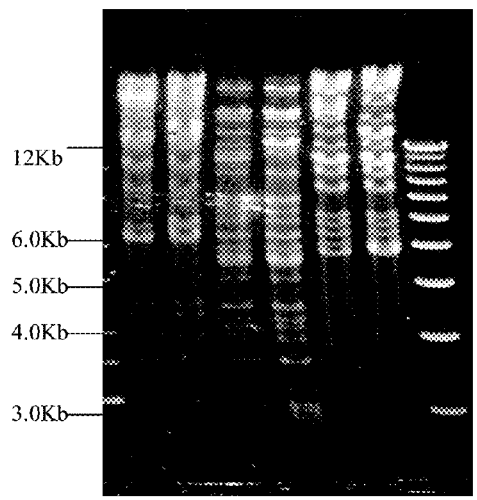
FIG. 13 illustrates a gel from electrophoresis of genomic DNA extracted from vCP2241.4.1.1.1 and digested with BamHI, Hind III, and Pst I.
Figure 14:
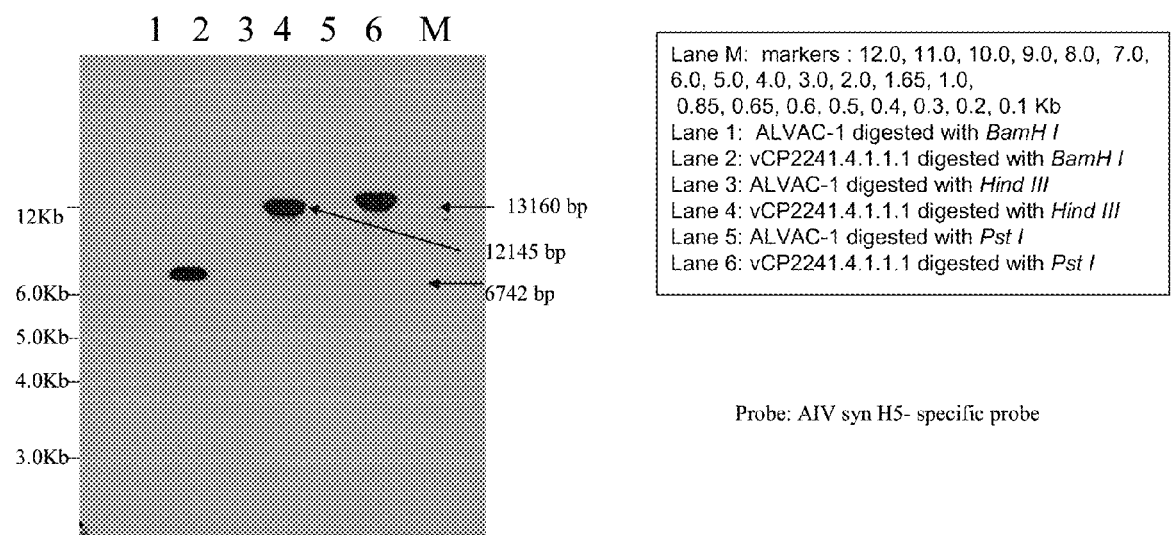
FIG. 14 illustrates a gel from Southern blot analysis indicating the expression of the H5 HA protein.
Figure 16:
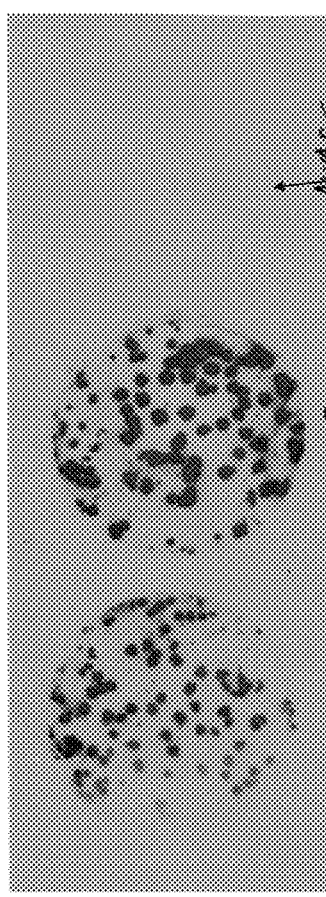
FIG. 16 illustrates the results of an immunoplaque assay of vCP2241.4.1.1.1, indicating that the homogeneity of the population was 100%.

In addition, an immunoplaque assay of stock using HA-specific chicken polyclonal antiserum TK/W1/68 reveled that the homogeneity of the vFP2211 population was 100% (see FIG. 6)

Figure 2:
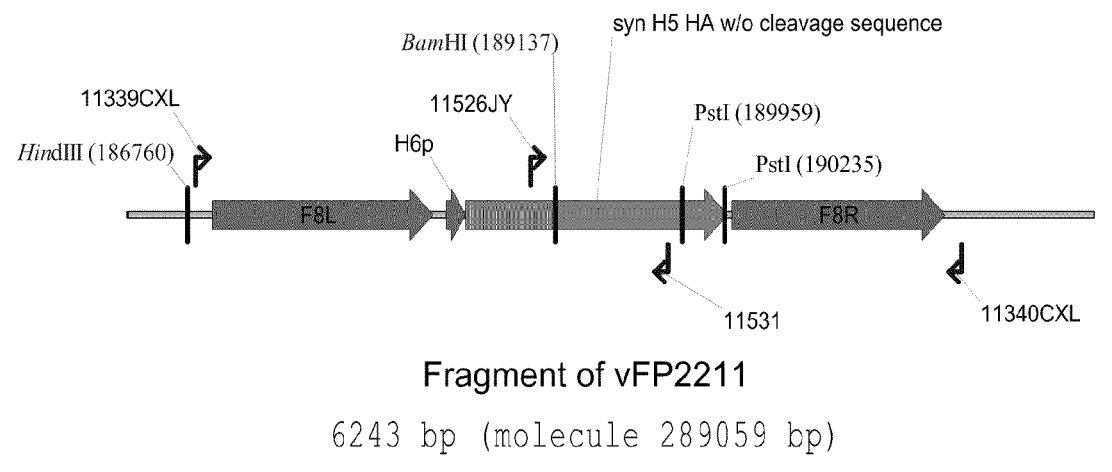

Furthermore, a more detailed analysis of the P2 stock genomic DNA was performed by PCR amplification and sequence analysis of the flanking arms of the F8 locus and the H6p AIV synthetic H5 HA cleavage mutant insert. Primers 11339 (SEQ ID NO: 12) and 11340 (SEQ ID NO: 13), located beyond the arms of the F8 locus in the donor plasmid, were used to amplify the entire F8L-insert-F8R fragment (SEQ ID NO: 14; see FIG. 2). The results showed that the sequences of the H6p AIV synthetic H5 HA cleavage mutant insert and the F8 left and right arms in vFP2211 were correct.

Example 3

Construction and Development of ALVAC AIV H5 (vCP2241)

AIV H5 HA Gene

The nucleotide sequence used in the construction of vFP2241 was derived from AIV A/Chicken/Indonesia/03H5 HA gene supplied by GeneArt GmbH (Regensburg, Germany). The sequence is contained in plasmid pCR-Script/HA-CK/Indonesia/03-(modified)-avipox and is synthetic with codon optimization for expression in avian cells and with a modification of HA cleavage site (SEQ ID NO: 15, SEQ ID NO: 16). Comparison between the synthetic H5 HA without cleavage site (from plasmid pCR-Script/HA-CK/Indonesia/03-(modified)-avipox) and wild type H5 HA without cleavage site (Ck/Indonesia/2003) indicate that the nucleotide and amino acid sequences were very similar (see FIGS. 7, 8)

Plasmid Construction of pLH1852.5

To construct the ALVAC plasmid pALVAC $C_5H_6$p-AIV synthetic H5 HA without cleavage site (pLH1852.5), the plasmid pJY1394.1 (see Example 2) was digested using EcoRV/SpeI digestion in order to isolate the expression cassette comprised of the H6 promoter and synthetic AIV H5 HA gene. This fragment was then ligated to Eco DNA digested pALVAC $C_5H_6$p donor (pCXL148.2) (see FIG. 9). The resulting plasmid pLH1852.5 (FIG. 10) was confirmed to contain the correct nucleotide (SEQ ID NO: 18) and amino amino acid (SEQ ID NO: 17) sequences.

Generation of ALVAC AIV H5 Recombinants vCP2241

To generate vCP2241, plasmid pLH1852.5, which contained the synthetic A/Chicken/Indonesia/03H5 HA gene, was linearized with NotI restriction enzyme. The linearized fragments were individually transfected into ALVAC-infected primary CEF cells by using the calcium phosphate precipitation method described previously (Panicali et al. 1982; Piccini et al. 1987) (FIG. 11). After 24 h, the transfected-infected cells were harvested, sonicated and used for recombinant virus screening.

Recombinant plaques were screened based on the plaque lift hybridization method using an AIV synthetic H5-specific probe which was labeled with horse radish peroxidase according to the manufacturer's protocol (Amersham Cat# RPN-3001). After four sequential rounds of plaque purification, the recombinants, designated as vCP2241 was generated and confirmed by hybridization as 100% positive for the AIV synthetic H5 insert and 100% negative for the C5 ORF.

A single plaque was selected from the final round of plaque purification and expanded to obtain stocks to amplify vCP2241. The recombinant was re-confirmed by hybridization and was again found to be 100% positive for the AIV synthetic H5 insert and 100% negative for the C5 ORF. The infected cell culture fluid from the roller bottles was harvested and concentrated to produce virus stock.

Analysis of Recombinant vCP2241

To re-determine genetic purity, vCP2241 was re-confirmed by hybridization as 100% positive for the AIV probe and 100% negative for the C5 ORF.

A theoretical restriction enzyme gel for the genomic DNA was created in Vector NTI and is shown in FIG. 12. Genomic DNA was extracted from vCP2241 and digested with BamHI, HindIII and PstI, and separated by 0.8% agarose gel electrophoresis. The results revealed the correct insertion of the foreign gene sequence (see FIG. 13).

The genomic DNA digested with BamHI, HindIII and PstI was transferred to nylon membrane and Southern blot analysis was performed by probing with AIV synthetic H5 probe. Bands were observed at the expected sizes, indicating the correct insertion of AIV synthetic H5 into the C5 locus (FIG. 14)

Expression of the recombinant was examined through Western Blot Analysis. Primary CEF cells were infected vCP2241 at MOI of 10 and incubated at 37° C. for 24 hours. The cells and culture supernatant were then harvested. Sample proteins were separated on a 10% SDS -PAGE gel, transferred to Immobilon nylon membrane, and probed with HA specific chicken polyclonal antiserum (TK/WI/68) at 1:2000. Peroxidase conjugated donkey anti-chicken antiserum was used as a secondary antibody and the bands were visualized using Amersham detection reagents. One protein band was detected in the cell pellets of vCP2241 and vFP2211, indicating the expression of the hemagglutinin protein. The expressed protein did not secrete into the cell culture (FIG. 15)

The homogeneity of the vCP2241 population was 100% as evidenced by an immunoplaque assay, using HA-specific chicken polyclonal antiserum TK/WI/68 (FIG. 16).

A more detailed analysis of the P3 stock genomic DNA was performed by PCR amplification and sequence analysis of the flanking arms of the C5 locus and the AIV synthetic H5 insert. Primers 7931.DC (SEQ ID NO. 20).and 7932.DC (SEQ ID NO: 21) located beyond the arms of the C5 locus (SEQ ID NO. 22, FIG. 17), were used to amplify the entire C5R— AIV synthetic H5 insert-C5L fragment. The results showed that the sequence of the AIV synthetic H5 insert and the C5 left and right arms around the AIV synthetic H5 insert in vCP2241 was correct.

Example 4

Vaccination of Cats with vFP89 (TROVAC AIV-H5)

A study was conducted in which 20 cats, aged 16-18 weeks-old, were randomly divided into 2 groups. The first group was immunized with an attenuated fowlpox (TROVAC) expressing H5 genes from the avian influenza strain A/Turkey/Ireland/1378/83 (vFP89), while the second groups served as a control. On day 0 and day 29, the vaccinated cats were subcutaneosly administered 6.8 log10 of 50% cell culture infective dose, per dose (CCID50/dose).

Blood samples were collected from all cats 3 days prior to the first vaccination, and on days 7, 14, 21, 29, 35, and 42 after the first vaccination. A hemagglutination inhibition (HI) test was performed as described previously (Swayne et al., 1997). Briefly, chicken red blood cell-(cRBC)-treated cat serum was serially diluted and then incubated in wells with 4 HA units of homologous (H5N8 AIV A/Turkey/Ireland/1378/83) and heterologous (H5N1 AIV A/Chicken/Indonesia/03) H5 AIV antigens. A 0.5% (vol/vol) suspension of cRBCs were allotted per well. Antibodies titers corresponding to the reciprocal of the highest dilution that inhibited hemagglutination were presented as geometric mean titers (GMTs).

Vaccination did not induce systemic or local adverse reactions. Antibodies to homologous AIV antigen were first detected in 8 of 10 cats at 1 week, and all cats thereafter. The GMTs at days 14, 21, and 29 were 91, 97, and 79, respectively. After the second dose on day 29, the GMTs on day 35 and 42 were 446.

Antibodies to heterologous AIV antigen were detectable after the second vaccination on days 35 and 42, in which the GMTs were 34 and 39, respectively.

Together, these results indicate that the vaccines induced high levels of antibodies to H5 avian influenza virus.

Example 5

Vaccination of Cats with vFP89 (TROVAC AIV-H5) vFP2211 (TROVAC AIV H5) and vCP2241 (ALVAC AIV H5)

A study was conducted in which 24 cats, aged 16-18 weeks old, were randomly divided into 4 groups. Three groups were immunized with either an attenuated fowlpox (TROVAC) expressing H5 gene from the avian influenza strain A/Turkey/Ireland/1378/83 (vFP89), an attenuated fowlpox (TROVAC) expressing H5 gene from the avian influenza strain A/Chicken/Indonesia/03 (vFP2211), or an attenuated canarypox (ALVAC) expressing H5 gene from the avian influenza strain A/Chicken/Indonesia/03 (vCP2241). The fourth group was unvaccinated and served as a control. On day 0 and day 21, the vaccinated cats received subcutaneous injections in the interscapula area of approximately 7.2 log10 of 50% cell culture infective dose, per dose (CCID50/dose).

The vaccines were tirated, as shown in Table 2.

| Group | Vectors | Injection titer at D0 (log10 $CCID_{50}$/dose) | Injection titer at D21 (log10 $CCID_{50}$/dose) |
| --- | --- | --- | --- |
| vFP89 | TROVAC AIV H5 vector A/Turkey/Ireland/1378/83 | 7.0 | 6.7 |
| vFP2211 | TROVAC AIV H5 vector A/chicken/Indonesia/03 | 7.4 | 7.1 |
| vCP2241 | ALVAC AIV H5 vector A/chicken/Indonesia/03 | 6.4 | 6.7 |

Blood samples were collected on days 0, 15, 21, and 35 for all groups, and additionally on day 84 for the vaccinated groups. A hemagglutination inhibition (HI) test was performed as described in Example 4. For this study, the homologous AIV antigen was H5N8 AIV A/Turkey/Ireland/1378/83, and the heterologous antigen was H5N1 AIV A/Vietnam/1194/04 (NIBRG14 strain). A 0.5% (vol/vol) suspension of cRBCs were allotted per well. The results are presented as log 10 of the highest dilution of cat serum that inhibited hemaggluntination.

Figure 18:
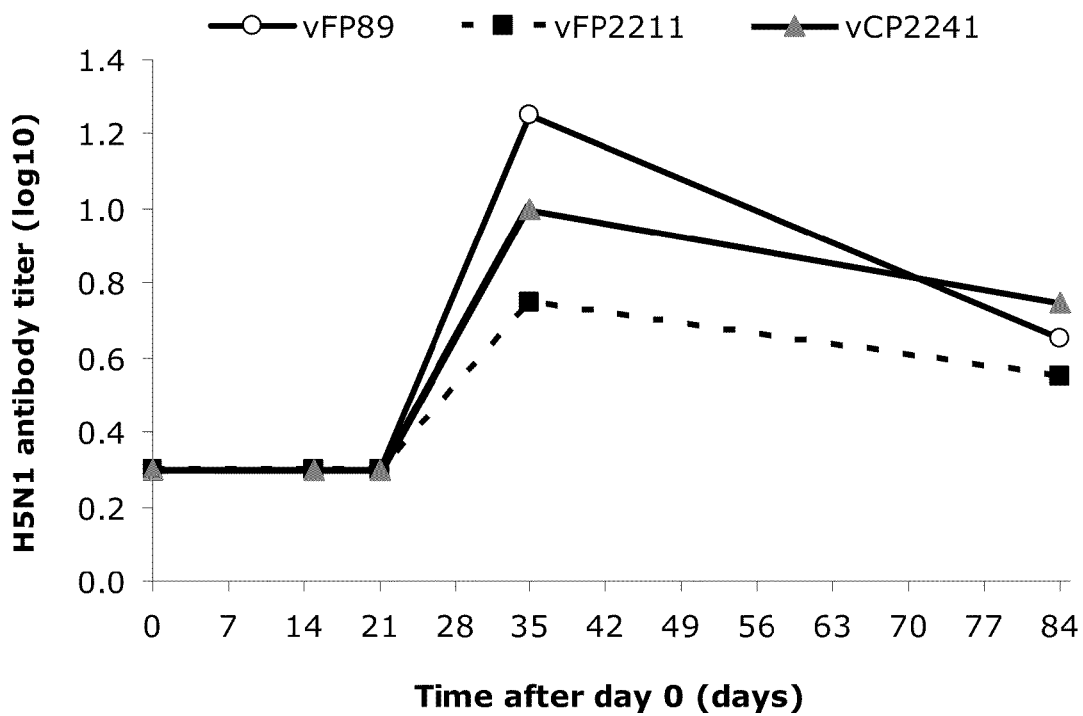
FIG. 18 illustrates the HI antibody responses to H5N1 AIV (A/Vietnam/1194/04 antigens in cats vaccinated with either TROVAC fowlpox virus expressing the H5 gene from A/Turkey/Ireland/1378/83 (vFP89), TROVAC fowlpox virus expressing the H5 gene from A/Chicken/Indonesia/03 (vFP2211), or ALVAC canarypox virus expressing the H5 gene from A/Chicken/Indonesia/03 (vCP2241).
Figure 19:
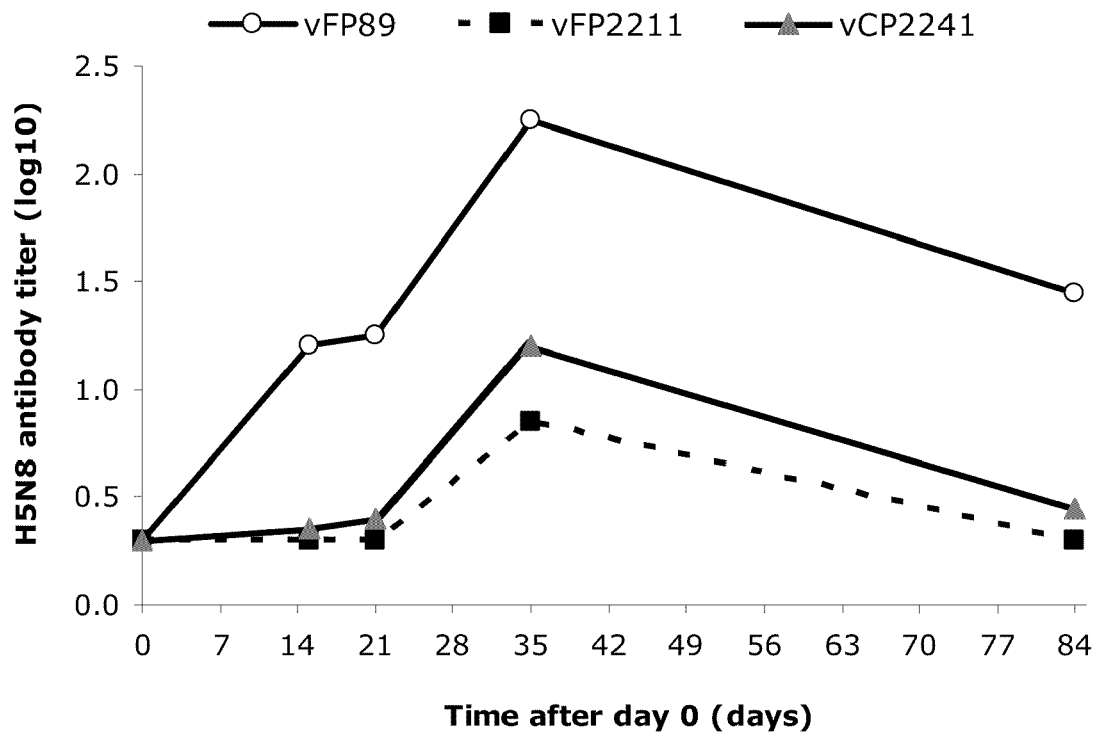

Injection with the recombinant vaccines induced high levels of antibodies to H5 avian influenza virus. Among the vaccined groups, cats injected with the vFP89 plasmid displayed higher HI responses against both the homologous and heterologus antigens (see FIGS. 18 and 19). In addition, vCP2241 showed greater HI responses than vFP2211 against both types of antigens. Nonetheless, all three vaccines induced an immunogenic response in cats.

Example 6

Vaccination of Cats with Inactivated AIV

A study was conducted in which two groups of 20 week-old cats received vaccines comprising inactivated AIV. The viruses (H5N9 AIV A/Chicken/Italy/22A/98) were inactivated by 0.1% beta-propiolactone at 5° C. for 18 hours, and were then harvested and filtated through a 10 µm cutoff filter. The vaccine was adjuvanted with oil-in-water emulsion.

All cats experienced subcutaneous injections in the interscapula area of a 1 ml dose on days 0 and 21. The first group (n=5) received approximately 512 HA units (UHA) of inactivated vaccine, while the second group (n=5) received approximately 1536 UHA of inactivated vaccine.

Blood samples were collected on days 0, 14, 21, and 35 for all animals. A hemagglutination inhibition (HI) test was performed as described in Example 4. For this study, the homologous AIV antigen was H5N9 AIV A/Turkey/Wisconsin/68, and the heterologous antigen was H5N1 AIV A/Vietnam/1194/04 (NIBRG14 strain). A 0.5% (vol/vol) suspension of cRBCs were allotted per well. The results are presented as log 10 of the highest dilution of cat serum that inhibited hemaggluntination.

Figure 20:
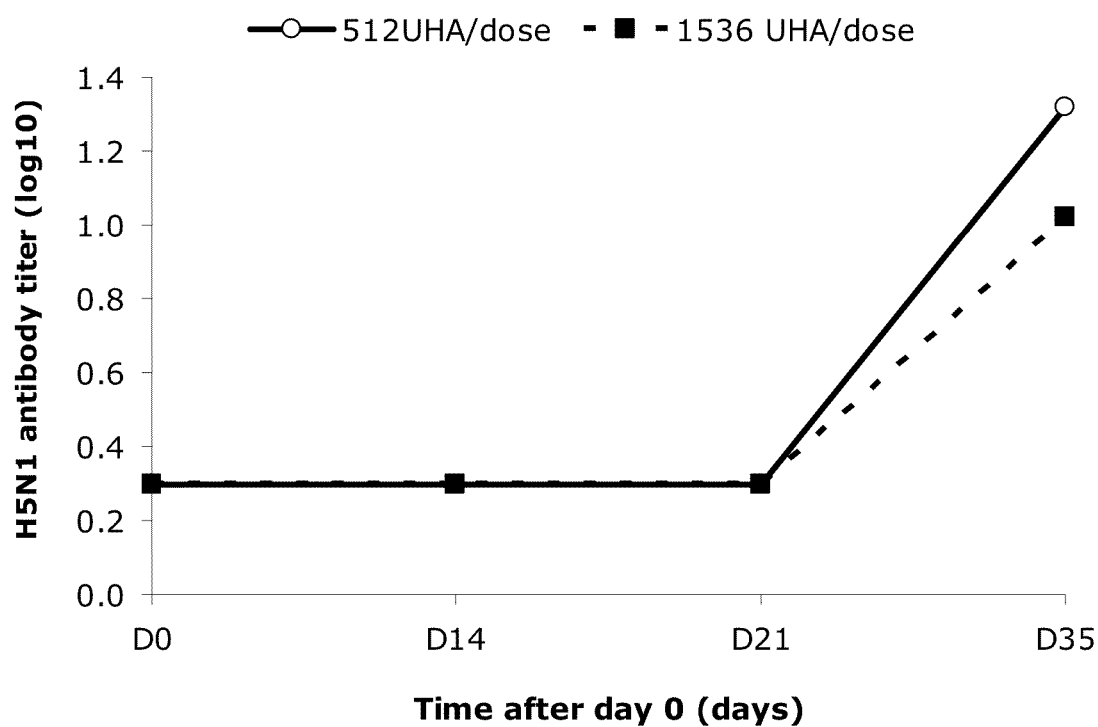
FIG. 20 illustrates the HI antibody responses to H5N1 AIV (A/Vietnam/1194/04, NIBRG14 strain antigens in cats vaccinated with an inactivated H5N9 AIV (A/Chicken/Italy/22A/98) at dosages of 512UHA/dose and 1536UHA/dose)
Figure 21:
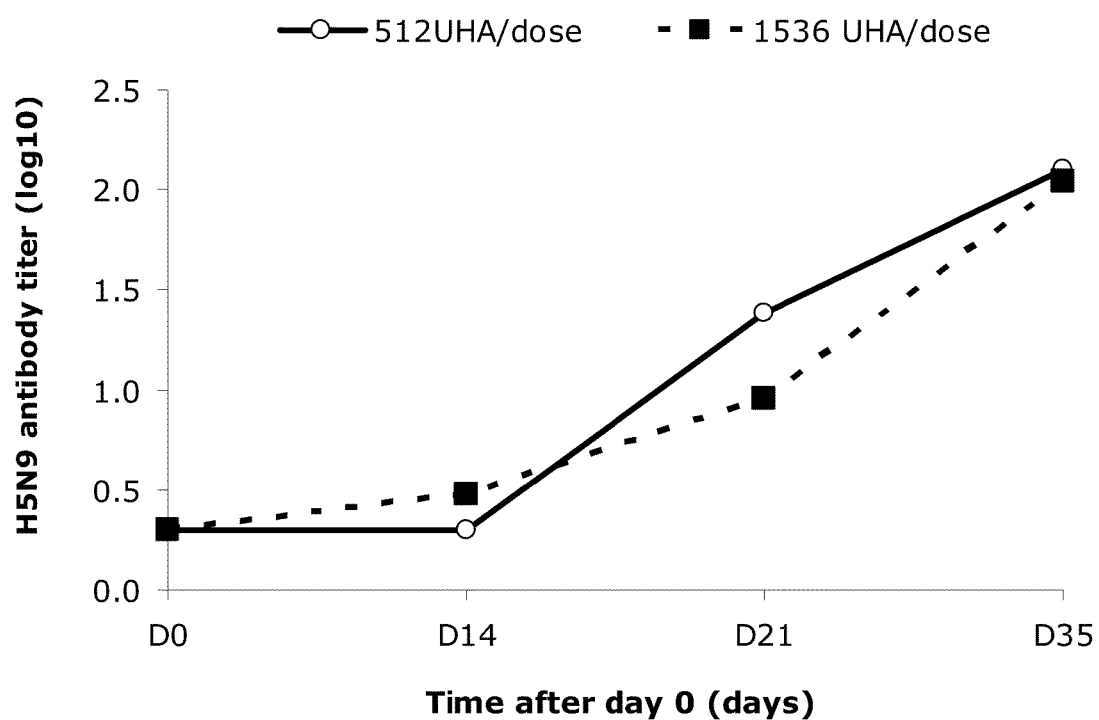
FIG. 21 illustrates the HI antibody responses to H5N9 AIV (A/Turkey/Wisconsin/68) antigens in cats vaccinated with an inactivated H5N9 AIV (A/Chicken/Italy/22A/98) at dosages of 512UHA/dose and 1536UHA/dose)

The results indicate that cats injected with the inactivated vaccine induced high levels of antibodies to H5 avian influenza. While cats injected with 512 UHA/dose displayed higher HI responses against both homologous (see FIG. 20) and heterologous (see FIG. 21) antigens than cats injected with 1536 UHA/dose, both dosages induced an immunogenic response.

The invention is further described by the following numbered paragraphs:

1. A method of eliciting an immune response against influenza in a Felidae, comprising administering a formulation, wherein said formulation comprises an avipox expression vector comprising a polynucleotide encoding an influenza antigen, epitope or immunogen in an effective amount for eliciting an immune response.

2. A method of inducing a protective immune response against influenza in a Felidae, comprising administering a formulation, wherein said formulation comprises an avipox expression vector, wherein said avipox expression vector comprises a polynucleotide encoding an influenza antigen, epitope or immunogen in an effective amount for inducing a protective immune response.

3. The method of paragraph 1 or 2, wherein the formulation further comprises one or more of a pharmaceutically or veterinarily acceptable carrier, excipient, vehicle or adjuvant.

4. The method of any one of paragraphs 1 to 3, wherein the influenza antigen, epitope or immunogen is a hemagglutinin, matrix protein, membrane protein, neuraminidase, nonstructural protein, nucleoprotein, polymerase or any fragment thereof.

5. The method of any one of paragraphs 1 to 4, wherein the influenza antigen, epitope or immunogen is isolated from a feline infected with influenza.

6. The method of paragraph 5 wherein the influenza antigen, epitope or immunogen is isolated from the broncho alveolar lavage and/or lung tissues of the feline.

7. The method of any one of paragraphs 1 to 4, wherein the influenza antigen, epitope or immunogen is isolated from an avian influenza.

8. The method of any one of paragraphs 1 to 7, wherein the avipox expression vector is an attenuated avipox expression vector.

9. The method of paragraph 8, wherein the avipox expression vector is a fowlpox vector.

10. The method of paragraph 9, wherein the fowlpox vector is a TROVAC vector.

11. The method of paragraph 8, wherein the avipox expression vector is a canarypox vector.

12. The method of paragraph 11, wherein the canarypox vector is ALVAC.

13. The method of paragraph 9, 10, 11, or 12, wherein the influenza antigen, epitope or immunogen is a hemagglutinin.

14. The method of paragraph 13, wherein the hemagglutinin is H5.

15. The method of paragraph 13 or 14, wherein the fowlpox vector is FP89 or FP2211.

16. The method of paragraph 13 or 14, wherein the canarypox vector is CP2241.

17. A method of eliciting an immune response against influenza in a Felidae, comprising administering a formulation, wherein said formulation comprises an inactivated influenza vaccine in an effective amount for eliciting an immune response.

18. A method of inducing a protective immune response against influenza in a Felidae, comprising administering a formulation, wherein said formulation comprises an inactivated influenza vaccine in an effective amount for inducing an immune response.

19. The method of paragraph 17 or 18, wherein the formulation further comprises one or more of a pharmaceutically or veterinarily acceptable carrier, excipient, vehicle or adjuvant.

20. The method of any one of paragraph 17 to 19, wherein the inactivated influenza vaccine is an inactivated feline influenza.

21. The method of any one of paragraphs 17 to 19, wherein the inactivated influenza vaccine is an inactivated avian influenza.

22. The method of any one of claims 1-21, further comprising additionally administering, either prior or subsequent to said formulation, a second formulation comprising either an avipox expression vector, wherein said vector comprises a polynucleotide encoding an influenza antigen, or an inactivated influenza immunological composition.

23. An immunological composition comprising a formulation, wherein said formulation comprises an avipox expression vector comprising a polynucleotide encoding an influenza antigen, epitope or immunogen, and a pharmaceutically or veterinarily acceptable carrier, excipient or vehicle in an effective amount for inducing an immune response.

24. The immunological composition of paragraph 23, wherein the formulation further comprises an adjuvant.

25. The immunological composition of paragraph 23 or 24, wherein the influenza antigen, epitope or immunogen is a hemagglutinin, matrix protein, membrane protein, neuraminidase, nonstructural protein, nucleoprotein, polymerase or any fragment thereof.

26. The immunological composition of any one of paragraphs 23 to 25, wherein the influenza antigen, epitope or immunogen is isolated from a feline infected with influenza.

27. The immunological composition of paragraph 26 wherein the influenza antigen, epitope or immunogen is isolated from the broncho alveolar lavage and/or lung tissues of the feline.

28. The immunological composition of any one of paragraphs 23 to 25, wherein the influenza antigen, epitope or immunogen is isolated from an avian influenza.

29. The immunological composition of any one of paragraphs 23 to 28, wherein the avipox expression vector is an attenuated avipox expression vector.

30. The immunological composition of paragraph 29, wherein the avipox expression vector is a fowlpox vector.

31. The immunological composition of paragraph 30, wherein the fowlpox vector is a TROVAC vector.

32. The immunological composition of paragraph 29, wherein the avipox expression vector is a canarypox vector.

33. The immunological composition of paragraph 32, wherein the canarypox vector is ALVAC.

34. The immunological composition of any one of paragraphs 30-33, wherein the influenza antigen, epitope or immunogen is a hemagglutinin.

35. The immunological composition of paragraph 34, wherein the hemagglutinin is H5.

36. The immunological composition of paragraph 34 or 35, wherein the fowlpox vector is vFP89 or vFP2211.

37. The immunological composition of paragraph 34 or 35, wherein the canarypox vector is vCP2241.

37. A kit for performing any one of the methods of paragraphs 1 to 21 comprising the immunological composition of any one of paragraphs 22 to 36 and instructions for performing the method of any one of paragraphs 1 to 36.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

REFERENCES

1. Abed et al. J Infect Dis. 186: 1074-1080, 2002
2. Air et al. Virology. 160: 346-54, 1987
3. Alexander et al. Res Vet Sci. 26: 17-20, 1979
4. Altschul et al. J Mol. Biol. 215: 403-410, 1990
5. Altschul et al. Local alignment statistics. Methods Enzymol. 266: 460-480, 1996
6. Amonsin et al. Virology. 344: 480-491, 2006
7. Andreansky et al. Proc Natl Acad Sci USA. 93: 11313-11318, 1996
8. Antoine. Virology 244: 365-396, 1998
9. Anwar et al. In Silico Biology 6: 0015, 2006
10. Appleton et al. Vet Immunol Immunopathol 23: 257-266, 1989
11. Audsley et al. Expert Opin Biol Ther. 4: 709-717, 2004
12. Audsley et al. J Virol Methods. 123: 187-193, 2005
13. Austin et al. J Gen Virol. 71: 2471-2474, 1990
14. Ayora-Talayera et al. Emerg Infect Dis. 11: 158-161, 2005
15. Babiuk et al. Vaccine. 20: 3399-3408, 2002
16. Baez et al. Virology. 113: 397-402, 1981
17. Ballay et al. EMBO J. 4:3861-3865, 1994
18. Banks et al. Avian Pathol. 29: 353-360, 2000
19. Bantia et al. Antimicrob Agents Chemother. 42: 801-807, 1998
20. Bean et al. J. Virol. 54: 151-160, 1985
21. Behr. Bioconjug Chem. 5: 382-389, 1994
22. Bergmann et al. Eur J. Immunol. 23: 2777-2781, 1993
23. Bergmann et al. J. Immunol. 157: 3242-3249; 1996
24. Berkner et al. Nucl Acid Res. 11: 6003-6020, 1983
25. Berkner. Bio Techniques. 6: 616-629, 1988
26. Blok et al. Biochemistry 21: 4001-4007, 1982
27. Boshart et al. Cell. 41: 521-530, 1985
28. Brands et al. Dev Biol Stand. 98: 93-100, 1999
29. Breathnach et al. Vet Immunol Immunopathol. 98: 127-136, 2004
30. Brown et al. Clin Microbiol. 26: 313-318, 1988
31. Brown et al. Mol Immunol. 19: 329-338, 1982
32. Brown et al. Vet Rec. 132: 598-602, 1993
33. Budowsky et al. Vaccine. 11: 343-348, 1993
34. Budowsky et al. Vaccine. 9: 398-402, 1991
35. Butler. Nature. 440: 135, 2006
36. Capua et al. Avian Pathol. 28: 455-460, 1999
37. Carroll et al. Vaccine 15: 387-394, 1997
38. Carter et al. Arch Virol. 71: 13-25, 1982

39. Cauthen et al. J Virol. 74: 6592-6599, 2000
40. Chambers et al. Equine Vet J. 33: 630-636, 2001
41. Chare et al. J Gen Virol. 84: 2691-2703, 2003
42. Chavier et al J Virol. 70: 4805-4810, 1996
43. Chen et al. Avian Dis. 47: 1127-1130, 2003
44. Cheung et al. Lancet. 360: 1831-1837, 2002
45. Chin et al. J. Virol. 76: 507-516, 2002
46. Chroboczek et al. Virol 186: 280-285, 1992
47. Claas et al. Lancet. 351: 472-477, 1998
48. Clavijo et al. Can J Vet Res. 66: 117-121, 2002
49. Cochran et al. J Virol. 54: 30-35, 1985
50. Crouch et al. Vaccine. 23: 418-425, 2004
51. Danthinne et al. Gene Therapy. 7: 1707-1714, 2000
52. De et al. Nucleic Acids Res. 16: 4181-4182, 1988
53. De Groot et al. Nat Biotechnol. 17: 533-561, 1990
54. de Jong et al. J Clin Virol. 35: 2-13, 2006
55. Donofrio et al. J Vet Diagn Invest. 6: 39-43, 1994
56. Duhaut et al. Virology. 248: 241-253, 1998
57. Duhaut et al. Virology. 275: 278-285, 2000
58. Egorov et al. J Virol. 72: 6437-6441, 1998
59. Elleman et al. Nucleic Acids Res. 10: 7005-7015, 1982
60. EP 0370573
61. EP 265785
62. EP-A-260148
63. EP-A-323597
64. Falloux et al. Hum Gene Ther. 9: 1909-1917, 1998
65. Felgner et al. J Biol Chem. 269:2550-2561, 1994
66. Fields et al. Nature. 186: 778-780, 1960
67. Fischer et al. Vaccine. 20: 3485-3497, 2002
68. Foni et al. New Microbiol. 28: 31-35, 2005
69. Fouchier et al. J Virol. 79: 2814-2822, 2005
70. Frolov et al. Proc Natl Acad Sci USA. 93: 11371-11377, 1996
71. Funahashi et al. J Gen Virol. 69: 35-47, 1988
72. Gambaryan et al. Virus Res. 114: 15-22, 2005
73. Gao et al. J Virol. 80: 1959-1964, 2006
74. Garcia et al. Avian Dis. 42: 248-256, 1998
75. Gardner et al. 12th World AIDS Conference, Geneva, Switzerland, 1998.
76. Gething et al. Nature 287: 301-306, 1980
77. Geysen et al. Molec Immunol. 23: 709-715, 1986
78. Geysen et al. Proc Natl Acad Sci USA. 81: 3998-4002, 1984
79. Geysen et al. Proc Natl Acad Sci USA. 82: 178-182, 1985
80. Geysen. Southeast Asian J Trop Med Public Health 21: 523-533, 1990
81. Ghendon et al. Vaccine. 23: 4678-4684, 2005
82. Gibson et al. Virus Res. 22: 93-106, 1992
83. Gish et al. Nat Genet. 3: 266-272, 1993
84. Goto et al. J Vet Med Sci. 55: 33-37, 1993
85. Govorkova et al. J Virol. 70: 5519-5524, 1996
86. Govorkova et al. J. Infect. Dis. 172: 250-253, 1995
87. Graham et al. Gene Transfer and Expression Protocols. Methods in Mol. Biol. The Human Press Inc. 7: 109-128, 1991
88. Graham et al. J Gen Virol 36: 59-72, 1977
89. Graham. Tibtech 8: 85-87; 1990
90. Gross et al. Equine Vet J. 30: 489-497, 1998
91. Grunhaus et al. Sem Virol. 3: 237-252, 1992
92. Guan et al. J Virol. 74: 9372-9380, 2000
93. Guan et al. Proc Natl Acad Sci USA. 10: 8156-8161, 2004
94. Gubareva et al. J Gen Virol. 83: 2683-2692, 2002
95. Gubareva et al. J Infect Dis. 183: 523-531, 2001
96. Gubareva et al. J Virol. 71: 3385-3390, 1997
97. Gujuluva et al. Virology. 204: 491-505, 1994
98. Guo et al. J Virol 63: 4189-4198, 1989
99. Halperin et al. Vaccine. 16: 1331-1335, 1998
100. Halperin et al. Vaccine. 20: 1240-1247, 2002
101. Hannant et al. Vet Immunol Immunopathol. 21: 327-337, 1989
102. Hannant et al. Vet Microbiol. 19: 293-303, 1989
103. Hannant et al. VetRec. 122: 125-128, 1988
104. Hardy et al. Virus Res. 77: 89-96, 2001
105. Harley et al. Arch Virol. 113: 267-277, 1990
106. Hartikka et al. Hum Gene Ther. 7: 1205-1217, 1996
107. Hatta et al. Virology 295: 250-55, 2002
108. Hauptmann et al. J Gen Virol. 64: 215-20, 1983
109. Hayden et al. Antiviral Res. 25: 123-131, 1994
110. Heldens et al. J Immunol Methods. 264: 11-17, 2002
111. Heldens et al. Vet J. 167: 150-157, 2004
112. Hemmer et al. Immunol Today, 19: 163-168, 1998
113. Hinshaw et al. Infect Immun. 24: 354-361, 1981
114. Hoffmann et al. Proc Natl Acad Sci USA. 99: 11411-11416, 2002
115. Horimoto et al. Clin Microbiol Rev. 14: 129-149, 2001
116. Horner et al. Ledgard, N Z Vet J. 36: 205-206, 1988
117. Horner et al. N Z Vet J. 36:205-206, 1988
118. Howard et al. Avian Dis. 2006
119. Iammikova et al. Vopr Virusol. 34: 568-572, 1989
120. Iftimovici et al. Virologie. 31: 243, 1980
121. Ilan et al. Proc Natl Acad Sci USA. 94: 2587-2592, 1997
122. Ilobi et al. Arch. Virol. 143: 891-901, 1998
123. Influenza team. Euro Surveill. 11: E060413.4, 2006
124. Iuferov et al. Dokl Akad Nauk SSSR. 278: 738-742, 1984
125. Johansson et al. Vaccine. 16: 1009-1015, 1998
126. Ju et al. Diabetologia 41: 736-739, 1998
127. Kanegae et al. Arch Virol. 134: 17-28, 1994
128. Karaca et al. Clin Diagn Lab Immunol. 12: 1340-1342, 2005
129. Karasin et al. J Clin Microbiol. 38: 2453-2456, 2000
130. Karasin et al. J Clin. Microbiol. 40: 1073-1079, 2002
131. Karasin et al. J Clinical Microbiol. 44: 1123-1126, 2006
132. Karlin et al. Proc Natl Acad Sci USA. 87: 2264-2268, 1990
133. Karlin et al. Proc Natl Acad Sci. USA 90: 5873-5877, 1993
134. Kawaoka et al. Virology 179: 759-767, 1990
135. Keawcharoen et al. Emerg Infect Dis. 10: 2189-91, 2004
136. Keverin et al. Arch Virol. 145: 1059-1066, 2000
137. Kistner et al. Vaccine. 16: 960-968, 1998
138. Kitson et al. J Virol. 65: 3068-3075, 1991
139. Klinman et al. Proc Natl Acad Sci USA. 93: 2879-2883, 1996
140. Kuiken et al. Nature. 440: 741-742, 2006,
141. Kuiken et al. Science. 306: 241-242, 2006
142. Kwissa et al. Vaccine. 18: 2337-2344, 2000
143. Landolt et al. Am J Vet Res. 66: 119-124, 2005
144. Lee et al. J Virol. 79: 11412-11421, 2005
145. Leneva et al. Antimicrob Agents Chemother. 45: 1216-1224, 2001
146. Li et al. Nat Biotechnol. 17: 241-245, 1999
147. Lin et al. Virology. 287: 202-213, 2001
148. Lindstrom et al. Arch Virol. 143: 1585-1598, 1998
149. Liu et al. Virology 305: 267-275, 2003
150. Lu et al. Arch Virol. 147: 273-284, 2002
151. Luke et al. J Infect Dis. 175: 91-97, 1997
152. Macklin et al. J Virol. 72: 1491-1496, 1998
153. Mantani et al. Planta Med. 67: 240-243, 2001
154. Markoff et al. Virology. 119: 288-297, 1982
155. Marozin et al. J. Gen. Virol. 83:735-745, 2002
156. Mazanec et al. J Virol. 69: 1339-1343, 1995
157. McClements et al. Proc Natl Acad Sci USA. 93: 11414-11420, 1996

158. Merten et al Adv Exp Med Biol. 397: 141-151, 1996
159. Miyamoto et al. Antiviral Res. 39: 89-100, 1998
160. Miyazaki et al. Gene. 79: 269-277, 1989
161. Mohler et al. Biotechnol Bioeng. 90: 46-58, 2005
162. Morley et al. Vet Microbiol. 45: 81-92, 1995
163. Morris GE, ed. Epitope Mapping Protocols in Methods in Mol. Bio. Humana Press Inc. 66, 1996
164. Moss. Proc Natl Acad Sci USA. 93: 11341-11348, 1996
165. Mumford et al. Epidemiol Infect. 100: 501-510, 1988
166. Mumford et al. J Hyg (Lond). 9: 385-395, 1983
167. Mumford et al. Vet Rec. 134:158-162, 1994
168. Naeve et al. EMBO J. 9: 3857-3866, 1990
169. Nagai et al. Antiviral Res. 26: 11-25, 1995
170. Nagai et al. Biol Pharm Bull. 18: 295-299, 1995
171. Nakagawa et al. J Virol Methods. 79: 113-120, 1999
172. Nayak et al. J Chromatogr B Analyt Technol Biomed Life Sci. 823: 75-81, 2005
173. Nelson et al. FASEB J. 15: 1846-1848, 2001
174. Nerome et al. Arch Virol. 86: 197-211, 1985
175. Nestorowicz et al. Virology 160: 411-418, 1987
176. Noble et al. J Gen Virol. 75: 3485-3491, 1994
177. Nunes-Correia et al. Biochemistry. 38: 1095-1101, 1999
178. Ohuchi et al. J Virol. 68: 920-926, 1994
179. Olsen et al. Arch Virol. 145: 1399-1419, 2000
180. Olsen et al. Science. 312: 384-388, 2006
181. Olsenetal. Vaccine. 15: 1149-1156, 1997
182. Orlich et al. Virology. 176: 531-538, 1990
183. Ottis et al. Arch Virol. 63: 185-190, 1980
184. Ozaki et al. Vet Microbiol. 82: 111-119, 2001
185. Palker et al. Virus Res. 105: 183-194, 2004
186. Panicali et al. Proc. Natl. Acad Sci USA. 79: 4927-4931, 1982
187. Panigrahy et al. Avian Dis. 40: 600-604, 1996
188. Paoletti. Proc Natl Acad Sci USA. 93: 11349-11353, 1996
189. PCT Application No. WO87/03905.
190. PCT Application No. WO89/01036
191. PCT Application No. WO95/14102
192. PCT Application No. WO98/00166
193. PCT Application No. WO99/01158
194. PCT Application Serial No. PCT/US2004/022605
195. Pearson et al. Proc Natl Acad Sci USA. 85: 2444-2448, 1988
196. Pennock et al. Mol Cell Biol. 4: 399-406, 1984
197. Perkins et al. Avian Dis. 46: 877-885, 2002
198. Perkins et al. Vet Pathol. 38: 149-164, 2001
199. Perkus et al. J Virol 63: 3829-3836, 1989
200. Pharmeuropa 8(2), 1996
201. Philpott et al. J Virol 63: 3453-3458, 1989
202. Piccini et al. Methods Enzymol. 153: 545-563, 1987
203. Powell. Vaccine Design, The Subunit and Adjuvant Approach. Plenum Press. 147, 1995
204. Pruett et al. Biochemistry. 37: 10660-10670, 1998
205. Puthavathana et al. J Gen Virol. 86: 423-433, 2005
206. Quinlivan et al. J Clin Microbiol. 42: 759-763, 2004
207. Richards et al. Vet Immunol Immunopathol. 33: 129-143, 1992
208. Richardson (Ed). Baculovirus Expression Protocols. Methods in Mol. Biol. 39, Humana Press Inc., 1995
209. Rimmelzwaan et al. Am J Pathol. 168: 176-183, 2006
210. Riviere et al. J Virol. 66: 3424-3434, 1992
211. Robertson et al. Proc Natl Acad Sci USA. 93: 11334-11340, 1996
212. Robinson et al. Sem Immunol. 9: 271-283, 1997
213. Rohm et al. Virology 218: 253-257, 1996
214. Rohm et al. Virology. 217: 508-516, 1996
215. Roizman. Proc Natl Acad Sci. USA. 93: 11307-11312, 1996
216. Ross et al. Archiv Für die gesamte Virusforschung. 30: 82-88, 1970
217. Rott et al. J Gen Virol. 44: 471-77, 1979
218. Saito et al. Virology. 193: 868-876, 1993
219. Sambrook et al. Molecular Cloning: A Laboratory Manual 2nd ed, 1989
220. Scholtissek et al. J Virol. 76: 1781-1786, 2002
221. Shida. Virology. 150: 451-457, 1986
222. Shimizu et al. Virology. 254: 213-219, 1999
223. Shinya et al. J Virol. 79: 9926-9932, 2005
224. Short et al. J Vet Pharmacol Ther. 9: 426-432, 1986
225. Shortridge et al. Virology 252: 331-342, 1998
226. Shriver et al. Nature. 415: 331-335, 2002
227. Sidwell et al. Antiviral Res. 37: 107-120, 1998
228. Slemons et al. Bull World Health Organ. 47: 521-525, 1972
229. Smirnov et al. Acta Virol. 44: 1-8, 2000
230. Smith et al. Mol Cell Biol. 3: 2156-2165, 1983
231. Staschke et al. Virology. 248: 264-274, 1998
232. Stenberg et al. J Virol. 49: 190-199, 1984
233. Stickl et al. Munch Med Wschr. 113: 1149-1153, 1971
234. Stittelaar et al. J Virol. 74: 4236-4243, 2000
235. Sugiura et al. J Virol Methods. 98: 1-8, 2001
236. Suhrbier. Immunol. Cell Biol. 75: 402-408; 1997
237. Sutter et al. Proc Natl Acad Sci USA. 89: 10847-10851, 1992
238. Sutter et al. Vaccine. 12: 1032-1040, 1994
239. Suzuki et al. Biochem J. 318: 389-393, 1996
240. Swayne et al. Avian Dis. 38: 151-157, 1994
241. Swayne et al. Avian Dis. 45: 355-365, 2001
242. Takeuchi et al. J Virol. 68: 911-919, 1994
243. Tapnell. Adv Drug Deliv Rev. 12: 185-199, 1993
244. Taylor et al. J Virol. 64, 1441-1450, 1990
245. Taylor et al. Vaccine. 6: 497-503, 1988a
246. Taylor et al. Vaccine. 6: 504-508, 1988b
247. Terregino et al. Vet Rec. 158: 491, 2006
248. Thomson et al. Vet Rec. 100: 465-468, 1977
249. Tollefsen et al. Scand. J. Immunol. 57: 229-238, 2003
250. Tollefsen et al. Vaccine. 20: 3370-3378, 2002
251. Tolstova et al. Acta Virol. 10: 315-321, 1966
252. Tomita et al. Kitasato Arch Exp Med. 44: 185-196, 1971
253. Tonew et al. Acta Virol. 26: 444-452, 1982
254. Toulemonde et al. Vet Rec. 156: 367-371, 2005
255. Treanor et al. J Virol. 68: 7684-7688, 1994
256. Tree et al. Vaccine. 19: 3444-3450, 2001
257. Tripathy et al. Proc Natl Acad Sci USA. 91: 11557-11561, 1994
258. Tumpey et al. J Virol. 76: 6344-6355, 2002
259. U.S. patent application Ser. No. 920,197
260. U.S. Pat. No. 2,909,462
261. U.S. Pat. No. 4,394,448
262. U.S. Pat. No. 4,603,112
263. U.S. Pat. No. 4,603,112
264. U.S. Pat. No. 4,708,871
265. U.S. Pat. No. 4,722,848
266. U.S. Pat. No. 4,722,848
267. U.S. Pat. No. 4,745,051
268. U.S. Pat. No. 4,769,330
269. U.S. Pat. No. 4,769,330
270. U.S. Pat. No. 4,769,331
271. U.S. Pat. No. 4,945,050
272. U.S. Pat. No. 4,968,615
273. U.S. Pat. No. 5,110,587
274. U.S. Pat. No. 5,122,458
275. U.S. Pat. No. 5,168,062

276. U.S. Pat. No. 5,174,993
277. U.S. Pat. No. 5,174,993
278. U.S. Pat. No. 5,338,683
279. U.S. Pat. No. 5,382,425
280. U.S. Pat. No. 5,385,839
281. U.S. Pat. No. 5,494,807
282. U.S. Pat. No. 5,494,807
283. U.S. Pat. No. 5,494,807
284. U.S. Pat. No. 5,494,807
285. U.S. Pat. No. 5,494,807
286. U.S. Pat. No. 5,505,941
287. U.S. Pat. No. 5,505,941
288. U.S. Pat. No. 5,505,941
289. U.S. Pat. No. 5,505,941
290. U.S. Pat. No. 5,514,375
291. U.S. Pat. No. 5,529,780
292. U.S. Pat. No. 5,552,143
293. U.S. Pat. No. 5,580,859
294. U.S. Pat. No. 5,589,466
295. U.S. Pat. No. 5,591,439
296. U.S. Pat. No. 5,591,639
297. U.S. Pat. No. 5,677,178
298. U.S. Pat. No. 5,688,920
299. U.S. Pat. No. 5,744,140
300. U.S. Pat. No. 5,744,141
301. U.S. Pat. No. 5,756,103
302. U.S. Pat. No. 5,756,103
303. U.S. Pat. No. 5,756,103
304. U.S. Pat. No. 5,756,103
305. U.S. Pat. No. 5,762,938
306. U.S. Pat. No. 5,762,938
307. U.S. Pat. No. 5,766,599
308. U.S. Pat. No. 5,766,599
309. U.S. Pat. No. 5,766,599
310. U.S. Pat. No. 5,846,946
311. U.S. Pat. No. 5,990,091
312. U.S. Pat. No. 6,004,777
313. U.S. Pat. No. 6,033,670
314. U.S. Pat. No. 6,045,803
315. U.S. Pat. No. 6,048,537
316. U.S. Pat. No. 6,048,537
317. U.S. Pat. No. 6,074,649
318. U.S. Pat. No. 6,090,393
319. U.S. Pat. No. 6,090,393
320. U.S. Pat. No. 6,103,526
321. U.S. Pat. No. 6,130,066
322. U.S. Pat. No. 6,130,066
323. U.S. Pat. No. 6,133,028
324. U.S. Pat. No. 6,153,199
325. U.S. Pat. No. 6,156,567
326. U.S. Pat. No. 6,156,567
327. U.S. Pat. No. 6,159,477
328. U.S. Pat. No. 6,159,477
329. U.S. Pat. No. 6,207,165
330. U.S. Pat. No. 6,207,166
331. U.S. Pat. No. 6,217,883
332. U.S. Pat. No. 6,221,362
333. U.S. Pat. No. 6,221,362
334. U.S. Pat. No. 6,224,882
335. U.S. Pat. No. 6,228,846
336. U.S. Pat. No. 6,306,400
337. U.S. Pat. No. 6,312,682
338. U.S. Pat. No. 6,348,196
339. U.S. Pat. No. 6,348,450
340. U.S. Pat. No. 6,368,603
341. U.S. Pat. No. 6,376,473
342. U.S. Pat. No. 6,376,473
343. U.S. Pat. No. 6,387,376
344. U.S. Pat. No. 6,391,314
345. U.S. Pat. No. 6,451,769
346. U.S. Pat. No. 6,451,770
347. U.S. Pat. No. 6,451,770
348. U.S. Pat. No. 6,464,984
349. U.S. Pat. No. 6,464,984
350. U.S. Pat. No. 6,485,729
351. U.S. Pat. No. 6,497,883
352. U.S. Pat. No. 6,558,674
353. U.S. Pat. No. 6,576,243
354. U.S. Pat. No. 6,586,412
355. U.S. Pat. No. 6,596,279
356. U.S. Pat. No. 6,692,956
357. U.S. Pat. No. 6,818,628
358. U.S. Pat. No. 6,852,705
359. U.S. Pat. No. 6,312,683
360. van der Goot et al. Avian Dis. 47: 939-941, 2002
361. Van der Zee et al. Eur J Immunol. 19: 43-47, 1989
362. van Maanen et al. Vet Microbiol. 93: 291-306, 2003
363. van Ooyen et al. Science. 206: 337-344, 1979
364. Viseshakul et al. Virology 328: 169-176, 2004
365. Walker et al. J Gen Virol. 74: 311-4, 1993
366. Walker et al. Virology. 190: 278-87, 1992
367. Wattrang et al. Viral Immunol. 16: 57-67, 2003
368. Webster Emerging Infectious Diseases 4, 1998
369. Webster et al. Vaccine. 11: 987-993, 1993
370. Wilbur et al. Proc Natl Acad Sci USA 80: 726-730, 1983
371. WO 00/03030
372. WO 01/05934
373. WO 90/01543
374. WO 91/11525
375. WO 94/16716
376. WO 96/34109
377. WO 96/39491
378. WO 98/16247
379. WO 98/33510
380. Wood et al. Arch. Virol. 130: 209-217, 1993
381. Xu, et al. Virology 261: 15-19, 1999
382. Yamane et al. Tohoku J Exp Med. 245-55, 1981
383. Yamnikova et al. Virology. 197: 558-563, 1993
384. Youil et al. J Virol Methods 120: 23-31, 2004
385. Youil et al. Virus Res. 102: 165-176, 2004
386. Youngner et al. Am J Vet Res. 62: 1290-1294, 2001
387. Yuen et al. Proc Natl Acad Sci USA. 84: 6417-6421, 1987
388. Zakay-Rones et al. J Altern Complement Med. 1: 361-369, 1995
389. Zakstel'skaia et al. Vopr Virusol. 551-557, 1977
390. Zambon. Rev Med Virol. 11: 227-241, 2001
391. Zhukova et al. Acta Virol. 19: 281-286, 1975

SEQ ID NO 1

LENGTH: 3659

TYPE: DNA

ORGANISM: Fowlpox virus

SEQUENCE:

```
   1 gatatctgtg gtctatatat actacaccct accgatatta accaacgagt ttctcacaag
  60 aaaacttgtt tagtagatag agattctttg attgtgttta aaagaagtac cagtaaaaag
 120 tgtggcatat gcatagaaga aataaacaaa aaacatattt ccgaacagta ttttggaatt
 180 ctcccaagtt gtaaacatat tttttgccta tcatgtataa gacgttgggc agatactacc
 240 agaaatacag atactgaaaa tacgtgtcct gaatgtagaa tagttttttcc tttcataata
 300 cccagtaggt attggataga taataaatat gataaaaaaa tattatataa tagatataag
 360 aaaatgattt ttacaaaaat acctataaga acaataaaaa tataattaca tttacggaaa
 420 atagctggtt ttagtttacc aacttagagt aattatcata ttgaatctat attgtttttt
 480 agttatataa aaacatgatt agcccccaat cggatgaaaa tataaaagat gttgagaatt
 540 tcgaatacaa caaaagagg aatcgtacgt tgtccatatc caaacatata aataaaaatt
 600 caaaagtagt attatactgg atgtttagag atcaacgtgt acaagataat tgggctttaa
 660 tttacgcaca acgattagcg ttaaaactca aaatacctct aagaatatgc ttttgtgtcg
 720 tgccaaaatt tcacactact acttctagac actttatgtt tttaatatcc ggtcttaaag
 780 aagtcgcgga agaatgtaaa agactatgta tagggttttc attgatatat ggcgtaccaa
 840 aagtaataat tccgtgtata gtaaaaaaat acagagtcgg agtaatcata acggatttct
 900 ttccattacg tgttcccgaa agattaatga aacagactgt aatatctctt ccagataaca
 960 taccttttat acaagtagac gctcataata tagtaccttg ttgggaagct tctgataaag
1020 aagaatacgg tgcacgaact ttaagaaaaa agatatttga taaattatat gaatatatga
1080 cagaatttcc tgttgttcgt aaacatccat acgtccatt ttctatatct attgcaaaac
1140 ccaaaaatat atcattagac aagacggtat tacccgtaaa atgggcaacg cctggaacaa
1200 aagctggaat aattgtttta aaagaattta taaaaaacag attaccgtca tacgacgcgg
1260 atcataacaa tcctacgtgt gacgctttga gtaacttatc tccgtggcta cattttggtc
1320 atgtatccgc acaacgtgtt gccttagaag tattaaaatg tatacgagaa agcaaaaaaa
1380 acgttgaaac gtttatagat gaaataattg taagaagaga actatcggat aattttttgtt
1440 actataacaa acattatgat agtatccagt ctactcattc atgggttaga aaaacattag
1500 aagatcacat taatgatcct agaaagtata tatattccat taaacaactc gaaaaagcgg
1560 aaactcatga tcctctatgg aacgcgtcac aaatgcagat ggtgagagaa ggaaaaatgc
1620 atagtttttt acgaatgtat tgggctaaga agatacttga atggactaga acacctgaag
1680 acgctttgag ttatagtatc tatttgaaca caagtacga actagacggc acggatccta
1740 acggatacgt aggttgtatg tggtctattt gcggattaca cgatagagcg tggaaagcaa
1800 gaccgatatt tggaaagata agatatatga attatgagag ttctaagaag aaatttgatg
1860 ttgctgtatt tatacagaaa tacaattaag ataaataata tacagcattg taaccatcgt
1920 catccgttat acggggaata atattaccat acagtattat taaattttct tacgaagaat
1980 atagatcggt atttatcgtt agtttatttt acatttatta attaaacatg tctactatta
2040 cctgttatgg aaatgacaaa tttagttata aatttatga taaaattaag ataataataa
2100 tgaaatcaaa taattatgta aatgctacta gattatgtga attacgagga agaaagttta
2160 cgaactggaa aaaattaagt gaatctaaaa tattagtcga taatgtaaaa aaaataaatg
```

```
2220  ataaaactaa ccagttaaaa acggatatga ttatatacgt taaggatatt gatcataaag 2280  gaagagatac ttgcggttac tatgtacacc aagatctggt atcttctata tcaaattgga 2340  tatctccgtt attcgccgtt aaggtaaata aaattattaa ctattatata tgtaatgaat 2400  atgatatacg acttagcgaa atggaatctg atatgacaga agtaatagat gtagttgata 2460  aattagtagg aggatacaat gatgaaatag cagaaataat atatttgttt aataaattta 2520  tagaaaaata tattgctaac atatcgttat caactgaatt atctagtata ttaaataatt 2580  ttataaattt tataaatttt aataaaaaat acaataacga cataaagata tttaatcttt 2640  aattcttgat ctgaaaaaca catctataaa actagataaa aagttattcg ataaagataa 2700  taatgaatcg aacgatgaaa aattggaaac agaagttgat aagctaattt ttttcatcta 2760  aatagtatta ttttattgaa gtacgaagtt ttacgttaga taaataataa aggtcgattt 2820  ttactttgtt aaatatcaaa tatgtcatta tctgataaag atacaaaaac acacggtgat 2880  tatcaaccat ctaacgaaca gatattacaa aaaatacgtc ggactatgga aaacgaagct 2940  gatagcctca atagaagaag cattaaagaa attgttgtag atgttatgaa gaattgggat 3000  catcctcaac gaagaaatag ataaagttct aaactggaaa atgatacat  taaacgattt 3060  agatcatcta aatacagatg ataatattaa ggaaatcata caatgtctga ttagagaatt 3120  tgcgtttaaa aagatcaatt ctattatgta tagttatgct atggtaaaac tcaattcaga 3180  taacgaacat tgaaagataa aattaaggat tattttatag aaactattct taaagacaaa 3240  cgtggttata acaaaagcc  attacccgga ttggaaacta aaatactaga tagtattata 3300  agatttttaaa aacataaaat taataggttt ttatagattg acttattata tacaatatgg 3360  ataaaagata tatatcaact agaaagttga atgacggatt cttaattta  tattatgatt 3420  caatagaaat tattgtcatg tcgtgtaatc attttataaa tatatcagcg ttactagcta 3480  agaaaaacaa ggactttaat gaatggctaa agatagaatc atttagagaa ataatagata 3540  ctttagataa aattaattac gatctaggac aacgatattg tgaagaactt acggcgcatc 3600  acattccagt gtaattattg aggtcaaagc tagtaactta atagatgaca ggacagctg
```

SEQ ID NO 2

LENGTH: 68

TYPE: DNA

ORGANISM: Artificial Sequence

OTHER INFORMATION: Doublestranded oligonucleotide referred to as JCA017

SEQUENCE:
```
    1 ctagacactt tatgtttttt aatatccggt cttaaaagct tcccggggat ccttatacgg
   60 ggaataat
```

SEQ ID NO 3

LENGTH: 65

TYPE: DNA

ORGANISM: Artificial Sequence

OTHER INFORMATION: Doublestranded oligonucleotide referred to as JCA018

SEQUENCE: 38
```
    1 attattcccc gtataaggat ccccgggaa gcttttaaga ccggatatta aaaacataa
   60 agtgt
```

SEQ ID NO 4

LENGTH: 60

TYPE: DNA

ORGANISM: Artificial Sequence

OTHER INFORMATION: Oligonucleotide referred to as RW178

SEQUENCE:
1  tcattatcgc gatatccgtg ttaactagct agctaatttt tattcccggg atccttatca

SEQ ID NO 5

LENGTH: 60

TYPE: DNA

ORGANISM: Artificial Sequence

OTHER INFORMATION: Oligonucleotide referred to as RW179

1  gtataaggat cccgggaata aaaattagct agctagttaa cacggatatc gcgataatga

SEQ ID NO 6

LENGTH: 66

TYPE: DNA

ORGANISM: Artificial Sequence

OTHER INFORMATION: Synthetic oligonucleotide referred to as RW10

SEQUENCE: 58
1  gaaaaattta aagtcgacct gttttgttga gttgtttgcg tggtaaccaa tgcaaatctg 60  gtcact

SEQ ID NO 7

LENGTH: 66

TYPE: DNA

ORGANISM: Artificial Sequence

OTHER INFORMATION: Synthetic oligonucleotide referred to as RW11

SEQUENCE:
1  tctagcaaga ctgactattg caaaagaag cactatttcc tccattacga tacaaactta 60  acggat

SEQ ID NO 8

LENGTH: 87

TYPE: DNA

ORGANISM: Artificial Sequence

OTHER INFORMATION: Synthetic oligonucleotide referred to as RW12

SEQUENCE:
1  atccgttaag tttgtatcgt aatggaggaa atagtgcttc ttttgcaat agtcagtctt 60  gctagaagtg accagatttg cattggt

SEQ ID NO 9

LENGTH: 49

TYPE: DNA

ORGANISM: Artificial Sequence

OTHER INFORMATION: Synthetic oligonucleotide referred to as RW13

SEQUENCE:
1  taccacgcaa acaactcaac aaaacaggtc gactttaaat ttttctgca

SEQ ID NO 10

LENGTH: 21

ORGANISM: Artificial Sequence

OTHER INFORMATION: Primer for amplifying AIV probe referred to as 11526JY

SEQUENCE:

-continued

1 ACGAAGCCAGCAGCGGAGTGA

SEQ ID NO 11

LENGTH: 21

ORGANISM: Artificial Sequence

OTHER INFORMATION: Primer for amplifying AIV probe referred to as 11531JY

SEQUENCE:
1 TCAGCACCAGCAGTTCGGCGT

SEQ ID NO 12

LENGTH: 24

ORGANISM: Artificial Sequence

OTHER INFORMATION: Primer for PCR amplification of the F8 arms plus insert, referred to as 11339CXL

SEQUENCE:
1 GTAGTGATCAAAATACAGAACCAT

SEQ ID NO 13

LENGTH: 24

ORGANISM: Artificial Sequence

OTHER INFORMATION: Primer for PCR amplification of the F8 arms plus insert, referred to as 11340CXL

SEQUENCE:
1 GAATCCGTCATTCAACTTTCTAGT

SEQ ID NO 14

LENGTH: 4737

OTHER INFORMATION: F8 right arm (1-1429), H6 promoter (1516-1639), AIV synethetic H5 HA (1640-3334), and F8 left arm (3362-4737) determined through sequence analysis

SEQUENCE:
```
  1 GACCCTTTAC AAGAATAAAA GAAGAAACAA CTGTGAAATA GTTTATAAAT
    CTGGGAAATG TTCTTATTTT CTTCTTTGTT GACACTTTAT CAAATATTTA

51 GTAATTCGTA TGCAGAAAAC GATAATATAT TTTGGTATGA GAAATCTAAA
    CATTAAGCAT ACGTCTTTTG CTATTATATA AAACCATACT CTTTAGATTT

101 GGAGACATAG TTTGTATAGA CATGCGCTCT TCCGATGAGA TATTCGATGC
    CCTCTGTATC AAACATATCT GTACGCGAGA AGGCTACTCT ATAAGCTACG

151 TTTTCTAATG TATCATATAG CTACAAGATA TGCCTATCAT GATGATGATA
    AAAAGATTAC ATAGTATATC GATGTTCTAT ACGGATAGTA CTACTACTAT

201 TATATCTACA AATAGTGTTA TATTATTCTA ATAATCAAAA TGTTATATCT
    ATATAGATGT TTATCACAAT ATAATAAGAT TATTAGTTTT ACAATATAGA

251 TATATTACGA AAAATAAATA CGTTAAGTAT ATAAGAAATA AAACTAGAGA
    ATATAATGCT TTTTATTTAT GCAATTCATA TATTCTTTAT TTTGATCTCT

301 CGATATTCAT AAAGTAAAAA TATTAGCTCT AGAAGACTTT ACAACGGAAG
    GCTATAAGTA TTTCATTTTT ATAATCGAGA TCTTCTGAAA TGTTGCCTTC

351 AAATATATTG TTGGATTAGT AATATATAAC AGCGTAGCTG CACGGTTTTG
    TTTATATAAC AACCTAATCA TTATATATTG TCGCATCGAC GTGCCAAAAC

401 ATCATTTTCC AACAATATAA ACCAATGAAG GAGGACGACT CATCAAACAT
    TAGTAAAAGG TTGTTATATT TGGTTACTTC CTCCTGCTGA GTAGTTTGTA

451 AAATAACATT CACGGAAAAT ATTCAGTATC AGATTTATCA CAAGATGATT
    TTTATTGTAA GTGCCTTTTA TAAGTCATAG TCTAAATAGT GTTCTACTAA

501 ATGTTATTGA ATGTATAGAC GGATCTTTTG ATTCGATCAA GTATAGAGAT
    TACAATAACT TACATATCTG CCTAGAAAAC TAAGCTAGTT CATATCTCTA

551 ATAAAGGTTA TAATAATGAA GAATAACGGT TACGTTAATT GTAGTAAATT
    TATTTCCAAT ATTATTACTT CTTATTGCCA ATGCAATTAA CATCATTTAA

601 ATGTAAAATG CGGAATAAAT ACTTTTCTAG ATGGTTGCGT CTTTCTACTT
    TACATTTTAC GCCTTATTTA TGAAAAGATC TACCAACGCA GAAAGATGAA
```

```
-continued
 651 CTAAAGCATT ATTAGACATT TACAATAATA AGTCAGTAGA TAATGCTATT
     GATTTCGTAA TAATCTGTAA ATGTTATTAT TCAGTCATCT ATTACGATAA 701 GTTAAAGTCT ATGGTAAAGG TAAGAAACTT ATTATAACAG GATTTTATCT
     CAATTTCAGA TACCATTTCC ATTCTTTGAA TAATATTGTC CTAAAATAGA 751 CAAACAAAAT ATGATACGTT ATGTTATTGA GTGGATAGGG GATGATTTTA
     GTTTGTTTTA TACTATGCAA TACAATAACT CACCTATCCC CTACTAAAAT 801 CAAACGATAT ATACAAAATG ATTAATTTCT ATAATGCGTT ATTCGGTAAC
     GTTTGCTATA TATGTTTTAC TAATTAAAGA TATTACGCAA TAAGCCATTG 851 GATGAATTAA AAATAGTATC CTGTGAAAAC ACTCTATGCC CGTTTATAGA
     CTACTTAATT TTTATCATAG GACACTTTTG TGAGATACGG GCAAATATCT 901 ACTTGGTAGA TGCTATTATG GTAAAAAATG TAAGTATATA CACGGAGATC
     TGAACCATCT ACGATAATAC CATTTTTTAC ATTCATATAT GTGCCTCTAG 951 AATGTGATAT CTGTGGTCTA TATATACTAC ACCCTACCGA TATTAACCAA
     TTACACTATA GACACCAGAT ATATATGATG TGGGATGGCT ATAATTGGTT 1001 CGAGTTTCTC ACAAGAAAAC TTGTTTAGTA GATAGAGATT CTTTGATTGT
     GCTCAAAGAG TGTTCTTTTG AACAAATCAT CTATCTCTAA GAAACTAACA 1051 GTTTAAAAGA AGTACCAGTA AAAAGTGTGG CATATGCATA GAAGAAATAA
     CAAATTTTCT TCATGGTCAT TTTTCACACC GTATACGTAT CTTCTTTATT 1101 ACAAAAAACA TATTTCCGAA CAGTATTTTG GAATTCTCCC AAGTTGTAAA
     TGTTTTTTGT ATAAAGGCTT GTCATAAAAC CTTAAGAGGG TTCAACATTT 1151 CATATTTTTT GCCTATCATG TATAAGACGT TGGGCAGATA CTACCAGAAA
     GTATAAAAAA CGGATAGTAC ATATTCTGCA ACCCGTCTAT GATGGTCTTT 1201 TACAGATACT GAAAATACGT GTCCTGAATG TAGAATAGTT TTTCCTTTCA
     ATGTCTATGA CTTTTATGCA CAGGACTTAC ATCTTATCAA AAAGGAAAGT 1251 TAATACCCAG TAGGTATTGG ATAGATAATA AATATGATAA AAAAATATTA
     ATTATGGGTC ATCCATAACC TATCTATTAT TTATACTATT TTTTTATAAT 1301 TATAATAGAT ATAAGAAAAT GATTTTTACA AAAATACCTA TAAGAACAAT
     ATATTATCTA TATTCTTTTA CTAAAAATGT TTTTATGGAT ATTCTTGTTA 1351 AAAAATATAA TTACATTTAC GGAAAATAGC TGGTTTTAGT TTACCAACTT
     TTTTTATATT AATGTAAATG CCTTTTATCG ACCAAAATCA AATGGTTGAA 1401 AGAGTAATTA TCATATTGAA TCTATATTGC TAATTAGCTA ATAAAAACCC
     TCTCATTAAT AGTATAACTT AGATATAACG ATTAATCGAT TATTTTTGGG 1451 GGGTTAATTA ATTAGTCATC AGGCAGGGCG AGAACGAGAC TATCTGCTCG
     CCCAATTAAT TAATCAGTAG TCCGTCCCGC TCTTGCTCTG ATAGACGAGC 1501 TTAATTAATT AGAGCTTCTT TATTCTATAC TTAAAAAGTG AAAATAAATA
     AATTAATTAA TCTCGAAGAA ATAAGATATG AATTTTTCAC TTTTATTTAT 1551 CAAAGGTTCT TGAGGGTTGT GTTAAATTGA AAGCGAGAAA TAATCATAAA
     GTTTCCAAGA ACTCCCAACA CAATTTAACT TTCGCTCTTT ATTAGTATTT 1601 TTATTTCATT ATCGCGATAT CCGTTAAGTT TGTATCGTAA TGGAGAAAAT
     AATAAAGTAA TAGCGCTATA GGCAATTCAA ACATAGCATT ACCTCTTTTA 1651 CGTGCTGCTG CTGGCCATCG TGAGCCTGGT GAAAAGCGAT CAGATCTGCA
     GCACGACGAC GACCGGTAGC ACTCGGACCA CTTTTCGCTA GTCTAGACGT 1701 TCGGCTACCA CGCCAACAAC AGCACAGAGC AAGTGGACAC AATCATGGAA
     AGCCGATGGT GCGGTTGTTG TCGTGTCTCG TTCACCTGTG TTAGTACCTT 1751 AAGAACGTGA CCGTGACACA CGCCCAGGAC ATCCTGGAAA AGACACACAA
     TTCTTGCACT GGCACTGTGT GCGGGTCCTG TAGGACCTTT TCTGTGTGTT 1801 CGGGAAGCTG TGCGATCTGG ATGGAGTGAA GCCTCTGATC CTGAGAGATT
     GCCCTTCGAC ACGCTAGACC TACCTCACTT CGGAGACTAG GACTCTCTAA 1851 GCAGCGTGGC CGGATGGCTG CTGGGGAACC CAATGTGCGA CGAATTCATC
     CGTCGCACCG GCCTACCGAC GACCCCTTGG GTTACACGCT GCTTAAGTAG 1901 AACGTGCCCG AATGGAGCTA CATCGTGGAG AAGGCCAACC CAGCCAACGA
     TTGCACGGGC TTACCTCGAT GTAGCACCTC TTCCGGTTGG GTCGGTTGCT 1951 CCTGTGCTAC CCAGGGAACC TGAACGACTA CGAAGAACTG AAACACCTGC
     GGACACGATG GGTCCCTTGG ACTTGCTGAT GCTTCTTGAC TTTGTGGACG
```

-continued

```
2001  TGAGCAGAAT CAACCACTTT GAGAAAATCC AGATCATCCC CAAAAGCAGC
      ACTCGTCTTA GTTGGTGAAA CTCTTTTAGG TCTAGTAGGG GTTTTCGTCG

2051  TGGTCCGATC ACGAAGCCAG CAGCGGAGTG AGCAGCGCCT GCCCATACCA
      ACCAGGCTAG TGCTTCGGTC GTCGCCTCAC TCGTCGCGGA CGGGTATGGT

2101  GGGAAAGTCC AGCTTTTTTA GAAACGTGGT GTGGCTGATC AAAAAGAACA
      CCCTTTCAGG TCGAAAAAAT CTTTGCACCA CACCGACTAG TTTTTCTTGT

2151  GCGCCTACCC AACAATCAAG AGAAGCTACA ACAACACCAA CCAGGAAGAT
      CGCGGATGGG TTGTTAGTTC TCTTCGATGT TGTTGTGGTT GGTCCTTCTA

2201  CTGCTGGTGC TGTGGGGGAT CCACCACCCT AACGATGCCG CCGAGCAGAC
      GACGACCACG ACACCCCCTA GGTGGTGGGA TTGCTACGGC GGCTCGTCTG

2251  AAGGCTGTAC CAGAACCCAA CCACCTACAT CTCCGTGGGG ACAAGCACAC
      TTCCGACATG GTCTTGGGTT GGTGGATGTA GAGGCACCCC TGTTCGTGTG

2301  TGAACCAGAG ACTGGTGCCA AAAATCGCCA TCAGATCCAA AGTGAACGGG
      ACTTGGTCTC TGACCACGGT TTTTAGCGGT AGTCTAGGTT TCACTTGCCC

2351  CAGAGCGGAA GAATGGAGTT CTTCTGGACA ATCCTGAAAC CCAACGATGC
      GTCTCGCCTT CTTACCTCAA GAAGACCTGT TAGGACTTTG GGTTGCTACG

2401  CATCAACTTC GAGAGCAACG GAAACTTCAT CGCCCCAGAA TACGCCTACA
      GTAGTTGAAG CTCTCGTTGC CTTTGAAGTA GCGGGTCTT ATGCGGATGT

2451  AAATCGTGAA GAAAGGGGAC AGCGCCATCA TGAAAAGCGA ACTGGAATAC
      TTTAGCACTT CTTTCCCCTG TCGCGGTAGT ACTTTTCGCT TGACCTTATG

2501  GGCAACTGCA ACACCAAGTG CCAGACCCCA ATGGGGGCCA TCAACAGCAG
      CCGTTGACGT TGTGGTTCAC GGTCTGGGGT TACCCCCGGT AGTTGTCGTC

2551  CATGCCATTC CACAACATCC ACCCTCTGAC CATCGGGGAA TGCCCCAAAT
      GTACGGTAAG GTGTTGTAGG TGGGAGACTG GTAGCCCCTT ACGGGGTTTA

2601  ACGTGAAAAG CAACAGACTG GTGCTGGCCA CCGGGCTGAG AAACAGCCCT
      TGCACTTTTC GTTGTCTGAC CACGACCGGT GGCCCGACTC TTTGTCGGGA

2651  CAGAGAGAGA CCAGAGGACT GTTTGGAGCC ATCGCCGGCT TTATCGAGGG
      GTCTCTCTCT GGTCTCCTGA CAAACCTCGG TAGCGGCCGA AATAGCTCCC

2701  AGGATGGCAG GGAATGGTGG ATGGCTGGTA CGGATACCAC CACAGCAACG
      TCCTACCGTC CCTTACCACC TACCGACCAT GCCTATGGTG GTGTCGTTGC

2751  AGCAGGGGAG CGGATACGCC GCCGACAAAG AATCCACCCA GAAGGCCATC
      TCGTCCCCTC GCCTATGCGG CGGCTGTTTC TTAGGTGGGT CTTCCGGTAG

2801  GACGGCGTGA CCAACAAAGT GAACAGCATC ATCGACAAAA TGAACACCCA
      CTGCCGCACT GGTTGTTTCA CTTGTCGTAG TAGCTGTTTT ACTTGTGGGT

2851  GTTTGAGGCC GTGGGAAGGG AGTTTAACAA CCTGGAAAGG AGAATCGAGA
      CAAACTCCGG CACCCTTCCC TCAAATTGTT GGACCTTTCC TCTTAGCTCT

2901  ACCTGAACAA GAAGATGGAG GACGGATTCC TGGATGTGTG GACCTACAAC
      TGGACTTGTT CTTCTACCTC CTGCCTAAGG ACCTACACAC CTGGATGTTG

2951  GCCGAACTGC TGGTGCTGAT GGAAAACGAG AGAACCCTGG ACTTTCACGA
      CGGCTTGACG ACCACGACTA CCTTTTGCTC TCTTGGGACC TGAAAGTGCT

3001  CAGCAACGTG AAGAACCTGT ACGACAAAGT GAGGCTGCAG CTGAGGGATA
      GTCGTTGCAC TTCTTGGACA TGCTGTTTCA CTCCGACGTC GACTCCCTAT

3051  ACGCCAAGGA GCTGGGCAAC GGCTGCTTCG AGTTCTACCA CAAATGCGAT
      TGCGGTTCCT CGACCCGTTG CCGACGAAGC TCAAGATGGT GTTTACGCTA

3101  AACGAATGCA TGGAAAGCAT CAGAAACGGA ACCTACAACT ACCCCCAGTA
      TTGCTTACGT ACCTTTCGTA GTCTTTGCCT TGGATGTTGA TGGGGGTCAT

3151  CAGCGAAGAA GCCAGACTGA AAAGAGAAGA AATCTCCGGA GTGAAACTGG
      GTCGCTTCTT CGGTCTGACT TTTCTCTTCT TTAGAGGCCT CACTTTGACC

3201  AATCCATCGG AACCTACCAG ATCCTGAGCA TCTACAGCAC AGTGGCCTCC
      TTAGGTAGCC TTGGATGGTC TAGGACTCGT AGATGTCGTG TCACCGGAGG

3251  TCCCTGGCCC TGGCCATCAT GATGGCCGGA CTGAGCCTGT GGATGTGCTC
      AGGGACCGGG ACCGGTAGTA CTACCGGCCT GACTCGGACA CCTACACGAG

3301  CAACGGAAGC CTGCAGTGCA GAATCTGCAT CTGACTCGAG TTTTTATTGA
      GTTGCCTTCG GACGTCACGT CTTAGACGTA GACTGAGCTC AAAAATAACT
```

```
3351  CTAGTTAATC ATAAGATAAA TAATATACAG CATTGTAACC ATCGTCATCC
      GATCAATTAG TATTCTATTT ATTATATGTC GTAACATTGG TAGCAGTAGG

3401  GTTATACGGG AATAATATT ACCATACAGT ATTATTAAAT TTTCTTACGA
      CAATATGCCC CTTATTATAA TGGTATGTCA TAATAATTTA AAAGAATGCT

3451  AGAATATAGA TCGGTATTTA TCGTTAGTTT ATTTTACATT TATTAATTAA
      TCTTATATCT AGCCATAAAT AGCAATCAAA TAAAATGTAA ATAATTAATT

3501  ACATGTCTAC TATTACCTGT TATGGAAATG ACAAATTTAG TTATATAATT
      TGTACAGATG ATAATGGACA ATACCTTTAC TGTTTAAATC AATATATTAA

3551  TATGATAAAA TTAAGATAAT AATAATGAAA TCAAATAATT ATGTAAATGC
      ATACTATTTT AATTCTATTA TTATTACTTT AGTTTATTAA TACATTTACG

3601  TACTAGATTA TGTGAATTAC GAGGAAGAAA GTTTACGAAC TGGAAAAAAT
      ATGATCTAAT ACACTTAATG CTCCTTCTTT CAAATGCTTG ACCTTTTTTA

3651  TAAGTGAATC TAAAATATTA GTCGATAATG TAAAAAAAAT AAATGATAAA
      ATTCACTTAG ATTTTATAAT CAGCTATTAC ATTTTTTTA TTTACTATTT

3701  ACTAACCAGT TAAAAACGGA TATGATTATA TACGTTAAGG ATATTGATCA
      TGATTGGTCA ATTTTTGCCT ATACTAATAT ATGCAATTCC TATAACTAGT

3751  TAAAGGAAGA GATACTTGCG GTTACTATGT ACACCAAGAT CTGGTATCTT
      ATTTCCTTCT CTATGAACGC CAATGATACA TGTGGTTCTA GACCATAGAA

3801  CTATATCAAA TTGGATATCT CCGTTATTCG CCGTTAAGGT AAATAAAATT
      GATATAGTTT AACCTATAGA GGCAATAAGC GGCAATTCCA TTTATTTTAA

3851  ATTAACTATT ATATATGTAA TGAATATGAT ATACGACTTA GCGAAATGGA
      TAATTGATAA TATATACATT ACTTATACTA TATGCTGAAT CGCTTTACCT

3901  ATCTGATATG ACAGAAGTAA TAGATGTAGT TGATAAATTA GTAGGAGGAT
      TAGACTATAC TGTCTTCATT ATCTACATCA ACTATTTAAT CATCCTCCTA

3951  ACAATGATGA AATAGCAGAA ATAATATATT TGTTTAATAA ATTTATAGAA
      TGTTACTACT TTATCGTCTT TATTATATAA ACAAATTATT TAAATATCTT

4001  AAATATATTG CTAACATATC GTTATCAACT GAATTATCTA GTATATTAAA
      TTTATATAAC GATTGTATAG CAATAGTTGA CTTAATAGAT CATATAATTT

4051  TAATTTTATA AATTTTAATA AAAAATACAA TAACGACATA AAAGATATTA
      ATTAAAATAT TTAAAATTAT TTTTTATGTT ATTGCTGTAT TTTCTATAAT

4101  AATCTTTAAT TCTTGATCTG AAAAACACAT CTATAAAACT AGATAAAAAG
      TTAGAAATTA AGAACTAGAC TTTTTGTGTA GATATTTTGA TCTATTTTTC

4151  TTATTCGATA AAGATAATAA TGAATCGAAC GATGAAAAAT TGGAAACAGA
      AATAAGCTAT TTCTATTATT ACTTAGCTTG CTACTTTTTA ACCTTTGTCT

4201  AGTTGATAAG CTAATTTTTT TCATCTAAAT AGTATTATTT TATTGAAGTA
      TCAACTATTC GATTAAAAAA AGTAGATTTA TCATAATAAA ATAACTTCAT

4251  CGAAGTTTTA CGTTAGATAA ATAATAAAGG TCGATTTTTA TTTTGTTAAA
      GCTTCAAAAT GCAATCTATT TATTATTTCC AGCTAAAAAT AAAACAATTT

4301  TATCAAATAT GTCATTATCT GATAAAGATA CAAAAACACA CGGTGATTAT
      ATAGTTTATA CAGTAATAGA CTATTTCTAT GTTTTTGTGT GCCACTAATA

4351  CAACCATCTA ACGAACAGAT ATTACAAAAA ATACGTCGGA CTATGGAAAA
      GTTGGTAGAT TGCTTGTCTA TAATGTTTTT TATGCAGCCT GATACCTTTT

4401  CGAAGCTGAT AGCCTCAATA GAAGAAGCAT TAAAGAAATT GTTGTAGATG
      GCTTCGACTA TCGGAGTTAT CTTCTTCGTA ATTTCTTTAA CAACATCTAC

4451  TTATGAAGAA TTGGGATCAT CCTCTCAACG AAGAAATAGA TAAAGTTCTA
      AATACTTCTT AACCCTAGTA GGAGAGTTGC TTCTTTATCT ATTTCAAGAT

4501  AACTGGAAAA ATGATACATT AAACGATTTA GATCATCTAA ATACAGATGA
      TTGACCTTTT TACTATGTAA TTTGCTAAAT CTAGTAGATT TATGTCTACT

4551  TAATATTAAG GAAATCATAC AATGTCTGAT TAGAGAATTT GCGTTTAAAA
      ATTATAATTC CTTTAGTATG TTACAGACTA ATCTCTTAAA CGCAAATTTT

4601  AGATCAATTC TATTATGTAT AGTTATGCTA TGGTAAAACT CAATTCAGAT
      TCTAGTTAAG ATAATACATA TCAATACGAT ACCATTTGA GTTAAGTCTA
```

```
4651 AACGAAACAT TGAAAGATAA AATTAAGGAT TATTTTATAG AAACTATTCT
     TTGCTTTGTA ACTTTCTATT TTAATTCCTA ATAAAATATC TTTGATAAGA

4701 TAAAGACAAA CGTGGTTATA AACAAAAGCC ATTACCC
     ATTTCTGTTT GCACCAATAT TTGTTTTCGG TAATGGG
```

SEQ ID NO 15

LENGTH: 1692

OTHER INFORMATION: nucleotide sequence of wild type H5 HA without cleavage sequence from plasmid pCRScript/HACK/Indonesia/03(modified)avipox SEQUENCE:
```
   (1) ATGGAGAAAATCGTGCTGCTGCTGGCCATCGTGAGCCTGGTGAAAAGCGATCAGATCTGCATCGGCTACC

(71) ACGCCAACAACAGCACAGAGCAAGTGGACACAATCATGGAAAAGAACGTGACCGTGACACACGCCCAGGA (141) CATCCTGGAAAAGACACACAACGGGAAGCTGTGCGATCTGGATGGAGTGAAGCCTCTGATCCTGAGAGAT (211) TGCAGCGTGGCCGGATGGCTGCTGGGGAACCCAATGTGCGACGAATTCATCAACGTGCCCGAATGGAGCT (281) ACATCGTGGAGAAGGCCAACCCAGCCAACGACCTGTGCTACCCAGGGAACCTGAACGACTACGAAGAACT (351) GAAACACCTGCTGAGCAGAATCAACCACTTTGAGAAAATCCAGATCATCCCCAAAAGCAGCTGGTCCGAT (421) CACGAAGCCAGCAGCGGAGTGAGCAGCGCCTGCCCATACCAGGGAAAGTCCAGCTTTTTTAGAAACGTGG (491) TGTGGCTGATCAAAAAGAACAGCGCCTACCCAACAATCAAGAGAAGCTACAACAACACCAACCAGGAAGA (561) TCTGCTGGTGCTGTGGGGATCCACCACCCTAACGATGCCGCCGAGCAGACAAGGCTGTACCAGAACCCA (631) ACCACCTACATCTCCGTGGGGACAAGCACACTGAACCAGAGACTGGTGCCAAAAATCGCCATCAGATCCA (701) AAGTGAACGGGCAGAGCGGAAGAATGGAGTTCTTCTGGACAATCCTGAAACCCAACGATGCCATCAACTT (771) CGAGAGCAACGGAAACTTCATCGCCCCAGAATACGCCTACAAAATCGTGAAGAAAGGGGACAGCGCCATC (841) ATGAAAAGCGAACTGGAATACGGCAACTGCAACACCAAGTGCCAGACCCCAATGGGGGCCATCAACAGCA (911) GCATGCCATTCCACAACATCCACCCTCTGACCATCGGGGAATGCCCCAAATACGTGAAAAGCAACAGACT (981) GGTGCTGGCCACCGGGCTGAGAAACAGCCCTCAGAGAGAGACCAGAGGACTGTTTGGAGCCATCGCCGGC (1051) TTTATCGAGGAGGATGGCAGGGAATGGTGGATGGCTGGTACGGATACCACCACAGCAACGAGCAGGGGA (1121) GCGGATACGCCGCCGACAAAGAATCCACCCAGAAGGCCATCGACGGCGTGACCAACAAAGTGAACAGCAT (1191) CATCGACAAAATGAACACCCAGTTTGAGGCCGTGGGAAGGGAGTTTAACAACCTGGAAAGGAGAATCGAG (1261) AACCTGAACAAGAAGATGGAGGACGGATTCCTGGATGTGTGGACCTACAACGCCGAACTGCTGGTGCTGA (1331) TGGAAAACGAGAGAACCCTGGACTTTCACGACAGCAACGTGAAGAACCTGTACGACAAAGTGAGGCTGCA (1401) GCTGAGGGATAACGCCAAGGAGCTGGGCAACGGCTGCTTCGAGTTCTACCACAAATGCGATAACGAATGC (1471) ATGGAAAGCATCAGAAACGGAACCTACAACTACCCCCAGTACAGCGAAGAAGCCAGACTGAAAAGAGAAG (1541) AAATCTCCGGAGTGAAACTGGAATCCATCGGAACCTACCAGATCCTGAGCATCTACAGCACAGTGGCCTC (1611) CTCCCTGGCCCTGGCCATCATGATGGCCGGACTGAGCCTGTGGATGTGCTCCAACGGAAGCCTGCAGTGC (1681) AGAATCTGCATC
```

SEQ ID NO 16

LENGTH: 564

OTHER INFORMATION: amino acid sequence of wild type H5 HA without cleavage sequence from plasmid pCRScript/HACK/Indonesia/03(modified)avipox

SEQUENCE:
```
  (1) MEKIVLLLAIVSLVKSDQICIGYHANNSTEQVDTIMEKNVTVTHAQDILE

(51) KTHNGKLCDLDGVKPLILRDCSVAGWLLGNPMCDEFINVPEWSYIVEKAN (101) PANDLCYPGNLNDYEELKHLLSRINHFEKIQIIPKSSWSDHEASSGVSSA (151) CPYQGKSSFFRNVVWLIKKNSAYPTIKRSYNNTNQEDLLVLWGIHHPNDA (201) AEQTRLYQNPTTYISVGTSTLNQRLVPKIAIRSKVNGQSGRMEFFWTILK (251) PNDAINFESNGNFIAPEYAYKIVKKGDSAIMKSELEYGNCNTKCQTPMGA
```

(301) INSSMPFHNIHPLTIGECPKYVKSNRLVLATGLRNSPQRETRGLFG (347) AIAGFIEGGWQGMVDGWYGYHHSNEQGSGYAADKESTQKAIDGVTNKVNS (397) IIDKMNTQFEAVGREFNNLERRIENLNKKMEDGFLDVWTYNAELLVLMEN (447) ERTLDFHDSNVKNLYDKVRLQLRDNAKELGNGCFEFYHKCDNECMESIRN (497) GTYNYPQYSEEARLKREEISGVKLESIGTYQILSIYSTVASSLALAIMMA (547) GLSLWMCSNGSLQCRICI

SEQ ID NO 17
LENGTH: 564

OTHER INFORMATION: Predicted amino acid sequence of H5 HA without cleavage sequence SEQUENCE:
```
  1 MEKIVLLLAI VSLVKSDQIC IGYHANNSTE QVDTIMEKNV TVTHAQDILE
 51 KTHNGKLCDL DGVKPLILRD CSVAGWLLGN PMCDEFINVP EWSYIVEKAN
101 PANDLCYPGN LNDYEELKHL LSRINHFEKI QIIPKSSWSD HEASSGVSSA
151 CPYQGKSSFF RNVVWLIKKN SAYPTIKRSY NNTNQEDLLV LWGIHHPNDA
201 AEQTRLYQNP TTYISVGTST LNQRLVPKIA IRSKVNGQSG RMEFFWTILK
251 PNDAINFESN GNFIAPEYAY KIVKKGDSAI MKSELEYGNC NTKCQTPMGA
301 INSSMPFHNI HPLTIGECPK YVKSNRLVLA TGLRNSPQRE TRGLFGAIAG
351 FIEGGWQGMV DGWYGYHHSN EQGSGYAADK ESTQKAIDGV TNKVNSIIDK
401 MNTQFEAVGR EFNNLERRIE NLNKKMEDGF LDVWTYNAEL LVLMENERTL
451 DFHDSNVKNL YDKVRLQLRD NAKELGNGCF EFYHKCDNEC MESIRNGTYN
501 YPQYSEEARL KREEISGVKL ESIGTYQILS IYSTVASSLA LAIMMAGLSL
551 WMCSNGSLQC RICI*
```

SEQ ID NO 18
LENGTH: 3956

ORGANISM: Artificial Sequence

OTHER INFORMATION: Nucleotide sequence of C5 right arm (43-1578), H6 promoter (1675-1799) AIV synthetic H5 HA (1800-3494), and C5 left arm (3529-3932) in plasmid SEQUENCE:
```
  1 GGAAACAGCT ATGACCATGA TTACGAATTG CGGCCGCAAT TCTGAATGTT
    CCTTTGTCGA TACTGGTACT AATGCTTAAC GCCGGCGTTA AGACTTACAA 51 AAATGTTATA CTTTGGATGA AGCTATAAAT ATGCATTGGA AAAATAATCC
    TTTACAATAT GAAACCTACT TCGATATTTA TACGTAACCT TTTTATTAGG 101 ATTTAAAGAA AGGATTCAAA TACTACAAAA CCTAAGCGAT AATATGTTAA
    TAAATTTCTT TCCTAAGTTT ATGATGTTTT GGATTCGCTA TTATACAATT 151 CTAAGCTTAT TCTTAACGAC GCTTTAAATA TACACAAATA AACATAATTT
    GATTCGAATA AGAATTGCTG CGAAATTTAT ATGTGTTTAT TTGTATTAAA 201 TTGTATAACC TAACAAATAA CTAAAACATA AAATAATAA AAGGAAATGT
    AACATATTGG ATTGTTATT GATTTGTAT TTTTATTATT TTCCTTTACA 251 AATATCGTAA TTATTTTACT CAGGAATGGG GTTAAATATT TATATCACGT
    TTATAGCATT AATAAAATGA GTCCTTACCC CAATTTATAA ATATAGTGCA 301 GTATATCTAT ACTGTTATCG TATACTCTTT ACAATTACTA TTACGAATAT
    CATATAGATA TGACAATAGC ATATGAGAAA TGTTAATGAT AATGCTTATA
                                                    7927.DC 351 GCAAGAGATA ATAAGATTAC GTATTTAAGA GAATCTTGTC ATGATAATTG
    CGTTCTCTAT TATTCTAATG CATAAATTCT CTTAGAACAG TACTATTAAC
    7927.DC
```

```
                           -continued
 401  GGTACGACAT AGTGATAAAT GCTATTTCGC ATCGTTACAT AAAGTCAGTT
       CCATGCTGTA TCACTATTTA CGATAAAGCG TAGCAATGTA TTTCAGTCAA 451  GGAAAGATGG ATTTGACAGA TGTAACTTAA TAGGTGCAAA AATGTTAAAT
       CCTTTCTACC TAAACTGTCT ACATTGAATT ATCCACGTTT TTACAATTTA
                      7696.CXL 501  AACAGCATTC TATCGGAAGA TAGGATACCA GTTATATTAT ACAAAAATCA
       TTGTCGTAAG ATAGCCTTCT ATCCTATGGT CAATATAATA TGTTTTTAGT 551  CTGGTTGGAT AAAACAGATT CTGCAATATT CGTAAAAGAT GAAGATTACT
       GACCAACCTA TTTTGTCTAA GACGTTATAA GCATTTTCTA CTTCTAATGA 601  GCGAATTTGT AAACTATGAC AATAAAAAGC CATTTATCTC AACGACATCG
       CGCTTAAACA TTTGATACTG TTATTTTTCG GTAAATAGAG TTGCTGTAGC 651  TGTAATTCTT CCATGTTTTA TGTATGTGTT TCAGATATTA TGAGATTACT
       ACATTAAGAA GGTACAAAAT ACATACACAA AGTCTATAAT ACTCTAATGA 701  ATAAACTTTT TGTATACTTA TATTCCGTAA ACTATATTAA TCATGAAGAA
       TATTTGAAAA ACATATGAAT ATAAGGCATT TGATATAATT AGTACTTCTT 751  AATGAAAAAG TATAGAAGCT GTTCACGAGC GGTTGTTGAA ACAACAAAA
       TTACTTTTTC ATATCTTCGA CAAGTGCTCG CCAACAACTT TTGTTGTTTT
                           7926.DC 801  TTATACATTC AAGATGGCTT ACATATACGT CTGTGAGGCT ATCATGGATA
       AATATGTAAG TTCTACCGAA TGTATATGCA GACACTCCGA TAGTACCTAT 851  ATGACAATGC ATCTCTAAAT AGGTTTTTGG ACAATGGATT CGACCCTAAC
       TACTGTTACG TAGAGATTTA TCCAAAAACC TGTTACCTAA GCTGGGATTG 901  ACGGAATATG GTACTCTACA ATCTCCTCTT GAAATGGCTG TAATGTTCAA
       TGCCTTATAC CATGAGATGT TAGAGGAGAA CTTTACCGAC ATTACAAGTT 951  GAATACCGAG CTATAAAAA TCTTGATGAG GTATGGAGCT AAACCTGTAG
       CTTATGGCTC CGATATTTTT AGAACTACTC CATACCTCGA TTTGGACATC
                       7697.CXL 1001  TTACTGAATG CACAACTTCT TGTCTGCATG ATGCGGTGTT GAGAGACGAC
       AATGACTTAC GTGTTGAAGA ACAGACGTAC TACGCCACAA CTCTCTGCTG 1051  TACAAAATAG TGAAAGATCT GTTGAAGAAT AACTATGTAA ACAATGTTCT
       ATGTTTTATC ACTTTCTAGA CAACTTCTTA TTGATACATT TGTTACAAGA 1101  TTACAGCGGA GGCTTTACTC CTTTGTGTTT GGCAGCTTAC CTTAACAAAG
       AATGTCGCCT CCGAAATGAG GAAACACAAA CCGTCGAATG GAATTGTTTC 1151  TTAATTTGGT TAAACTTCTA TTGGCTCATT CGGCGGATGT AGATATTTCA
       AATTAAACCA ATTTGAAGAT AACCGAGTAA GCCGCCTACA TCTATAAAGT 1201  AACACGGATC GGTTAACTCC TCTACATATA GCCGTATCAA ATAAAAATTT
       TTGTGCCTAG CCAATTGAGG AGATGTATAT CGGCATAGTT TATTTTTAAA
                       7925.DC 1251  AACAATGGTT AAACTTCTAT TGAACAAAGG TGCTGATACT GACTTGCTGG
       TTGTTACCAA TTTGAAGATA ACTTGTTTCC ACGACTATGA CTGAACGACC 1301  ATAACATGGG ACGTACTCCT TTAATGATCG CTGTACAATC TGGAAATATT
       TATTGTACCC TGCATGAGGA AATTACTAGC GACATGTTAG ACCTTTATAA 1351  GAAATATGTA GCACACTACT TAAAAAAAAT AAAATGTCCA GAACTGGGAA
       CTTTATACAT CGTGTGATGA ATTTTTTTA TTTTACAGGT CTTGACCCTT 1401  AAATTGATCT TGCCAGCTGT AATTCATGGT AGAAAAGAAG TGCTCAGGCT
       TTTAACTAGA ACGGTCGACA TTAAGTACCA TCTTTTCTTC ACGAGTCCGA 1451  ACTTTTCAAC AAAGGAGCAG ATGTAAACTA CATCTTTGAA AGAAATGGAA
       TGAAAAGTTG TTTCCTCGTC TACATTTGAT GTAGAAACTT TCTTTACCTT
                                     7792.SL 1501  AATCATATAC TGTTTTGGAA TTGATTAAAG AAAGTTACTC TGAGACACAA
       TTAGTATATG ACAAAACCTT AACTAATTTC TTTCAATGAG ACTCTGTGTT
        7792.SL 1551  AAGAGGTAGC TGAAGTGGTA CTCTCAAAGG TACGTGACTA ATTAGCTATA
       TTCTCCATCG ACTTCACCAT GAGAGTTTCC ATGCACTGAT TAATCGATAT 1601  AAAAGGATCC GGGTTAATTA ATTAGTCATC AGGCAGGGCG AGAACGAGAC
       TTTTCCTAGG CCCAATTAAT TAATCAGTAG TCCGTCCCGC TCTTGCTCTG
                           H6p
```

```
1651 TATCTGCTCG TTAATTAATT AGAGCTTCTT TATTCTATAC TTAAAAAGTG
     ATAGACGAGC AATTAATTAA TCTCGAAGAA ATAAGATATG AATTTTTCAC

1701 AAAATAAATA CAAAGGTTCT TGAGGGTTGT GTTAAATTGA AAGCGAGAAA
     TTTTATTTAT GTTTCCAAGA ACTCCCAACA CAATTTAACT TTCGCTCTTT
                                                  H5 HA  M •

1751 TAATCATAAA TTATTTCATT ATCGCGATAT CCGTTAAGTT TGTATCGTAA
     ATTAGTATTT AATAAAGTAA TAGCGCTATA GGCAATTCAA ACATAGCATT
         11524JY

.. E K I    V L L    L A I V    S L V    K S D
1801 TGGAGAAAAT CGTGCTGCTG CTGGCCATCG TGAGCCTGGT GAAAAGCGAT
     ACCTCTTTTA GCACGACGAC GACCGGTAGC ACTCGGACCA CTTTTCGCTA
         11525JY

Q I C I   G Y H    A N N    S T E Q    V D T •
1851 CAGATCTGCA TCGGCTACCA CGCCAACAAC AGCACAGAGC AAGTGGACAC
     GTCTAGACGT AGCCGATGGT GCGGTTGTTG TCGTGTCTCG TTCACCTGTG

. I M E    K N V T    V T H    A Q D    I L E K •
1901 AATCATGGAA AAGAACGTGA CCGTGACACA CGCCCAGGAC ATCCTGGAAA
     TTAGTACCTT TTCTTGCACT GGCACTGTGT GCGGGTCCTG TAGGACCTTT

.. T H N    G K L    C D L D    G V K    P L I
1951 AGACACACA CGGGAAGCTG TGCGATCTGG ATGGAGTGAA GCCTCTGATC
     TCTGTGTGTT GCCCTTCGAC ACGCTAGACC TACCTCACTT CGGAGACTAG

L R D C    S V A    G W L    L G N P    M C D •
2001 CTGAGAGATT GCAGCGTGGC CGGATGGCTG CTGGGGAACC CAATGTGCGA
     GACTCTCTAA CGTCGCACCG GCCTACCGAC GACCCCTTGG GTTACACGCT

. E F I    N V P E    W S Y    I V E    K A N P •
2051 CGAATTCATC AACGTGCCCG AATGGAGCTA CATCGTGGAG AAGGCCAACC
     GCTTAAGTAG TTGCACGGGC TTACCTCGAT GTAGCACCTC TTCCGGTTGG

.. A N D    L C Y    P G N L    N D Y    E E L
2101 CAGCCAACGA CCTGTGCTAC CCAGGGAACC TGAACGACTA CGAAGAACTG
     GTCGGTTGCT GGACACGATG GGTCCCTTGG ACTTGCTGAT GCTTCTTGAC

K H L L    S R I    N H F    E K I Q    I I P •
2151 AAACACCTGC TGAGCAGAAT CAACCACTTT GAGAAAATCC AGATCATCCC
     TTTGTGGACG ACTCGTCTTA GTTGGTGAAA CTCTTTTAGG TCTAGTAGGG
                                       11626JY

. K S S    W S D H    E A S    S G V    S S A C •
2201 CAAAAGCAGC TGGTCCGATC ACGAAGCCAG CAGCGGAGTG AGCAGCGCCT
     GTTTTCGTCG ACCAGGCTAG TGCTTCGGTC GTCGCCTCAC TCGTCGCGGA
                                       11527JY

.. P Y Q    G K S    S F F R    N V V    W L I
2251 GCCCATACCA GGGAAAGTCC AGCTTTTTTA GAAACGTGGT GTGGCTGATC
     CGGGTATGGT CCCTTTCAGG TCGAAAAAAT CTTTGCACCA CACCGACTAG

K K N S    A Y P    T I K    R S Y N    N T N •
2301 AAAAAGAACA GCGCCTACCC AACAATCAAG AGAAGCTACA ACAACACCAA
     TTTTTCTTGT CGCGGATGGG TTGTTAGTTC TCTTCGATGT TGTTGTGGTT

. Q E D    L L V L    W G I    H H P    N D A A •
2351 CCAGGAAGAT CTGCTGGTGC TGTGGGGGAT CCACCACCCT AACGATGCCG
     GGTCCTTCTA GACGACCACG ACACCCCCTA GGTGGTGGGA TTGCTACGGC

.. E Q T    R L Y    Q N P T    T Y I    S V G
2401 CCGAGCAGAC AAGGCTGTAC CAGAACCCAA CCACCTACAT CTCCGTGGGG
     GGCTCGTCTG TTCCGACATG GTCTTGGGTT GGTGGATGTA GAGGCACCCC

T S T L    N Q R    L V P    K I A I    R S K •
2451 ACAAGCACAC TGAACCAGAG ACTGGTGCCA AAAATCGCCA TCAGATCCAA
     TGTTCGTGTG ACTTGGTCTC TGACCACGGT TTTTAGCGGT AGTCTAGGTT

. V N G    Q S G R    M E F    F W T    I L K P •
2501 AGTGAACGGG CAGAGCGGAA GAATGGAGTT CTTCTGGACA ATCCTGAAAC
     TCACTTGCCC GTCTCGCCTT CTTACCTCAA GAAGACCTGT TAGGACTTTG

.. N D A    I N F    E S N G    N F I    A P E
2551 CCAACGATGC CATCAACTTC GAGAGCAACG GAAACTTCAT CGCCCCAGAA
     GGTTGCTACG GTAGTTGAAG CTCTCGTTGC CTTTGAAGTA GCGGGGTCTT
```

```
       Y A Y K   I V K   K G D   S A I M   K S E •
2601 TACGCCTACA AAATCGTGAA GAAAGGGGAC AGCGCCATCA TGAAAAGCGA
     ATGCGGATGT TTTAGCACTT CTTTCCCCTG TCGCGGTAGT ACTTTTCGCT
                                  11528JY

. L E Y   G N C N   T K C   Q T P   M G A I •
2651 ACTGGAATAC GGCAACTGCA ACACCAAGTG CCAGACCCCA ATGGGGGCCA
     TGACCTTATG CCGTTGACGT TGTGGTTCAC GGTCTGGGGT TACCCCCGGT
                                  11529JY

. . N S S   M P F   H N I H   P L T   I G E
2701 TCAACAGCAG CATGCCATTC ACAACATCC ACCCTCTGAC CATCGGGGAA
     AGTTGTCGTC GTACGGTAAG GTGTTGTAGG TGGGAGACTG GTAGCCCCTT

C P K Y   V K S   N R L   V L A T   G L R •
2751 TGCCCCAAAT ACGTGAAAAG CAACAGACTG GTGCTGGCCA CCGGGCTGAG
     ACGGGGTTTA TGCACTTTTC GTTGTCTGAC CACGACCGGT GGCCCGACTC

. N S P   Q R E T   R G L   F G A   I A G F •
2801 AAACAGCCCT CAGAGAGAGA CCAGAGGACT GTTTGGAGCC ATCGCCGGCT
     TTTGTCGGGA GTCTCTCTCT GGTCTCCTGA CAAACCTCGG TAGCGGCCGA

. . I E G   G W Q   G M V D   G W Y   G Y H
2851 TTATCGAGGG AGGATGGCAG GGAATGGTGG ATGGCTGGTA CGGATACCAC
     AATAGCTCCC TCCTACCGTC CCTTACCACC TACCGACCAT GCCTATGGTG

H S N E   Q G S   G Y A   A D K E   S T Q •
2901 CACAGCAACG AGCAGGGGAG CGGATACGCC GCCGACAAAG AATCCACCCA
     GTGTCGTTGC TCGTCCCCTC GCCTATGCGG CGGCTGTTTC TTAGGTGGGT

. K A I   D G V T   N K V   N S I   I D K M •
2951 GAAGGCCATC GACGGCGTGA CCAACAAAGT GAACAGCATC ATCGACAAAA
     CTTCCGGTAG CTGCCGCACT GGTTGTTTCA CTTGTCGTAG TAGCTGTTTT

. . N T Q   F E A   V G R E   F N N   L E R
3001 TGAACACCCA GTTTGAGGCC GTGGGAAGGG AGTTTAACAA CCTGGAAAGG
     ACTTGTGGGT CAAACTCCGG CACCCTTCCC TCAAATTGTT GGACCTTTCC

R I E N   L N K   K M E   D G F L   D V W •
3051 AGAATCGAGA ACCTGAACAA GAAGATGGAG GACGGATTCC TGGATGTGTG
     TCTTAGCTCT TGGACTTGTT CTTCTACCTC CTGCCTAAGG ACCTACACAC
                                  11530JY

. T Y N   A E L L   V L M   E N E   R T L D •
3101 GACCTACAAC GCCGAACTGC TGGTGCTGAT GGAAAACGAG AGAACCCTGG
     CTGGATGTTG CGGCTTGACG ACCACGACTA CCTTTTGCTC TCTTGGGACC
                                  11531JY

. . F H D   S N V   K N L Y   D K V   R L Q
3151 ACTTTCACGA CAGCAACGTG AAGAACCTGT ACGACAAAGT GAGGCTGCAG
     TGAAAGTGCT GTCGTTGCAC TTCTTGGACA TGCTGTTTCA CTCCGACGTC

L R D N   A K E   L G N   G C F E   F Y H •
3201 CTGAGGGATA ACGCCAAGGA GCTGGGCAAC GGCTGCTTCG AGTTCTACCA
     GACTCCCTAT TGCGGTTCCT CGACCCGTTG CCGACGAAGC TCAAGATGGT

. K C D   N E C M   E S I   R N G   T Y N Y •
3251 CAAATGCGAT AACGAATGCA TGGAAAGCAT CAGAAACGGA ACCTACAACT
     GTTTACGCTA TTGCTTACGT ACCTTTCGTA GTCTTTGCCT TGGATGTTGA

. . P Q Y   S E E   A R L K   R E E   I S G
3301 ACCCCCAGTA CAGCGAAGAA GCCAGACTGA AAAGAGAAGA ATCTCCGGA
     TGGGGGTCAT GTCGCTTCTT CGGTCTGACT TTTCTCTTCT TTAGAGGCCT

V K L E   S I G   T Y Q   I L S I   Y S T •
3351 GTGAAACTGG AATCCATCGG AACCTACCAG ATCCTGAGCA TCTACAGCAC
     CACTTTGACC TTAGGTAGCC TTGGATGGTC TAGGACTCGT AGATGTCGTG

. V A S   S L A L   A I M   M A G   L S L W •
3401 AGTGGCCTCC TCCCTGGCCC TGGCCATCAT GATGGCCGGA CTGAGCCTGT
     TCACCGGAGG AGGGACCGGG ACCGGTAGTA CTACCGGCCT GACTCGGACA
                                  11532JY

. . M C S   N G S   L Q C R   I C I   *
3451 GGATGTGCTC CAACGGAAGC CTGCAGTGCA GAATCTGCAT CTGACTCGAG
     CCTACACGAG GTTGCCTTCG GACGTCACGT CTTAGACGTA GACTGAGCTC
                                  11533JY              C5L

3501 TTTTTATTGA CTAGTTAATC ACGGCCGCTT ATAAAGATCT AAAATGCATA
     AAAATAACT GATCAATTAG TGCCGGCGAA TATTTCTAGA TTTTACGTAT
                                  7928.DC
```

-continued

```
3551 ATTTCTAAAT AATGAAAAAA AGTACATCAT GAGCAACGCG TTAGTATATT
     TAAAGATTTA TTACTTTTTT TCATGTAGTA CTCGTTGCGC AATCATATAA

3601 TTACAATGGA GATTAACGCT CTATACCGTT CTATGTTTAT TGATTCAGAT
     AATGTTACCT CTAATTGCGA GATATGGCAA GATACAAATA ACTAAGTCTA
                        7793.SL

3651 GATGTTTTAG AAAAGAAAGT TATTGAATAT GAAAACTTTA ATGAAGATGA
     CTACAAAATC TTTTCTTTCA ATAACTTATA CTTTTGAAAT TACTTCTACT

3701 AGATGACGAC GATGATTATT GTTGTAAATC TGTTTTAGAT GAAGAAGATG
     TCTACTGCTG CTACTAATAA CAACATTTAG ACAAAATCTA CTTCTTCTAC

3751 ACGCGCTAAA GTATACTATG GTTACAAAGT ATAAGTCTAT ACTACTAATG
     TGCGCGATTT CATATGATAC CAATGTTTCA TATTCAGATA TGATGATTAC

3801 GCGACTTGTG CAAGAAGGTA TAGTATAGTG AAAATGTTGT TAGATTATGA
     CGCTGAACAC GTTCTTCCAT ATCATATCAC TTTTACAACA ATCTAATACT

3851 TTATGAAAAA CCAAATAAAT CAGATCCATA TCTAAAGGTA TCTCCTTTGC
     AATACTTTTT GGTTTATTTA GTCTAGGTAT AGATTTCCAT AGAGGAAACG
                                                   7929.DC

3901 ACATAATTTC ATCTATTCCT AGTTTAGAAT ACCTGCAGCC AAGCTTGGCA
     TGTATTAAAG TAGATAAGGA TCAAATCTTA TGGACGTCGG TTCGAACCGT

3951 CTGGCCGTCG TTTTAC
     GACCGGCAGC AAAATG
        M13F
```

SEQ ID NO 19

LENGTH: 6551

OTHER INFORMATION: Theoretical sequence of entire vector

SEQUENCE:

gcgcccaatacgcaaaccgcctctccccgcgcgttggccgattcattaatgcagctggcacgacaggtttcccgact ggaaagcgggcagtgagcgcaacgcaattaatgtgagttagctcactcattaggcaccccaggctttacactttatg cttccggctcgtatgttgtgtggaattgtgagcggataacaatttcacacaggaaacagctatgaccatgattacga attgcggccgcaattctgaatgttaaatgttatactttggatgaagctataaatatgcattggaaaaataatccatt taaagaaaggattcaaatactacaaaacctaagcgataatatgttaactaagcttattcttaacgacgctttaaata tacacaaataaacataattttgtataacctaacaaataactaaaacataaaaataataaaaggaaatgtaatatcg taattattttactcaggaatggggttaaatatttatatcacgtgtatatctatactgttatcgtatactctttacaa ttactattacgaatatgcaagagataataagattacgtatttaagagaatcttgtcatgataattgggtacgacata gtgataaatgctatttcgcatcgttacataaagtcagttggaaagatggatttgacagatgtaacttaataggtgca aaaatgttaaataacagcattctatcggaagataggataccagttatattatacaaaaatcactggttggataaaac agattctgcaatattcgtaaagatgaagattactgcgaatttgtaaactatgacaataaaaagccatttatctcaa cgacatcgtgtaattcttccatgttttatgtatgtgtttcagatattatgagattactataaactttttgtatactt atattccgtaaactatattaatcatgaagaaaatgaaaaagtatagaagctgttcacgagcggttgttgaaaacaac aaaattatacattcaagatggcttacatatacgtctgtgaggctatcatggataatgacaatgcatctctaaatagg ttttggacaatggattcgaccctaacacggaatatggtactctacaatctcctcttgaaatggctgtaatgttcaa gaataccgaggctataaaaatcttgatgaggtatggagctaaacctgtagttactgaatgcacaacttcttgtctgc atgatgcggtgttgagagacgactacaaaatagtgaaagatctgttgaagaataactatgtaaacaatgttctttac agcggaggctttactcctttgtgtttggcagcttaccttaacaaagttaatttggttaaacttctattggctcattc ggcggatgtagatatttcaaacacggatcggttaactcctctacatatagccgtatcaaataaaaatttaacaatgg ttaaacttctattgaacaaaggtgctgatactgacttgctggataacatgggacgtactcctttaatgatcgctgta caatctggaaatattgaaatatgtagcacactacttaaaaaaaataaaatgtccagaactgggaaaaattgatcttg ccagctgtaattcatggtagaaaagaagtgctcaggctacttttcaacaaaggagcagatgtaaactacatctttga -continued

```
aagaaatggaaaatcatatactgttttggaattgattaaagaaagttactctgagacacaaaagaggtagctgaagt ggtactctcaaaggtacgtgactaattagctataaaaaggatccggttaattaattagtcatcaggcagggcgaga acgagactatctgctcgttaattaattagagcttctttattctatacttaaaaagtgaaaataaatacaaaggttct tgagggttgtgttaaattgaaagcgagaaataatcataaattatttcattatcgcgatatccgttaagtttgtatcg taatggagaaaatcgtgctgctgctggccatcgtgagcctggtgaaaagcgatcagatctgcatcggctaccacgcc aacaacagcacagagcaagtggacacaatcatggaaaagaacgtgaccgtgacacacgcccaggacatcctggaaaa gacacacaacgggaagctgtgcgatctggatggagtgaagcctctgatcctgagagattgcagcgtggccggatggc tgctggggaacccaatgtgcgacgaattcatcaacgtgcccgaatggagctacatcgtggagaaggccaacccagcc aacgacctgtgctacccagggaacctgaacgactacgaagaactgaaacacctgctgagcagaatcaaccactttga gaaaatccagatcatcccccaaaagcagctggtccgatcacgaagccagcagcggagtgagcagcgcctgcccatacc agggaaagtccagcttttttagaaacgtggtgtggctgatcaaaaagaacagcgcctacccaacaatcaagagaagc tacaacaacaccaaccaggaagatctgctggtgctgtggggatccaccaccctaacgatgccgccgagcagacaag gctgtaccagaacccaaccacctacatctccgtggggacaagcacactgaaccagagactggtgccaaaaatcgcca tcagatccaaagtgaacgggcagagcggaagaatggagttcttctggacaatcctgaaacccaacgatgccatcaac ttcgagagcaacggaaacttcatcgccccagaatacgcctacaaaatcgtgaagaaaggggacagcgccatcatgaa aagcgaactggaatacggcaactgcaacaccaagtgccagaccccaatgggggccatcaacagcagcatgccattcc acaacatccaccctctgaccatcggggaatgccccaaatacgtgaaaagcaacagactggtgctggccaccgggctg agaaacagccctcagagagagaccagaggactgtttggagccatcgccggctttatcgagggaggatggcagggaat ggtggatggctggtacggataccaccacagcaacgagcagggagcggatacgccgccgacaaagaatccacccaga aggccatcgacggcgtgaccaacaaagtgaacagcatcatcgacaaaatgaacacccagtttgaggccgtgggaagg gagtttaacaacctggaaaggagaatcgagaacctgaacaagaagatggaggacggattcctggatgtgtggaccta caacgccgaactgctggtgctgatggaaaacgagagaaccctggactttcacgacagcaacgtgaagaacctgtacg acaaagtgaggctgcagctgagggataacgccaaggagctgggcaacggctgcttcgagttctaccacaaatgcgat aacgaatgcatggaaagcatcagaaacggaacctacaactaccccagtacagcgaagaagccagactgaaaagaga agaaatctccggagtgaaactggaatccatcggaacctaccagatcctgagcatctacagcacagtggcctcctccc tggccctggccatcatgatggccggactgagcctgtggatgtgctccaacggaagcctgcagtgcagaatctgcatc tgactcgagttttttattgactagttaatcacggccgcttataaagatctaaaatgcataatttctaaataatgaaaa aaagtacatcatgagcaacgcgttagtatattttacaatggagattaacgctctataccgttctatgtttattgatt cagatgatgttttagaaaagaaagttattgaatatgaaaactttaatgaagatgaagatgacgacgatgattattgt tgtaaatctgttttagatgaagaagatgacgcgctaaagtatactatggttacaaagtataagtctatactactaat ggcgacttgtgcaagaaggtatagtatagtgaaaatgttgttagattatgattatgaaaaaccaaataaatcagatc catatctaaaggtatctcctttgcacataatttcatctattcctagtttagaatacctgcagccaagcttggcactg gccgtcgttttacaacgtcgtgactgggaaaaccctggcgttacccaacttaatcgccttgcagcacatccccttt cgccagctggcgtaatagcgaagaggcccgcaccgatcgcccttcccaacagttgcgcagcctgaatggcgaatggc gcctgatgcggtattttctccttacgcatctgtgcggtatttcacaccgcatatggtgcactctcagtacaatctgc tctgatgccgcatagttaagccagccccgacacccgccaacacccgctgacgcgccctgacgggcttgtctgctccc ggcatccgcttacagacaagctgtgaccgtctccgggagctgcatgtgtcagaggttttcaccgtcatcaccgaaac gcgcgagacgaaagggcctcgtgatacgcctatttttataggttaatgtcatgataataatggtttcttagacgtca ggtggcacttttcggggaaatgtgcgcggaacccctatttgtttatttttctaaatacattcaaatatgtatccgct catgagacaataaccctgataaatgcttcaataatattgaaaaaggaagagtatgagtattcaacatttccgtgtcg cccttattccctttttttgcggcattttgccttcctgtttttgctcacccagaaacgctggtgaaagtaaaagatgct
```

-continued

```
gaagatcagttgggtgcacgagtgggttacatcgaactggatctcaacagcggtaagatccttgagagttttcgccc cgaagaacgttttccaatgatgagcacttttaaagttctgctatgtggcgcggtattatcccgtattgacgccgggc aagagcaactcggtcgccgcatacactattctcagaatgacttggttgagtactcaccagtcacagaaagcatctt acggatggcatgacagtaagagaattatgcagtgctgccataaccatgagtgataacactgcggccaacttacttct gacaacgatcggaggaccgaaggagctaaccgcttttttgcacaacatggggatcatgtaactcgccttgatcgtt gggaaccggagctgaatgaagccataccaaacgacgagcgtgacaccacgatgcctgtagcaatggcaacaacgttg cgcaaactattaactggcgaactacttactctagcttcccggcaacaattaatagactggatggaggcggataaagt tgcaggaccacttctgcgctcggcccttccggctggctggtttattgctgataaatctggagccggtgagcgtgggt ctcgcggtatcattgcagcactggggccagatggtaagccctcccgtatcgtagttatctacacgacggggagtcag gcaactatggatgaacgaaatagacagatcgctgagataggtgcctcactgattaagcattggtaactgtcagacca agtttactcatatatactttagattgatttaaaacttcattttaatttaaaaggatctaggtgaagatcctttttg ataatctcatgaccaaaatcccttaacgtgagttttcgttccactgagcgtcagaccccgtagaaaagatcaaagga tcttcttgagatccttttttttctgcgcgtaatctgctgcttgcaaacaaaaaaaccaccgctaccagcggtggtttg tttgccggatcaagagctaccaactctttttccgaaggtaactggcttcagcagagcgcagataccaaatactgtcc ttctagtgtagccgtagttaggccaccacttcaagaactctgtagcaccgcctacatacctcgctctgctaatcctg ttaccagtggctgctgccagtggcgataagtcgtgtcttaccgggttggactcaagacgatagttaccggataaggc gcagcggtcgggctgaacggggggttcgtgcacacagcccagcttggagcgaacgacctacaccgaactgagatacc tacagcgtgagctatgagaaagcgccacgcttcccgaagggagaaaggcggacaggtatccggtaagcggcagggtc ggaacaggagagcgcacgagggagcttccaggggaaacgcctggtatctttatagtcctgtcgggtttcgccacct ctgacttgagcgtcgatttttgtgatgctcgtcaggggggcggagcctatggaaaaacgccagcaacgcggccttt tacggttcctggccttttgctggccttttgctcacatgttcttcctgcgttatcccctgattctgtggataaccgt attaccgcctttgagtgagctgataccgctcgccgcagccgaacgaccgagcgcagcgagtcagtgagcgaggaagc ggaaga
```

SEQ ID NO 20
LENGTH: 25

OTHER INFORMATION: Primer for PCR amplification of the vCP2241 C5 arms plus insert, referred to as 7931.D -continued

```
TATCACGTGTATATCTATACTGTTATCGTATACTCTTTACAATTACTATT

ACGAATATGCAAGAGATAATAAGATTACGTATTTAAGAGAATCTTGTCAT

GATAATTGGGTACGACATAGTGATAAATGCTATTTCGCATCGTTACATAA

AGTCAGTTGGAAAGATGGATTTGACAGATGTAACTTAATAGGTGCAAAAA

TGTTAAATAACAGCATTCTATCGGAAGATAGGATACCAGTTATATTATAC

AAAAATCACTGGTTGGATAAAACAGATTCTGCAATATTCGTAAAAGATGA

AGATTACTGCGAATTTGTAAACTATGACAATAAAAAGCCATTTATCTCAA

CGACATCGTGTAATTCTTCCATGTTTTATGTATGTGTTTCAGATATTATG

AGATTACTATAAACTTTTTGTATACTTATATTCCGTAAACTATATTAATC

ATGAAGAAAATGAAAAAGTATAGAAGCTGTTCACGAGCGGTTGTTGAAAA

CAACAAAATTATACATTCAAGATGGCTTACATATACGTCTGTGAGGCTAT

CATGGATAATGACAATGCATCTCTAAATAGGTTTTTGGACAATGGATTCG

ACCCTAACACGGAATATGGTACTCTACAATCTCCTCTTGAAATGGCTGTA

ATGTTCAAGAATACCGAGGCTATAAAAATCTTGATGAGGTATGGAGCTAA

ACCTGTAGTTACTGAATGCACAACTTCTTGTCTGCATGATGCGGTGTTGA

GAGACGACTACAAAATAGTGAAAGATCTGTTGAAGAATAACTATGTAAAC

AATGTTCTTTACAGCGGAGGCTTTACTCCTTTGTGTTTGGCAGCTTACCT

TAACAAAGTTAATTTGGTTAAACTTCTATTGGCTCATTCGGCGGATGTAG

ATATTTCAAACACGGATCGGTTAACTCCTCTACATATAGCCGTATCAAAT

AAAAATTTAACAATGGTTAAACTTCTATTGAACAAAGGTGCTGATACTGA

CTTGCTGGATAACATGGGACGTACTCCTTTAATGATCGCTGTACAATCTG

GAAATATTGAAATATGTAGCACACTACTTAAAAAAAATAAAATGTCCAGA

ACTGGGAAAAATTGATCTTGCCAGCTGTAATTCATGGTAGAAAAGAAGTG

CTCAGGCTACTTTTCAACAAAGGAGCAGATGTAAACTACATCTTTGAAAG

AAATGGAAAATCATATACTGTTTTGGAATTGATTAAAGAAAGTTACTCTG

AGACACAAAAGAGGTAGCTGAAGTGGTACTCTCAAAGGTACGTGACTAAT

TAGCTATAAAAAGGATCCGGGTTAATTAATTAGTCATCAGGCAGGGCGAG

AACGAGACTATCTGCTCGTTAATTAATTAGAGCTTCTTTATTCTATACTT

AAAAAGTGAAAATAAATACAAAGGTTCTTGAGGGTTGTGTTAAATTGAAA

GCGAGAAATAATCATAAATTATTTCATTATCGCGATATCCGTTAAGTTTG

TATCGTAATGGAGAAAATCGTGCTGCTGCTGGCCATCGTGAGCCTGGTGA

AAAGCGATCAGATCTGCATCGGCTACCACGCCAACAACAGCACAGAGCAA

GTGGACACAATCATGGAAAAGAACGTGACCGTGACACACGCCCAGGACAT

CCTGGAAAAGACACACAACGGGAAGCTGTGCGATCTGGATGGAGTGAAGC

CTCTGATCCTGAGAGATTGCAGCGTGGCCGGATGGCTGCTGGGGAACCCA

ATGTGCGACGAATTCATCAACGTGCCCGAATGGAGCTACATCGTGGAGAA

GGCCAACCCAGCCAACGACCTGTGCTACCCAGGGAACCTGAACGACTACG

AAGAACTGAAACACCTGCTGAGCAGAATCAACCACTTTGAGAAAATCCAG

ATCATCCCCAAAAGCAGCTGGTCCGATCACGAAGCCAGCAGCGGAGTGAG

CAGCGCCTGCCCATACCAGGGAAAGTCCAGCTTTTTTAGAAACGTGGTGT

GGCTGATCAAAAAGAACAGCGCCTACCCAACAATCAAGAGAAGCTACAAC
```

```
AACACCAACCAGGAAGATCTGCTGGTGCTGTGGGGATCCACCACCCTAA

CGATGCCGCCGAGCAGACAAGGCTGTACCAGAACCCAACCACCTACATCT

CCGTGGGGACAAGCACACTGAACCAGAGACTGGTGCCAAAAATCGCCATC

AGATCCAAAGTGAACGGGCAGAGCGGAAGAATGGAGTTCTTCTGGACAAT

CCTGAAACCCAACGATGCCATCAACTTCGAGAGCAACGGAAACTTCATCG

CCCCAGAATACGCCTACAAAATCGTGAAGAAAGGGGACAGCGCCATCATG

AAAAGCGAACTGGAATACGGCAACTGCAACACCAAGTGCCAGACCCCAAT

GGGGGCCATCAACAGCAGCATGCCATTCCACAACATCCACCCTCTGACCA

TCGGGGAATGCCCCAAATACGTGAAAAGCAACAGACTGGTGCTGGCCACC

GGGCTGAGAAACAGCCCTCAGAGAGAGACCAGAGGACTGTTTGGAGCCAT

CGCCGGCTTTATCGAGGGAGGATGGCAGGGAATGGTGGATGGCTGGTACG

GATACCACCACAGCAACGAGCAGGGGAGCGGATACGCCGCCGACAAAGAA

TCCACCCAGAAGGCCATCGACGGCGTGACCAACAAAGTGAACAGCATCAT

CGACAAAATGAACACCCAGTTTGAGGCCGTGGGAAGGGAGTTTAACAACC

TGGAAAGGAGAATCGAGAACCTGAACAAGAAGATGGAGGACGGATTCCTG

GATGTGTGGACCTACAACGCCGAACTGCTGGTGCTGATGGAAAACGAGAG

AACCCTGGACTTTCACGACAGCAACGTGAAGAACCTGTACGACAAAGTGA

GGCTGCAGCTGAGGGATAACGCCAAGGAGCTGGGCAACGGCTGCTTCGAG

TTCTACCACAAATGCGATAACGAATGCATGGAAAGCATCAGAAACGGAAC

CTACAACTACCCCCAGTACAGCGAAGAAGCCAGACTGAAAAGAGAAGAAA

TCTCCGGAGTGAAACTGGAATCCATCGGAACCTACCAGATCCTGAGCATC

TACAGCACAGTGGCCTCCTCCCTGGCCCTGGCCATCATGATGGCCGGACT

GAGCCTGTGGATGTGCTCCAACGGAAGCCTGCAGTGCAGAATCTGCATCT

GACTCGAGTTTTTATTGACTAGTTAATCACGGCCGCTTATAAAGATCTAA

AATGCATAATTTCTAAATAATGAAAAAAAGTACATCATGAGCAACGCGTT

AGTATATTTTACAATGGAGATTAACGCTCTATACCGTTCTATGTTTATTG

ATTCAGATGATGTTTTAGAAAAGAAAGTTATTGAATATGAAAACTTTAAT

GAAGATGAAGATGACGACGATGATTATTGTTGTAAATCTGTTTTAGATGA

AGAAGATGACGCGCTAAAGTATACTATGGTTACAAAGTATAAGTCTATAC

TACTAATGGCGACTTGTGCAAGAAGGTATAGTATAGTGAAAATGTTGTTA

GATTATGATTATGAAAAACCAAATAAATCAGATCCATATCTAAAGGTATC

TCCTTTGCACATAATTTCATCTATTCCTAGTTTAGAATAC
```

What is claimed is:

1. An immunological composition comprising an avipox expression vector, wherein said expression vector comprises a polynucleotide encoding an influenza antigen comprising a polypeptide having the amino acid sequence of, SEQ ID NO:17, and wherein the composition comprises in an effective amount of the avipoxvirus vector expressing the influenza virus antigen set forth in SEQ ID NO: 7 for inducing an immune response against H5 avian influenza virus infection.

2. The immunological composition of claim 1, wherein the composition further comprises one or more of a pharmaceutically or veterinarily acceptable carrier, excipient, vehicle or adjuvant.

3. The immunological composition of claim 1, wherein the avipox-expression vector is an attenuated avipox expression vector.

4. The immunological composition of any one of claims 1 or 2, wherein the avipox expression vector is a fowlpox viral vector or a canarypox viral vector.

5. The immunological composition of claim 4, wherein the expression vector is a canarypox viral vector.

6. The immunological composition of claim 4, wherein the fowlpox viral vector comprises a polynucleotide having the sequence as set forth in SEQ ID NO:14.

7. The immunological composition of claim 5, wherein the canarypox viral vector comprises a polynucleotide having the sequence as set forth in SEQ ID NO:15, SEQ ID NO:18, or SEQ ID:22.

8. The immunological composition of claim 1, wherein the composition is capable of inducing a protective immune response against H5 avian influenza virus infection.

9. The composition of claim 7, wherein the polynucleotide comprises the DNA sequence of SEQ ID NO:15.

10. The composition of claim 7, wherein the polynucleotide comprises the DNA sequence of SEQ ID NO:22.

11. The composition of claim 7, wherein the polynucleotide comprising the DNA sequence of SEQ ID NO:18.

12. The composition of claim 1, wherein the composition can be administered to an animal by a method selected from the group consisting of oral, intramuscular, and subcutaneous delivery.

13. The composition of claim 1, wherein an effective amount of the composition can be administered by a needleless apparatus to animals to induce a protective immune response against H5 avian influenza.

* * * * *